US010906955B2

(12) United States Patent
Berasi et al.

(10) Patent No.: US 10,906,955 B2
(45) Date of Patent: Feb. 2, 2021

(54) RECOMBINANT ROBO2 PROTEINS, COMPOSITIONS, METHODS AND USES THEREOF

(71) Applicants: Pfizer Inc., New York, NY (US); Boston Medical Center Corporation, Boston, MA (US)

(72) Inventors: Stephen Berasi, Arlington, MA (US); Janet Elizabeth Buhlmann, Brookline, MA (US); Nathan Higginson-Scott, Boston, MA (US); Michael Shamashkin, Woburn, MA (US); Matthew Russo, Silver Spring, MD (US); Stefano V. Gulla, Boston, MA (US); Zong Sean Juo, Cambridge, MA (US); Sreekumar R. Kodangattil, Lexington, MA (US); Weining Lu, Boston, MA (US); Xueping Fan, Boston, MA (US); David J. Salant, Boston, MA (US)

(73) Assignees: Pfizer Inc., New York, NY (US); Boston Medical Center Corporation, Boston, MA (US)

( * ) Notice: Subject to any disclaimer, the term of this patent is extended or adjusted under 35 U.S.C. 154(b) by 0 days.

(21) Appl. No.: 15/995,286

(22) Filed: Jun. 1, 2018

(65) Prior Publication Data

US 2018/0346542 A1 Dec. 6, 2018

Related U.S. Application Data

(60) Provisional application No. 62/514,242, filed on Jun. 2, 2017, provisional application No. 62/663,082, filed on Apr. 26, 2018.

(51) Int. Cl.

| | |
|---|---|
| *C07K 14/705* | (2006.01) |
| *C07K 19/00* | (2006.01) |
| *C12N 15/09* | (2006.01) |
| *C12N 15/11* | (2006.01) |
| *C12N 15/52* | (2006.01) |
| *C12N 15/63* | (2006.01) |
| *C07H 21/04* | (2006.01) |
| *A61P 13/12* | (2006.01) |
| *A61K 38/17* | (2006.01) |
| *A61K 38/00* | (2006.01) |

(52) U.S. Cl.
CPC ........ *C07K 14/70503* (2013.01); *A61K 38/17* (2013.01); *A61P 13/12* (2018.01); *C07H 21/04* (2013.01); *C07K 19/00* (2013.01); *C12N 15/09* (2013.01); *C12N 15/11* (2013.01); *C12N 15/52* (2013.01); *C12N 15/63* (2013.01); *A61K 38/00* (2013.01); *C07K 2319/30* (2013.01); *C07K 2319/31* (2013.01); *C07K 2319/70* (2013.01)

(58) Field of Classification Search
None
See application file for complete search history.

(56) References Cited

U.S. PATENT DOCUMENTS

| 7,939,497 B2 | 5/2011 | Geng | |
|---|---|---|---|
| 9,493,529 B2 | 11/2016 | Blanche | |
| 9,572,879 B2 | 2/2017 | Lu | |
| 10,358,677 B2 | 7/2019 | Lu | |
| 2005/0059040 A1 | 3/2005 | Goodman | |
| 2010/0233819 A1 | 9/2010 | Goodman | |
| 2013/0273049 A1 | 10/2013 | Dol-Gleizes | |
| 2016/0002357 A1* | 1/2016 | May ...................... | C07K 16/18 424/136.1 |
| 2017/0114412 A1 | 4/2017 | Lu | |

FOREIGN PATENT DOCUMENTS

| WO | WO1999020764 | 4/1999 | |
|---|---|---|---|
| WO | WO2012085178 | 6/2011 | |
| WO | WO2011128561 | 10/2011 | |
| WO | WO2013103811 | 7/2013 | |
| WO | WO-2015168643 A2 * | 11/2015 | ............ C07K 16/00 |
| WO | WO2017055395 | 4/2017 | |

OTHER PUBLICATIONS

Robo2-Fc Product Sheet, R&D Systems, Revised Aug. 2, 2013; 1 page; no author indicated. (Year: 2013).*
Zhang et al, 2010. Journal of Chemical Neuroanatomy. 39: 256-26 (Year: 2010).*
Wells (Sep. 18, 1990) "Additivity of Mutational Effects in Proteins." Biochemistry 29(37): 8509-8517 (Year: 1990).*
Ngo et al. (Mar. 2, 1995) "The Protein Folding Problem and Tertiary Structure Prediction, Chapter 14: Computational Complexity Protein Structure Prediction, and the Levinthal Paradox" pp. 492-495 (Year: 1995).*
Greaves et al., "Estrogen Receptor (ER) Agonists Differentially Regulate Neuroangiogenesis in Peritoneal Endometriosis via the Repellent Factor SLIT3," Endocrinology, 155(10):4015-4026 (2014).
R&D Systems: "Recombinant Human ROBO2 Fc Chimera," Catalog No. 3147-RB (Oct. 28, 2017) (5 pages).
R&D Systems: "Recombinant Mouse ROBO2 Fc Chimera," Catalog No. 8366-RB (Oct. 28, 2017) (5 pages).
Ricaño-Cornejo et al. "Slit-Robo Signals Regulate Pioneer Axon Pathfinding of the Tract of the Postoptic Commissure in the Mammalian Forebrain," Journal of Neuroscience Research, 89(10):1531-1541 (2011).
Bashaw et al., "Repulsive axon guidance: Abelson and Enabled play opposing roles downstream of the roundabout receptor," Cell, 101(7):703-715 (2000).

(Continued)

*Primary Examiner* — Zachary C Howard
(74) *Attorney, Agent, or Firm* — Haley Guiliano LLP; James F. Haley, Jr.; Brian M. Gummow

(57) ABSTRACT

The invention provides recombinant Roundabout Receptor 2 (ROBO2) proteins designed to bind SLIT ligands and prevent their binding to ROBO2 cell surface receptors. Also provided are methods for use of these recombinant ROBO2 proteins.

48 Claims, 14 Drawing Sheets

Specification includes a Sequence Listing.

(56) References Cited

OTHER PUBLICATIONS

Bertoli-Avella et al., "ROBO2 gene variants are associated with familial vesicoureteral reflux," Journal of American Society of Nephrology, 19(4):825-31 (2008).
Bork, "Powers and pitfalls in sequence analysis: the 70% hurdle," Genome Research, 10(4):398-400 (2000).
Brenner, "Errors in genome annotation," Trends in Genetics, 15(4):132-133 (1999).
Dickinson et al., "Novel regulated expression of the SLIT/ROBO pathway in the ovary: possible role during luteolysis in women," Endocrinology, 149(10): 5024-5034 (2008).
Dickinson et al., "The SLIT-ROBO pathway: a regulator of cell function with implications for the reproductive system," Reproduction, 139(4):697-704 (2010).
Dickson et al., "Regulation of commissural axon pathfinding by slit and its Robo receptors," Annual Review of Cell and Development Biology, 22:651-675(2006).
Doerks et al., Protein annotation: detective work for function prediction, Trends in Genetics, 14(6):248-250 (1998).
Evans et al. "Functional diversity of Robo receptor immunoglobulin domains promotes distinct axon guidance decisions," Current Biology, 20(6):567-572 (2010).
Fan et al., "Inhibitory effects of Robo2 on nephrin: a crosstalk between positive and negative signals regulating podocyte structure," Cell Reports, 2(1):52-61 (2012).
Fan et al., "Robot is a Podocyte Protein Required for Normal Glomerular Filtration Barrier Function," Journal of American Nephrology, 20:64A (2009) (Abstract F-FC272) (1 page).
Ferrari, "Prescribing angiotensin-converting enzyme inhibitors and angiotensin receptor blockers in chronic kidney disease", Nephrology 12(1):81-89 (2007).
Grieshammer et al., "SLIT2-mediated ROBO2 signaling restricts kidney induction to a single site," Development Cell, 6(5)709-717 (2004).
Guan et al., "Signalling mechanisms mediating neuronal responses to guidance cues," Nature Reviews Neurosciences, 4(12):941-956 (2003).
Halaby et al., "The immunoglobulin fold family sequence analysis and 3D structure comparisons," Protein Engineering, 12(7):563-571 (1999).
Han et al., "Over-expression of Slit2 induces vessel formation and changes blood vessel permeability in mouse brain," Acta Pharmacologica Sinica, 32(11):1327-1336 (2011).

Hivert et al., "Robo1 and Robo2 are homophilic binding molecules that promote axonal growth," Molecular and Cellular Neurosciences, 21(4):534-545 (2002).
Hocking et al., "Distinct roles for Robo2 in the regulation of axon and dendrite growth by retinal ganglion cells," Mechanisms of Development 127(1-2):36-48 (2010).
Japanese Notice of Reason of Rejection received in JP Application No. 2014-551337, dated Sep. 14, 2016 (10 pages).
Kanellis et al., "Modulation of inflammation by slit protein in vivo in experimental crescentic glomerulonephritis," American Journal of Pathology, 165(1):341-352 (2004).
Kidd et al., "Roundabout controls axon crossing of the CNS midline and defines a novel subfamily of evolutionarily conserved guidance receptors," Cell, 92(2):205-215 (1998).
Lindenmeyer et al., Systematic analysis of a novel human renal glomerulus-enriched gene expression dataset, PLoS One, 5(7):e11545 (2010).
Liu et al., "Extracellular Ig domains 1 and 2 of Robo are important for ligand (Slit) binding", Molecular and Cellular Neurosciences, 26:232-240 (2004).
Lu et al., "Disruption of ROBO2 is associated with urinary tract anomalies and confers risk of vesicoureteral reflux", American Journal of Human Genetics, 80(4):616-632 (2007).
Ngo et al., "The protein folding problem and tertiary structure prediction, Chapter 14: Computational Complexity Protein Structure Prediction, and the levinthal paradox", pp. 433-506 (1994).
Piper et al., "Signaling mechanisms underlying Slit2-induced collapse of Xenopus retinal growth cones," Neuron, 49(2):215-228 (2006).
Schlondorff, "Nephrin AKTs on actin: The slit diaphragm-actin cytoskeleton signaling network expands," Kidney International, 73(5):524-526 (2008).
Shiau et al., "Robo2-Slit1 dependent cell-cell interactions mediate assembly of the trigeminal ganglion," Nature Neuroscience, 11(3):269-276 (2008).
Skolnick et al., "From genes to protein structure and function: novel applications of computational approaches in the genomic era," Trends in Biotechnology, 18(1):34-39 (2000).
Small et al., "MicroRNA-218 regulates vascular patterning by modulation of Slit-Robo signaling", Circulation Research, 107(11):1336-1344 (2010).
Zhou et al., "The role of SLIT-ROBO signaling in proliferative diabetic retinopathy and retinal pigment epithelial cells," Molecular Vision, 17:1526-1536 (2011).

* cited by examiner

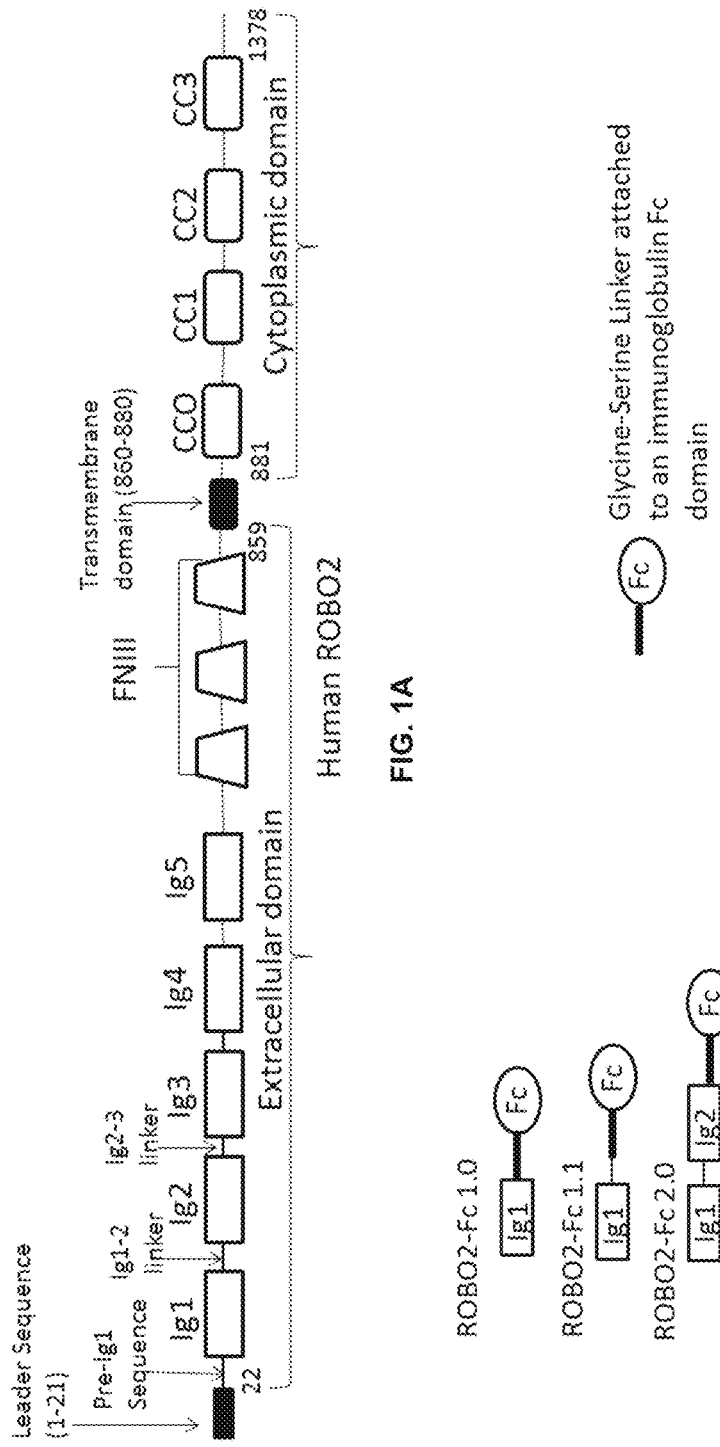

```
1   SRLRQEDFP PRIVEHPSDVIVSKGEPTTLN      30
31  CKAEGRPTPTIEWYKDGERVETDKDDPRSH       60
61  RMLLPSGSLFFLRLVHGRRSKPDEGSYVCV       90
91  ARNYLGEAVSRNASLEVALLRDDFRQNPTD      120
121 VVVAAGEPAILEQPPRGHPEPTIYWKKDK       150
151 VRIDDKEERIRGGKLMISNTRKSDAGMY        180
181 TCVGTNMVGERDSDPAELTVFERGGSGGSe      210
211 pkssdkthtppcpapeaagapsvflfppk       240
241 pkdtlmisrtpevtcvvvdvshedpevkfn      270
271 wyvdgvevhnaktkpreeqynstyrvvsvl      300
301 tvlhqdwingkeykckvsnkalpapiekti      330
331 skakgqprepqvtlppsreemtknqvslt       360
361 clvkgfypsdiavewesngqpennykttpp      390
391 vldsgsfflyskltvdksrwqqgnvfscs       420
421 vmhealhnhytqksislspg                440
```

Second Polypeptide chain

FIG. 2

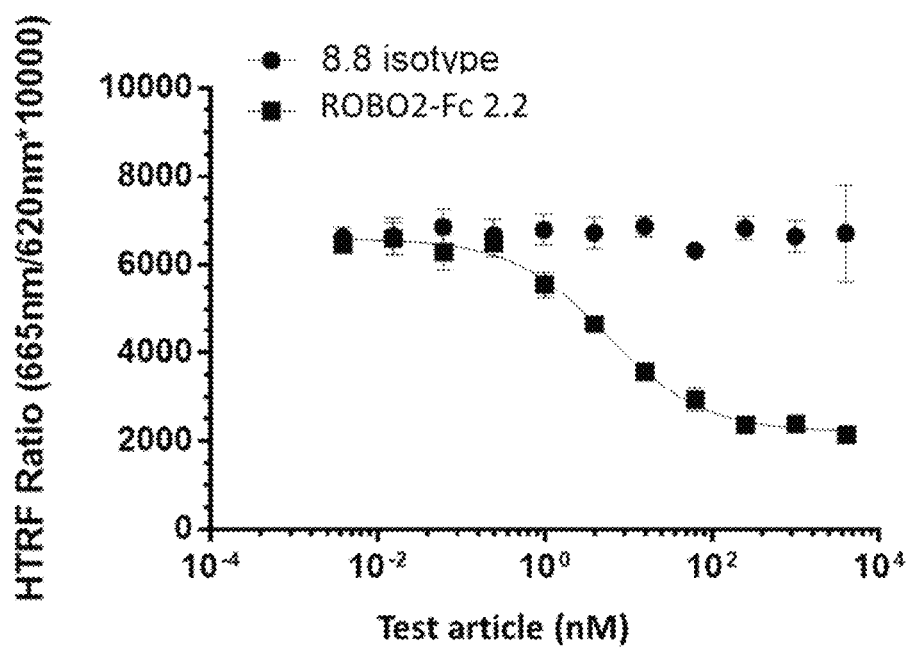
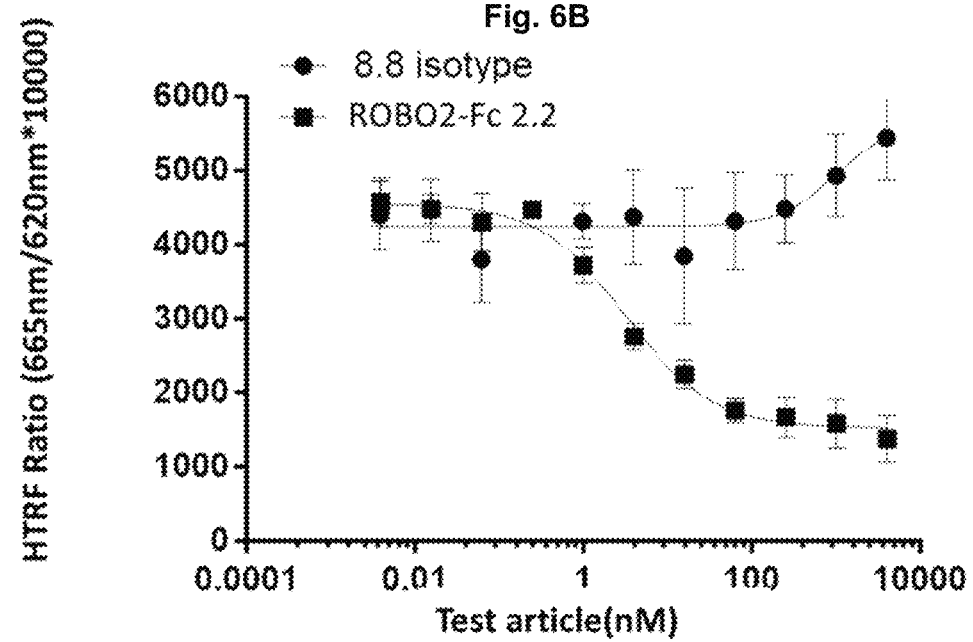

RECOMBINANT ROBO2 PROTEINS, COMPOSITIONS, METHODS AND USES THEREOF

CROSS-REFERENCE TO RELATED APPLICATION

This application claims the benefit of U.S. Provisional Application Nos. 62/514,242, filed Jun. 2, 2017; and 62/663,082, filed Apr. 26, 2018, which are hereby incorporated by reference here in their entirety.

PARTIES TO A JOINT RESEARCH STATEMENT

The presently claimed invention was made by or on behalf of the below listed parties to a joint research agreement. The joint research agreement was in effect on or before the date the claimed invention was made and the claimed invention was made as a result of activities undertaken within the scope of the joint research agreement. The parties to the joint research agreement are BOSTON MEDICAL CENTER CORP. and PFIZER INC.

SEQUENCE LISTING

The instant application contains a Sequence Listing which has been submitted electronically in ASCII format and is hereby incorporated by reference in its entirety. Said ASCII copy, created on May 3, 2018, is named PCFC-0043-101-SL.txt and is 54,386 bytes in size.

BACKGROUND

Chronic kidney disease (CKD) is a worldwide public health problem, which often leads to end-stage renal failure. CKD affects an estimated 13% of the population or ~27 million in the United States and over 500 million people worldwide. The prevalence of CKD is predicted to continue to increase because of the ongoing epidemic of diabetes and obesity within the general population. About half a million CKD patients in the US (~7 million worldwide) will progress to end-stage renal disease (ESRD) and need dialysis or kidney transplantation for survival. The morbidity and mortality of ESRD are high and cost the US at least $40 billion each year. Proteinuria (i.e., the presence of an excess of serum proteins in the urine—commonly defined as urine albumin level>30 mg/day) is an early biomarker, risk factor and surrogate outcome of CKD in patients with and without diabetes. Treatment to reduce the level of proteinuria during early stages of CKD can slow progression to ESRD. However, there is no kidney podocyte specific anti-proteinuric treatment currently available for CKD patients with proteinuria.

Podocytes are specialized epithelial cells that extend primary and secondary processes to cover the outer surface of the glomerular basement membrane. The actin-rich inter-digitating secondary processes (i.e., foot processes) from neighboring podocytes create filtration slits bridged by a semi-porous slit-diaphragm that forms the final barrier to protein permeation. Proteinuria is the clinical signature of podocyte injury in diabetic and non-diabetic kidney disease. There is an expanding group of published studies showing that hereditary, congenital, or acquired abnormalities in the molecular component of podocytes leads to proteinuria. Whereas genetic mutations of podocyte slit-diaphragm proteins such as nephrin and podocin are associated with hereditary forms of proteinuric kidney disease, it has become increasingly evident that the proteins that make up and associate with the slit-diaphragm are more than a simple structural barrier. Thus, substantial evidence suggests that these proteins form a balanced signaling network that may influence podocyte foot process structure and function through interaction with the actin cytoskeleton.

Roundabout (ROBO) Receptors

Roundabout Receptor 2 (ROBO2, also referred to as Roundabout Guidance Receptor 2 or Roundabout homolog 2) is a receptor for Slit Guidance Ligand (SLIT) protein ligands. ROBO2 is expressed at the basal surface of glomerular podocytes in the kidney and Slit Guidance Ligand 2 (SLIT2) is present in kidney glomeruli. Upon SLIT2 binding, ROBO2 forms a complex with nephrin in the glomerular filtration barrier and acts as a negative regulator to inhibit nephrin-induced actin polymerization. The loss of ROBO2 increases the actin polymerization in the podocyte and alleviates the abnormal podocyte structural phenotype found in nephrin-null mice. Loss of ROBO2 also increases adhesion of podocytes to the glomerular basement membrane in mice. These data, along with the observation that a patient with ROBO2 chromosomal translocation lacks proteinuria, suggests that blocking of SLIT2-ROBO2 signaling pathway could increase nephrin-induced actin polymerization to reduce proteinuria. Blocking of ROBO2 signaling may also restore glomerular filtration barrier in proteinuric disease by up-regulation of nephrin induced actin polymerization.

SLIT1, SLIT2 and SLIT3. SLITs are secreted proteins associated with the extracellular matrix. The protein sequence of all SLITs shows a high degree of conservation and have the same structure: an N-terminus signal peptide; four tandem leucine-rich repeat domains (LRR) termed D1-D4; six epidermal growth factor (EGF)-like domains; a laminin G-like domain; a further one (invertebrates) or three (vertebrates) EGF-like domains and a C terminal cysteine knot domain. SLIT ligands can be cleaved to yield a short C-terminus fragment of unknown function (SLIT-C product) and a long N-terminus fragment (SLIT-N product) that is active and mediates binding to ROBOs. SLIT ligands, as well as cleavage products (e.g., SLIT-N, SLIT2-D2) described herein can be used to assess ROBO2 activity.

Four ROBO receptors have been characterized in vertebrates: ROBO1/Dutt1; ROBO2; ROBO3/Rig-1 and ROBO4/Magic Roundabout. ROBO1, ROBO2 and ROBO3 share a common extracellular domain (ECD) structure that is reminiscent of cell adhesion molecules. This region contains five immunoglobulin-like (Ig-like) domains (Ig1, Ig2, Ig3, Ig4 and Ig5) followed by three fibronectin type 3 (FN3) repeats (FIG. 1A). In addition, ROBO2 has four cytoplasmic conserved (CC) sequences in its intracellular domain as illustrated in FIG. 1A.

The sequence of full length human ROBO2 precursor is shown as SEQ ID NO: 24. A 21 amino acid ROBO2 leader sequence (SEQ ID NO: 17; residues 1-21 according to the numbering set forth in SEQ ID NO: 24) is cleaved during protein production to produce mature ROBO2 (FIG. 1A). Residues 22-859 according to the numbering set forth in SEQ ID NO: 24 form the extracellular domain, residues 860-880 set forth in SEQ ID NO: 24 form the transmembrane domain, and residues 881-1378 set forth in SEQ ID NO: 24 form the cytoplasmic domain (FIG. 1A).

Exemplary sequences of the five Ig-like domains (Ig1, Ig2, Ig3, Ig4 and Ig5) of ROBO2 are shown in Table 23. The ROBO2 pre-Ig1sequence (SEQ ID NO: 8), the Ig1-Ig2 inter-domain linker (SEQ ID NO: 10) and the Ig2-Ig3 inter-domain linker (SEQ ID NO: 12) are also disclosed in Table 23.

The D2 LRR domain of the SLITs and Ig1 and Ig2 domains of the ROBOs are evolutionary conserved and are involved in binding. Ig1 and Ig2 domains of ROBO together are also referred to as SLIT-binding domain. Studies have shown that while both immunoglobulin-like (Ig-like) domains 1 and 2 (Ig1 and Ig2) of ROBO2 interact with SLIT; the first Ig-like domain (Ig1) is the primary binding site for SLIT. In addition, previous studies have indicated that removing the three fibronectin type III (FNIII) repeats has a greater negative effect on ROBO binding to SLIT than removal of the third and fourth immunoglobulin-like domains (Ig3 and Ig4) (see, e.g., Liu et al., 2004, Molecular Cellular Neuroanatomy 39:256-261).

Upon ROBO-SLIT binding, Rho GTPases and their regulators (GAPs and GEFs) are involved in the downstream signaling pathway. In the presence of SLIT, SLIT-ROBO Rho GTPase activating protein 1 (srGAP1) binds to the CC3 domain of ROBO and inactivates RhoA and Cdc42. These effector proteins are able to mediate, among other outcomes, repulsion, control of cytoskeletal dynamics and cell polarity. In the presence of SLIT, Vilse/CrossGAP can also bind to the CC2 domain of ROBO and inhibit Rac1 and Cdc42. Rac1 is also activated by the recruitment of the GEF protein Son of sevenless (Sos) via the adaptor protein Dreadlocks (Dock), which binds to the CC2-3 domain of ROBO. This activates the downstream target of Rac1 and p21-activated kinase (Pak), which also binds to ROBO CC2-3 domains. These downstream signaling partners of ROBO control repulsion and cytoskeletal dynamics. The tyrosine kinase Abelson (Abl) can also bind ROBO CC3 domain and antagonizes ROBO signaling through phosphorylation of the CC1 domain and mediates cell adhesion. Enabled (Ena), a substrate of Abl, also binds ROBO CC1 and CC2 domains. All these downstream ROBO-SLIT molecules may be used to assess ROBO2 activity, as well as to assess any neutralizing effect of a novel recombinant ROBO2 protein disclosed herein.

In the kidney, ROBO2 forms a complex with nephrin through adaptor protein Nck. In contrast to the role of nephrin that promotes actin polymerization, SLIT-ROBO2 signaling inhibits nephrin-induced actin polymerization. Thus, the binding of ROBO2 intracellular domain and Nck may be used to assess ROBO2 activity.

Patients suffering from many glomerular diseases (including Focal Segmental Glomerular Sclerosis) currently have no therapies available to preserve renal function or otherwise treat the disease. Further, there is no treatment currently available for CKD patients with proteinuria. Accordingly, there is a need for developing a therapeutic that modulates ROBO2-SLIT signaling, thereby preserving or modulating podocyte functions and reducing proteinuria or otherwise treating or preventing a renal disease associated with or mediated by ROBO2-SLIT binding and signaling.

SUMMARY OF THE INVENTION

The invention provides recombinant ROBO2 proteins that bind to SLIT ligands, as well as uses, and associated methods thereof. Those skilled in the art will recognize, or be able to ascertain using no more than routine experimentation, many equivalents to the specific embodiments of the invention described herein. Such equivalents are intended to be encompassed by the following embodiments (E).

E1. A recombinant Roundabout Receptor 2 (ROBO2) protein comprising amino acid residues 1 to 203 according to the numbering of SEQ ID NO: 1, and further comprising an immunoglobulin heavy chain constant domain.

E2. A recombinant Roundabout Receptor 2 (ROBO2) protein consisting essentially of amino acid residues 1 to 203 according to the numbering of SEQ ID NO: 1, and an immunoglobulin heavy chain constant domain.

E3. A recombinant Roundabout Receptor 2 (ROBO2) protein comprising (i) a SLIT-binding moiety; and (ii) a half-life extending moiety, wherein said SLIT-binding moiety comprises a portion of the ROBO2 extracellular domain.

E4. The recombinant ROBO2 protein of E3, wherein said portion of said ROBO2 extracellular domain comprises the first two immunoglobulin-like (Ig1 and Ig2) domains of ROBO2 and a C-terminus sequence consisting of the sequence of SEQ ID NO: 12.

E5. The recombinant ROBO2 protein of E3, wherein said portion of said ROBO2 extracellular domain consists essentially of ROBO2 pre-immunoglobulin-like 1 (Ig1) sequence (SRLRQEDFP (SEQ ID NO: 8), first immunoglobulin-like domain (Ig1), inter-domain linker between first and second immunoglobulin-like domains (Ig1-Ig2 inter-domain linker; VALLR (SEQ ID NO: 10)), second immunoglobulin-like domain (Ig2), and inter-domain linker between second and third immunoglobulin-like domains (Ig2-Ig3 inter-domain linker; VFER (SEQ ID NO: 12)).

E6. The recombinant ROBO2 protein of any one of E3-E5, wherein said portion of said ROBO2 extracellular domain consists essentially of amino acid residues 1 to 203 according to the numbering of SEQ ID NO: 1.

E7. The recombinant ROBO2 protein of any one of E3-E6, wherein said half-life extending moiety comprises an immunoglobulin domain.

E8. The recombinant ROBO2 protein of any one of E1, E2 or E7, wherein said immunoglobulin domain is an Fc domain of an $IgA_1$ $IgA_2$, IgD, IgE, IgM, $IgG_1$, $IgG_2$, $IgG_3$, or $IgG_4$.

E9. The recombinant ROBO2 protein of E8, wherein said Fc domain is the Fc domain of human $IgG_1$.

E10. The recombinant ROBO2 protein of E9, wherein said Fc domain is modified to eliminate effector function.

E11. The recombinant ROBO2 protein of E10, wherein said Fc domain is the Fc domain of human $IgG_1$, and wherein said human IgG1 Fc domain comprises at least one mutation selected from the group consisting of a substitution from leucine to alanine at amino acid residue number 234 (L234A), a substitution from leucine to alanine at amino acid residue number 235 (L235A), and a substitution from glycine to alanine at amino acid residue number 237 (G237A) all according to the Eu numbering as set forth in Kabat.

E12. The recombinant ROBO2 protein of E9-E11, wherein said human IgG1 Fc domain does not comprise a lysine at residue number 447 according to the Eu numbering as set forth in Kabat.

E13. The recombinant ROBO2 protein of any one of E11-E12, wherein said Fc domain comprises amino acid residues 210 to 440 according to the numbering of SEQ ID NO: 1.

E14. The recombinant ROBO2 protein of any one of E11-E12, wherein said Fc domain consists of amino acid residues 210 to 440 according to the numbering of SEQ ID NO: 1.

E15. The recombinant ROBO2 protein of any one of E1, E2 or E7, wherein said amino acid residues 1 to 203 according to the numbering of SEQ ID NO: 1 are contiguous with said immunoglobulin domain.

E16. The recombinant ROBO2 protein of any one of E1, E2 or E7, wherein said amino acid residues 1 to 203 according to the numbering of SEQ ID NO: 1 are connected via a linker to said immunoglobulin domain.

E17. The recombinant ROBO2 protein of E16, wherein said linker is a peptidyl linker comprising from about 1 to 30 amino acid residues.

E18. The recombinant ROBO2 protein of E17, wherein said peptidyl linker is selected from the group consisting of:
a) a glycine rich peptide;
b) a peptide comprising glycine and serine;
c) a peptide having a sequence (Gly-Gly-Ser)$_n$, wherein n is 1, 2, 3, 4, 5, or 6 (SEQ ID NO: 22); and
d) a peptide having a sequence (Gly-Gly-Gly-Gly-Ser)$_n$, wherein n is 1, 2, 3, 4, 5, or 6 (SEQ ID NO: 23).

E19. The recombinant ROBO2 protein of E18, wherein said peptidyl linker is (Gly-Gly-Ser)$_2$ (SEQ ID NO: 15).

E20. A recombinant ROBO2-Fc protein comprising the amino acid sequence of SEQ ID NO: 1.

E21. A recombinant ROBO2-Fc protein consisting of the amino acid sequence of SEQ ID NO: 1.

E22. A recombinant ROBO2-Fc protein comprising an amino acid sequence at least 90% identical to the amino acid sequence of SEQ ID NO: 1.

E23. The recombinant ROBO2 protein of any one of E1-E22, comprising the amino acid sequence encoded by the insert of the plasmid deposited at the ATCC and having ATCC Accession No. PTA-124008.

E24. The recombinant ROBO2-Fc protein of any one of E4 or E5, wherein said Ig1 of ROBO2 comprises at least one of the following mutations: S17T and R73Y, each numbered according to SEQ ID NO: 1.

E25. A recombinant ROBO2-Fc protein comprising the amino acid sequence of SEQ ID NO: 19.

E26. The recombinant ROBO2-Fc protein of E25, wherein the protein does not comprise a C-terminal lysine located at amino acid residue number 441 according to the numbering of SEQ ID NO: 19.

E27. The recombinant ROBO2 protein of any one of E1-E26, wherein said ROBO2 is human ROBO2.

E28. The recombinant ROBO2 protein of any one of E1-E27, wherein said protein binds SLIT2 with a binding affinity ($K_D$) of or less than: about 10 nM, about 5 nM, about 2 nM, about 1 nM, about 900 pM, about 800 pM, about 700 pM, about 600 pM, about 500 pM, about 400 pM, about 300 pM, about 250 pM, about 200 pM, about 150 pM, about 100 pM, about 50 pM, about 40 pM, about 30 pM, about 25 pM, about 20 pM, about 15 pM, about 10 pM, about 5 pM, or about 1 pM.

E29. The recombinant ROBO2 protein of any one of E1-E27, wherein said protein binds SLIT2 with a $K_D$ that is at least about 2-fold, about 4-fold, about 6-fold, about 8-fold, about 10-fold, about 20-fold, about 40-fold, about 60-fold, about 80-fold, about 100-fold, about 120-fold, about 140-fold, about 160-fold, lower than the $K_D$ value for binding of ROBO1 to SLIT2.

E30. The recombinant ROBO2 protein of any one of E1-E29, wherein said protein binds SLIT2 with a $K_D$ value that is at least about 2-fold, about 4-fold, about 6-fold, about 8-fold, about 10-fold, about 20-fold, about 40-fold, about 60-fold, about 80-fold, about 100-fold, about 120-fold, about 140-fold, about 160-fold, lower than the $K_D$ value for binding of a ROBO1-Fc protein to SLIT2.

E31. The recombinant ROBO2 protein of any one of E28-E30, wherein said $K_D$ is measured by surface plasmon resonance (SPR).

E32. The recombinant ROBO2 protein of E31, wherein said $K_D$ is measured using a Biacore T200 instrument.

E33. The recombinant ROBO2 protein of any one of E28-E30, wherein said $K_D$ is measured by bio-layer interferometry (BLI).

E34. The recombinant ROBO2 protein of E33, wherein said $K_D$ is measured using a ForteBio Octet instrument.

E35. The recombinant ROBO2 protein of any one of E1-E34, wherein said protein inhibits binding of a SLIT ligand and ROBO2.

E36. The recombinant ROBO2 protein of any one of E1-E34, wherein said protein inhibits ROBO2-dependent SLITx-N activity.

E37. The recombinant ROBO2 protein of any one of E1-E36, wherein said protein inhibits binding of a SLIT ligand and ROBO2 and inhibits ROBO2-dependent SLIT-N activity.

E38. The recombinant ROBO2 protein of any one of E1-E37, wherein said ROBO2-dependent SLITx-N activity is selected from the group consisting of actin polymerization, podocyte adhesion, and inhibition of neuronal cell migration.

E39. The recombinant ROBO2 protein of any one of E1-E38, wherein said protein has a half maximal inhibitory concentration ($IC_{50}$) of not more than about 15 nM, about 13 nM, about 11 nM, about 9 nM, about 7 nM, about 6 nM, about 5 nM, about 4 nM, about 3 nM, about 2 nM, about 1 nM.

E40. The recombinant ROBO2 protein of E39, wherein said $IC_{50}$ is measured by a homogenous time-resolved fluorescence (HTRF) assay for inhibition of binding of ROBO2 to SLIT2.

E41. The recombinant ROBO2 protein of any one of E1-E40, wherein said protein has a half maximal $IC_{50}$ of not more than about 75 nM, about 65 nM, about 55 nM, about 45 nM, about 35 nM, about 25 nM, about 15 nM, about 5 nM.

E42. The recombinant ROBO2 protein of E41, wherein said $IC_{50}$ is assessed by measuring SLIT2-N mediated inhibition of neuronal cell migration.

E43. The recombinant ROBO2 protein of any one of E28-E42, wherein said SLIT2 is human SLIT2.

E44. The recombinant ROBO2 protein of any one of E1-E43, wherein two of said recombinant ROBO2 proteins associate to form a homodimer.

E45. An isolated nucleic acid molecule encoding the recombinant ROBO2 protein of any one of E1-E44.

E46. The isolated nucleic acid molecule of E45 comprising the nucleic acid sequence of SEQ ID NO: 21.

E47. The isolated nucleic acid molecule of E45 consisting of the nucleic acid sequence of SEQ ID NO: 21.

E48. An isolated nucleic acid comprising the nucleic acid sequence of the insert of the plasmid deposited at the ATCC and having ATCC Accession No. PTA-124008.

E49. A recombinant ROBO2 protein comprising an amino acid sequence encoded by the sequence of SEQ ID NO: 21.

E50. A recombinant ROBO2 protein comprising an amino acid sequence encoded by a sequence that is at least 85%, 90%, 95%, or 99% identical to the sequence of SEQ ID NO:

E51. A recombinant ROBO2 protein comprising an amino acid sequence encoded by a sequence capable of hybridizing under highly stringent conditions to the sequence of SEQ ID NO: 21.

E52. A vector comprising the nucleic acid molecule of any one of E45-E48.

E53. A host cell comprising the nucleic acid molecule of any one of E45-E48.

E54. A host cell comprising the vector of E52.

E55. The host cell of E53 or E54, wherein said cell is a mammalian cell.

E56. The host cell of E53 or E54, wherein said host cell is a CHO cell, a HEK-293 cell, or a Sp2.0 cell.

E57. A method of making a recombinant ROBO2 protein, comprising culturing the host cell of any one of E53-E56 under conditions wherein said recombinant ROBO2 protein is expressed.

E58. The method of E57, further comprising isolating said recombinant ROBO2 protein.

E59. A pharmaceutical composition comprising a recombinant ROBO2 protein of any one of E1-E44, and a pharmaceutically acceptable carrier or excipient.

E60. A method of reducing the biological activity of ROBO2, comprising administering to a subject in need thereof a therapeutically effective amount of the recombinant ROBO2 protein of any one of E1-E44, or the pharmaceutical composition of E59.

E61. The method of E60, wherein said biological activity of ROBO2 is selected from the group consisting of binding to at least one SLIT ligand, actin polymerization, podocyte adhesion, inhibiting SLIT2-N-mediated inhibition of neuronal cell migration, binding of ROBO2 with srGAP1, and binding of ROBO2 with Nck.

E62. A method of treating renal disease, comprising administering to a subject in need thereof a therapeutically effective amount of the recombinant ROBO2 protein of any one of E1-E44, or the pharmaceutical composition of E59.

E63. A method of preserving podocyte function, comprising contacting said podocyte with the recombinant ROBO2 protein of any one of E1-E44, or the pharmaceutical composition of E59.

E64. A method of modulating podocyte function, comprising contacting said podocyte with the recombinant ROBO2 protein of any one of E1-E44, or the pharmaceutical composition of E59.

E65. A method of treating glomerular disease, comprising administering to a subject in need thereof a therapeutically effective amount of the recombinant ROBO2 protein of any one of any one of E1-E44, or the pharmaceutical composition of E59.

E66. A method of treating Focal Segmental Glomerular Sclerosis (FSGS), comprising administering to a subject in need thereof a therapeutically effective amount of the recombinant ROBO2 protein, of any one of E1-E44, or the pharmaceutical composition of E59.

E67. A method of treating nephropathy comprising administering to a subject in need thereof a therapeutically effective amount of the recombinant ROBO2 protein of any one of E1-E44, or the pharmaceutical composition of E59.

E68. The method of E67, wherein said nephropathy is IgA nephropathy.

E69. The method of any one of E60-E68, wherein said subject is a human.

E70. The method of any one of E60-E69, wherein said recombinant ROBO2 protein, or pharmaceutical composition is administered intravenously.

E71. The method of any one of E60-E69, wherein said recombinant ROBO2 protein, or pharmaceutical composition is administered subcutaneously.

E72. The method of any one of E60-E71, wherein recombinant ROBO2 protein, or pharmaceutical composition, is administered about twice a week, once a week, once every two weeks, once every three weeks, once every four weeks, once every five weeks, once every six weeks, once every seven weeks, once every eight weeks, once every nine weeks, once every ten weeks, twice a month, once a month, once every two months, once every three months, or once every four months.

E73. The recombinant ROBO2 protein of any one of E1-E44, or the pharmaceutical composition of E59, for use as a medicament.

E74. The recombinant ROBO2 protein of any one of E1-E44, or the pharmaceutical composition of E59, for use in reducing the activity of ROBO2 in a cell.

E75. The recombinant ROBO2 protein of any one of E1-E44, or the pharmaceutical composition of E59, for use in reducing the activity of ROBO2 in a subject.

E76. The recombinant ROBO2 protein of any one of E1-E44, or the pharmaceutical composition of E59, for use in preserving podocyte function in a subject.

E77. The recombinant ROBO2 protein of any one of E1-E44, or the pharmaceutical composition of E59, for use in modulating podocyte function in a subject.

E78. The recombinant ROBO2 protein of any one of E1-E44, or the pharmaceutical composition of E59, for use in treating a glomerular disease in a subject.

E79. The recombinant ROBO2 protein of E78, wherein said glomerular disease is FSGS.

E80. The recombinant ROBO2 protein of any one of E1-E44, or the pharmaceutical composition of E59, for use in treating nephropathy in a subject.

E81. The recombinant ROBO2 protein of E80, wherein said nephropathy is an IgA nephropathy.

E82. Use of the recombinant ROBO2 protein of any one of E1-E44, or the pharmaceutical composition of E59, in the manufacture of a medicament for reducing the activity of ROBO2 in a cell.

E83. Use of the recombinant ROBO2 protein of any one of E1-E44, or the pharmaceutical composition of E59, in the manufacture of a medicament for reducing the activity of ROBO2 in a subject.

E84. Use of the recombinant ROBO2 protein of any one of E1-E44, or the pharmaceutical composition of E59, in the manufacture of a medicament for preserving podocyte function in a subject.

E85. Use of the recombinant ROBO2 protein of any one of E1-E44, or the pharmaceutical composition of E59, in the manufacture of a medicament for modulating podocyte function in a subject.

E86. Use of the recombinant ROBO2 protein of any one of E1-E44, or the pharmaceutical composition of E59, in the manufacture of a medicament for treating a glomerular disease in a subject.

E87. Use of the recombinant ROBO2 protein of any one of E1-E44, or the pharmaceutical composition of E59, in the manufacture of a medicament for treating nephropathy in a subject E88. A kit comprising a container, a composition within the container comprising the recombinant ROBO2 protein of any one of E1-E44, or the pharmaceutical composition of E59 and a package insert containing instructions to administer a therapeutically effective amount of the recombinant ROBO2 protein or the pharmaceutical composition for treatment of a patient in need thereof.

BRIEF DESCRIPTION OF THE DRAWINGS

FIG. 1A is a graphic presentation showing the domains of human ROBO2. The 21-amino acid ROBO2 leader sequence (SEQ ID NO: 17; residues 1-21 according to the numbering set forth in SEQ ID NO: 24) is cleaved during protein production to produce mature ROBO2. Residues 22-859 according to the numbering set forth in SEQ ID NO: 24 form the extracellular domain, residues 860-880 according to the numbering of SEQ ID NO: 24 form the transmembrane domain, and residues 881-1378 according to the numbering of SEQ ID NO: 24 form the cytoplasmic domain. The ROBO2 pre-Ig1sequence (SEQ ID NO: 8), the Ig1-Ig2 inter-domain linker (SEQ ID NO: 10) and the Ig2-Ig3 inter-domain linker (SEQ ID NO: 12) are also shown.

FIG. 1B is a graphic presentation showing exemplary recombinant ROBO2-Fc fusions proteins described herein: ROBO2-Fc. 1.0 (solely contains Ig1 domain, i.e., amino acid residues 31 to 127 according to the numbering of SEQ ID NO: 24), ROBO2-Fc. 1.1 (contains Ig1 domain and Ig1-Ig2 inter-domain linker, i.e., amino acid residues 31 to 132 according to the numbering of SEQ ID NO: 24), ROBO2-Fc. 2.0 (contains Ig1 domain, Ig1-Ig2 inter-domain linker, and Ig2 domain, i.e., amino acid residues 31 to 220 according to the numbering of SEQ ID NO: 24), ROBO2-Fc. 2.1 (contains Ig1 domain, Ig1-Ig2 inter-domain linker, Ig2 domain, and Ig2-Ig3 inter-domain linker, i.e., amino acid residues 31 to 224 according to the numbering of SEQ ID NO: 24), ROBO2-Fc. 2.2 (contains pre-Ig1 sequence, Ig1 domain, Ig1-Ig2 inter-domain linker, Ig2 domain, and Ig2-Ig3 inter-domain linker, i.e., amino acid residues 22 to 224 according to the numbering of SEQ ID NO: 24), ROBO2-Fc. 3.0 (contains Ig1 domain, Ig1-Ig2 inter-domain linker, Ig2 domain, Ig2-Ig3 inter-domain linker, Ig3 domain, i.e., amino acid residues 31 to 309 according to the numbering of SEQ ID NO: 24) and ROBO2-Fc. 4.0 (contains Ig1 domain, Ig1-Ig2 inter-domain linker, Ig2 domain, Ig2-Ig3 inter-domain linker, Ig3 domain, Ig3-Ig4 inter-domain linker and Ig4, i.e., amino acid residues 31 to 409 according to the numbering of SEQ ID NO: 24) described herein.

FIG. 2 shows the ROBO2-Fc 2.2 amino acid sequence (SEQ ID NO: 1). Residues are numbered sequentially starting with the N-terminus. The Ig1 and Ig2 domains are shown in all caps, while the Fc domain is shown in lower case. The pre-Ig1 sequence (SEQ ID NO: 8) and the Ig2-Ig3 inter-domain linker (SEQ ID NO: 12) are shown in bold and italics, while the Ig1-Ig2 inter-domain linker (SEQ ID NO: 10) is shown in italics. The predicted intra- and inter-chain disulfide bonds are illustrated with connecting lines. A single polypeptide chain is shown with disulfide bonds in the Fc hinge region which can dimerize with a second, Fc comprising polypeptide chain. The canonical N-linked glycosylation consensus sequence sites are circled (i.e., NXS/T where the glycan is attached to the asparagine residue and where X can be any amino acid except proline and the third amino acid is either serine or threonine), and the Fc-effector function-null point mutations located at A228, A229, and A231 are shown in bold. The 6-amino acid Gly-Ser linker sequence is shown in the boxed region.

FIGS. 6A-6B demonstrate the dose-dependent inhibition of SLIT2-N binding to cell surface ROBO2 by ROBO2-Fc 2.2 (SEQ ID NO: 1) as assessed by Homogenous Time Resolved Fluorescence (HTRF). An 11-point, 4-fold dose titration of ROBO-Fc 2.2 (black squares) or an isotype control antibody (black circles) was added to either a human SLIT2-N (FIG. 6A) or rat SLIT2-N (FIG. 6B) human ROBO2 HTRF assay. ROBO2-Fc 2.2 was a potent neutralizer of both human SLIT2-N:human ROBO2 ($IC_{50}$ of 7 nM) and rat SLIT2-N:human ROBO2 ($IC_{50}$ of 4 nM) binding.

DETAILED DESCRIPTION OF THE INVENTION

1. Overview

The invention encompasses novel recombinant ROBO2 proteins capable of binding SLIT ligands (for example, the SLIT2 ligand), thereby inhibiting the interaction of SLIT with ROBO2, and consequently, inhibiting the SLIT2-ROBO2 signaling pathway. Previous studies have shown that while both immunoglobulin-like (Ig-like) domains 1 and 2 (Ig1 and Ig2) of ROBO2 interact with SLIT ligands; the first Ig-like domain (Ig1) is the primary binding site for SLIT. In addition, previous studies have indicated that removing the three fibronectin type III (FNIII) repeats has a greater negative effect on ROBO binding to SLIT ligands than removal of the third and fourth immunoglobulin-like domains (Ig3 and Ig4). That is, FNIII deletion causes a greater reduction in ROBO binding to SLIT ligands than deletion of Ig3 and Ig4.

Figure 3:
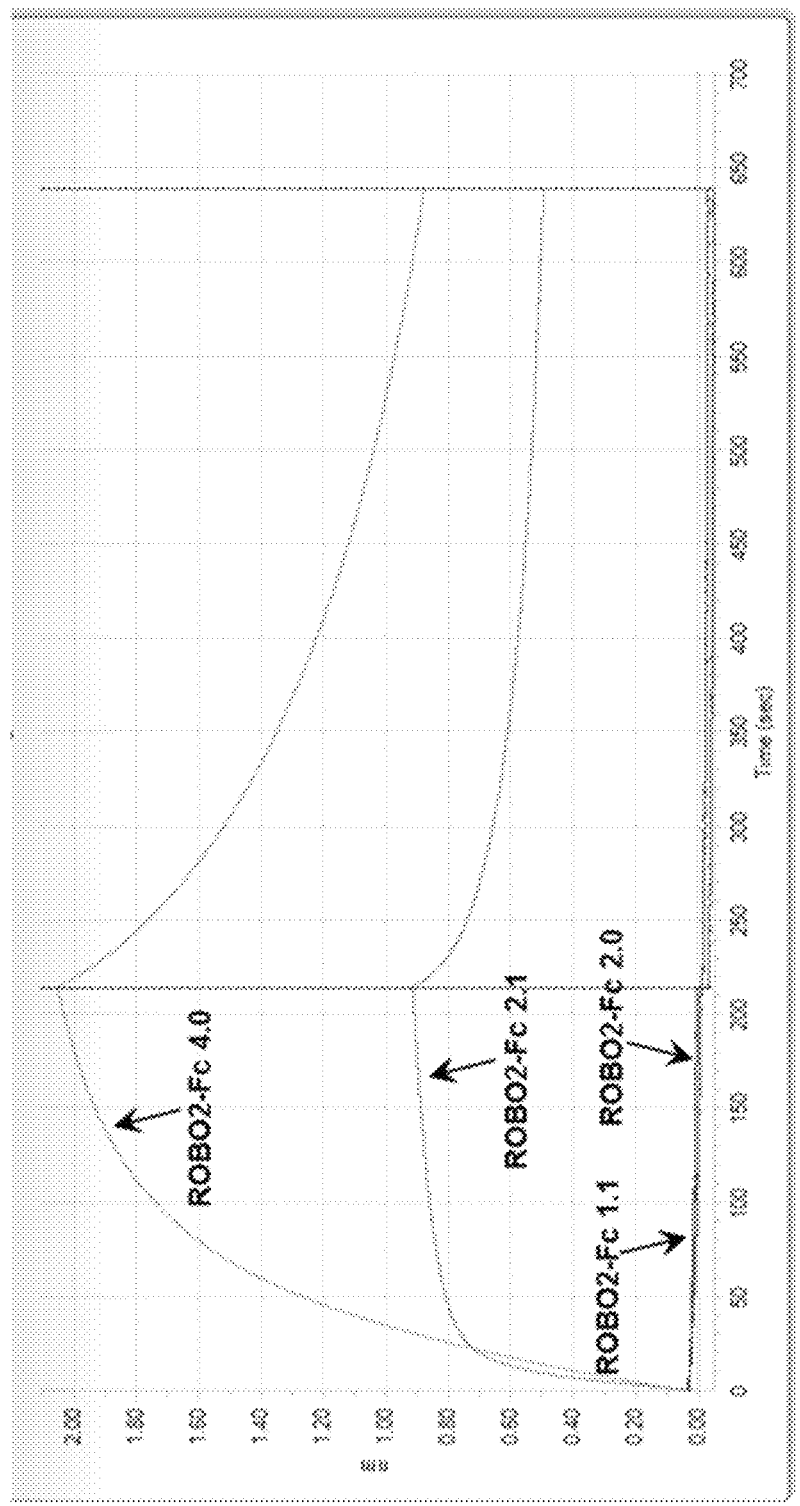
FIG. 3 demonstrates that ROBO2-Fc 2.1 (SEQ ID NO:2) binds to SLIT2 while ROBO2-Fc 1.1 (SEQ ID NO:4) and ROBO2-Fc 2.0 (SEQ ID NO:3) do not. Utilizing the Octet Red ROBO2-Fc proteins were loaded onto anti human-crystallized fragment (AHFc) sensors at 10 µg/ml and incubated with 100 nM SLIT2 for 7 minutes and then the sensors were moved to buffer alone for 640 seconds. ROBO2-Fc 4.0 (SEQ ID NO: 7) was included as a positive control for binding. The addition of the sequence VFER (SEQ ID NO: 12) after the Ig2 domain of ROBO2 to create ROBO2-Fc 2.1 (SEQ ID NO: 2) was essential to produce a ROBO2-Fc fusion protein that binds SLIT2.

Surprisingly, it is now shown for the first time that a construct, ROBO2-Fc 2.1 (SEQ ID NO: 2; FIG. 1B), comprising only the first two immunoglobulin-like domains (Ig1 and Ig2) along with the Ig2-3 inter-domain linker, VFER (SEQ ID NO: 12), and devoid of the three fibronectin type III (FNIII) repeats bound SLIT2 (FIG. 3). In contrast, recombinant ROBO2 proteins lacking the three fibronectin type III (FNIII) repeats but consisting of:
  (i) the Ig1 domain of ROBO2 (ROBO2-Fc 1.1; SEQ ID NO: 4; FIG. 1B),
  (ii) the Ig1 and Ig2 domains of ROBO2 (ROBO2-Fc 2.0; SEQ ID NO: 3; FIG. 1B), or
  (iii) the Ig1, Ig2 and Ig3 domains of ROBO2 (ROBO2-Fc 3.0; SEQ ID NO: 6; FIG. 1B) did not bind SLIT2 (FIG. 3).

Thus, addition of VFER (SEQ ID NO: 12) to the C-terminus of the Ig1-Ig2 domains was required to create a ROBO2-Fc construct (ROBO2-Fc 2.1; SEQ ID NO: 2) with a robust binding profile to SLIT2 in the absence of the FNIII repeats. This ROBO2-Fc 2.1 construct lacks not only the third, fourth and fifth immunoglobulin-like domains (Ig3, Ig4 and Ig5), but is also devoid of the three fibronectin type III (FNIII) repeats. Surprisingly, the difference in binding or not binding SLIT2 was found to be the presence of the four-amino acid VFER sequence (SEQ ID NO: 12).

Figure 4A:
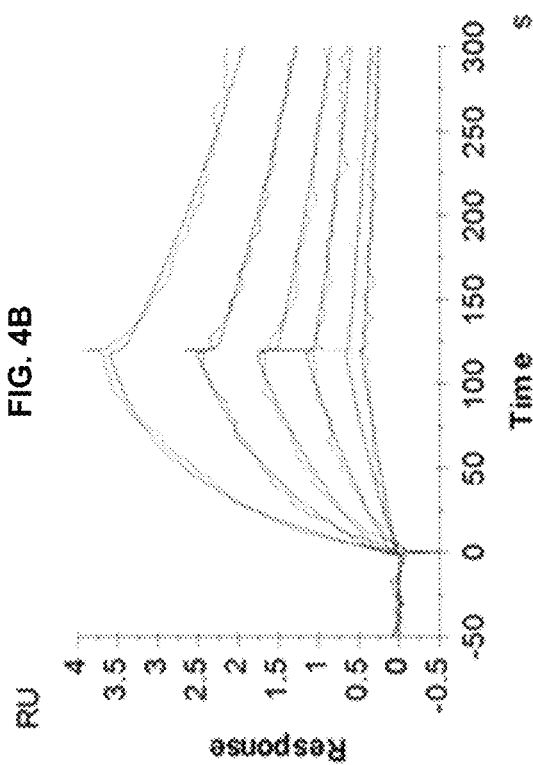
FIGS. 4A-4C demonstrate that ROBO2-Fc 2.2 (SEQ ID NO: 1) binds to SLIT2 with high affinity. $K_D$ values were measured using surface plasmon resonance (SPR). The $K_D$ of ROBO2-Fc 2.2 to human/cynomolgus monkey SLIT2-D2 (ROBO2 binding domain, 100% identical) was 0.293 nM (FIG. 4A). The $K_D$ of ROBO2-Fc 2.2 to human SLIT2-N(N terminal fragment) was 0.279 nM (FIG. 4B), and the $K_D$ of ROBO2-Fc 2.2 to rat SLIT2-N was 0.543 nM (FIG. 4C).
Figure 4B:
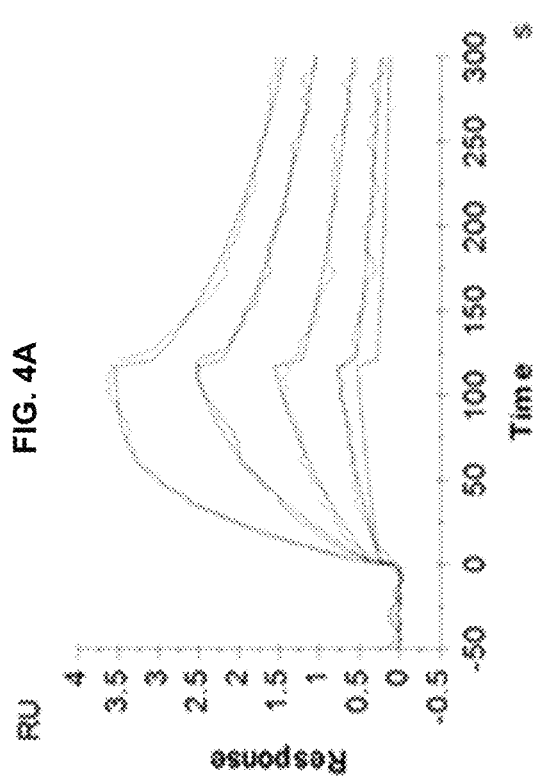
Figure 14:
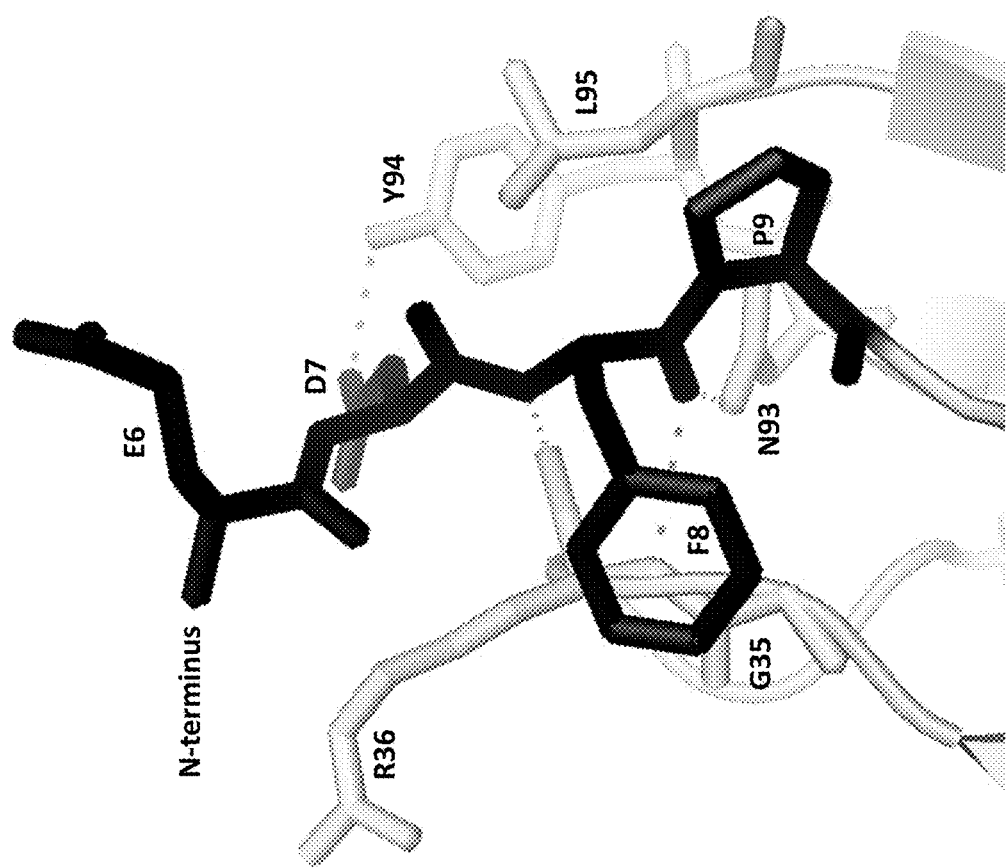
FIG. 14 shows a drawing depicting the crystal structure of a ROBO2-His construct that consists of the ROBO2 pre-Ig1 sequence (SRLRQEDFP; SEQ ID NO: 8), Ig1 domain, Ig2 domain and the ROBO2 Ig2-3 inter-domain linker (VFER; SEQ ID NO: 12) with a 6× histidine tag (His6) (SEQ ID NO: 25) at the C-terminus. The crystal structure of ROBO2-His reveals that that Asp7, Phe8, and Pro9 are substantially involved in the interactions vital for structural integrity of ROBO2's Ig1 domain.

None of the recombinant ROBO2 protein constructs described above contain the ROBO2 pre-Ig1 sequence (SEQ ID NO: 8). It was discovered, surprisingly, that the production of these recombinant ROBO2 proteins, disclosed and exemplified herein, can be dramatically increased by including the ROBO2 pre-Ig1 sequence (SEQ ID NO: 8). Addition of this sequence increased protein production by about 25-fold compared to constructs lacking the sequence while preserving high affinity binding to SLIT2 (FIGS. 3-4A-C). As shown in FIG. 14, this ROBO2 pre-Ig1 sequence bridges together the two β-sheets of ROBO2's Ig1 domain and is believed to stabilize the structural fold of the N-terminal region. Without wishing to be bound by any particular theory, the pre-Ig1 sequence appears to contribute to the enhanced expression of the novel proteins.

2. Definitions

In some aspects, provided herein are recombinant ROBO2 proteins capable of binding SLIT and comprising an immunoglobulin domain.

The term "recombinant protein" refers to a polypeptide which is produced by recombinant DNA techniques, wherein generally, DNA encoding the polypeptide is inserted into a suitable expression vector which, in turn, is introduced into a host cell to produce the recombinant protein. As used herein, "protein" refers to any composition comprising amino acids and recognized as a protein by those of skill in the art. The terms "protein", "peptide" and "polypeptide are used interchangeably herein. Amino acids may be referred to by their complete names (e.g., alanine) or by the accepted one letter (e.g., A), or three letter (e.g., Ala) abbreviations.

As used herein, an "immunoglobulin domain" is a polypeptide derived from an immunoglobulin. In some embodiments, an immunoglobulin domain comprises an immunoglobulin heavy chain or a portion thereof. In some embodiments, the portion of the heavy chain is the crystallizable fragment (Fc) or a portion thereof. As used herein, the Fc fragment comprises the heavy chain hinge region, and the $C_H2$ and $C_H3$ domains of the heavy chain of an immunoglobulin. The heavy chain (or portion thereof) may be derived from any one of the known heavy chain isotypes: IgG (γ), IgM (μ), IgD (δ), IgE (ε), or IgA (α). In addition, the heavy chain (or portion thereof) may be derived from any one of the known heavy chain isotypes or subtypes: IgG1 (γ1), IgG2 (γ2), IgG3 (γ3), IgG4 (γ4), IgA1 (α1), IgA2 (α2). In some embodiments, the immunoglobulin domain comprises an uninterrupted native (i.e., wild-type) sequence of an immunoglobulin. In some embodiments, the immunoglobulin Fc domain comprises a variant Fc region.

For all heavy chain constant region amino acid positions discussed in the present invention, numbering is according to the Eu index first described in Edelman et al., 1969, Proc. Natl. Acad. Sci. USA 63(1):78-85, describing the amino acid sequence of myeloma protein Eu, which is the first human IgG1 sequenced. The Eu index of Edelman et al. is also set forth in Kabat et al., 1991, Sequences of Proteins of Immunological Interest, 5th Ed., United States Public Health Service, National Institutes of Health, Bethesda. Thus, the "EU index as set forth in Kabat" or "EU index of Kabat" refers to the residue numbering system based on the human IgG1 Eu antibody of Edelman et al. as set forth in Kabat 1991.

A "native sequence Fc region" comprises an amino acid sequence identical to the amino acid sequence of an Fc region found in nature. A "variant Fc region" comprises an amino acid sequence which differs from that of a native sequence Fc region by virtue of at least one amino acid modification. Preferably, the variant Fc region has at least one amino acid substitution compared to a native sequence Fc region, e.g., from about one to about ten amino acid substitutions, and preferably, from about one to about five amino acid substitutions compared to a native sequence Fc region. The variant Fc region herein will preferably possess at least about 80% amino acid sequence identity with a native sequence Fc region, and more preferably, at least about 90% amino acid sequence identity therewith, more preferably, at least about 95%, at least about 96%, at least about 97%, at least about 98%, and most preferably at least about 99% amino acid sequence identity therewith.

As used herein a "linker" is a molecule or group of molecules that binds two separate entities (e.g., the extracellular domain and the immunoglobulin domain of a recombinant ROBO2-Fc protein) to one another and can provide spacing and flexibility between the two entities such that they are able to achieve a conformation in which they, e.g., specifically bind their cognate ligand (e.g., SLIT ligand). Protein linkers are particularly preferred, and they may be expressed as a component of the recombinant protein using standard recombinant DNA techniques well-known in the art.

The term "$IC_{50}$" or "the half maximal inhibitory concentration" refers to the concentration of the recombinant ROBO2 protein that is required for 50% inhibition of the ROBO2-SLIT signaling pathway, for example the ROBO2-SLIT2 signaling pathway. $IC_{50}$ is a measure of how much of recombinant ROBO2 protein is needed to inhibit a ROBO2-SLIT biological process by 50%, such as the binding between ROBO2 and a SLIT ligand, binding of intracellular signaling molecules (such as srGAP1 or Nck) to the intracellular domain of ROBO2 and/or downstream activities of ROBO2-SLIT signaling (such as actin polymerization, podocyte adhesion, and/or SLITx-N mediated inhibition of neuronal cell migration). A lower $IC_{50}$ indicates a more potent effect since a smaller amount of the recombinant ROBO2 protein mediates a more potent inhibitory effect.

As used herein, the term "SLITx" refers generally to a SLIT ligand. Similarly, the terms "SLITx-N" and SLITx-C" refer generally to N-terminal and C-terminal fragments, respectively, of SLIT ligands. The SLIT ligand may be a mammalian SLIT ligand, preferably a human SLIT ligand. In some embodiments, the SLIT ligand is selected from the group consisting of a SLIT1 ligand, a SLIT2 ligand, and a SLIT3 ligand. The SLIT ligand may be a SLIT2 ligand, preferably a human SLIT2 ligand.

As used herein, a "subject" is an animal, preferably a mammal, more preferably a non-human primate, and most preferably a human. The terms "subject" "individual" and "patient" are used interchangeably herein. In all embodiments, human nucleic acids and human polypeptides are preferred. It is believed that the results obtained using the human, rat and cynomolgus monkey molecules described elsewhere herein are predictive of the results that may be obtained using other homologous sequences.

As used herein, "treatment" is an approach for obtaining beneficial or desired clinical results. For purposes of this invention, beneficial or desired clinical results include, but are not limited to, one or more of the following: reducing proteinuria (i.e., reducing the amount of protein in the urine compared with the level of protein in urine in the absence of drug administration), reducing edema, and/or restoring blood albumin levels. The term "treatment" includes prophylactic and/or therapeutic treatments. If it is administered prior to clinical manifestation of a condition, the treatment is considered prophylactic. Therapeutic treatment includes, e.g., ameliorating or reducing the severity of a disease, or shortening the length of the disease.

The term "therapeutically effective amount" refers to an amount of a therapeutic agent of this invention effective to "treat" a disease or disorder in a subject. For example, a therapeutically effective amount may be the amount that alleviates one or more symptoms of the disease or the amount necessary to keep a disease in remission. In the case of a focal segmental glomerulosclerosis (FSGS), the therapeutically effective amount refers to that amount which has at least one of the following effects: reducing proteinuria (i.e., reducing the amount of protein in the urine compared with the level of protein in urine in the absence of drug administration), reducing edema, and/or restoring blood albumin levels.

"About" or "approximately" when used in connection with a measurable numerical variable, refers to the indicated value of the variable and to all values of the variable that are within the experimental error of the indicated value (e.g., within the 95% confidence interval for the mean) or ±10% of the indicated value, whichever is greater. Numeric ranges are inclusive of the numbers defining the range.

Binding Affinity

"Binding affinity" generally refers to the strength of the sum total of non-covalent interactions between a contact residue of one binding partner (e.g., the recombinant ROBO2 protein disclosed herein) and a contact residue of its binding partner (e.g., a SLIT ligand). Unless indicated otherwise, as used herein, "binding affinity" refers to binding affinity that reflects a 1:1 interaction between members of a binding pair or binding partners (e.g., the recombinant ROBO2 protein and a SLIT2 ligand).

At its most detailed level, the binding affinity for the interaction between ROBO2 and a SLIT ligand can be defined by the spatial coordinates defining the atomic contacts present in the ROBO2/SLIT interaction, as well as information about their relative contributions to the binding thermodynamics. At one level, a contact residue can be characterized by the spatial coordinates defining the atomic contacts between ROBO2 and SLIT. In one aspect, the contact residue can be defined by a specific criterion, e.g., distance between atoms in the ROBO2 protein amino acid residue and the atoms in the SLIT protein amino acid residue (e.g., a distance of equal to or less than about 4 Å (such as 3.8 Å used in the Examples here) from a heavy atom of a ROBO2 amino acid residue and a heavy atom of an amino acid residue of SLIT. In another aspect, a contact residue can be characterized as participating in a hydrogen bond interaction with the cognate binding partner, or with a water molecule that is also hydrogen bonded to the binding partner (i.e., water-mediated hydrogen bonding). In another aspect, a contact residue can be characterized as forming a salt bridge with a residue of the binding partner. In yet another aspect, a contact residue can be characterized as a residue having a non-zero change in buried surface area (BSA) due to interaction with a contact residue of the binding partner. At a less detailed level, the binding affinity can be characterized through function, e.g., by competition binding with other proteins.

Low-affinity recombinant proteins generally bind their ligands slowly and tend to dissociate readily, whereas high-affinity recombinant proteins generally bind their ligands faster and tend to remain bound longer. A variety of methods of measuring binding affinity are known in the art, any of which can be used for purposes of the present invention. Specific illustrative and exemplary embodiments for measuring binding affinity are described in the following.

The binding affinity can be expressed as $K_D$ value, which refers to the dissociation rate of a particular recombinant ROBO2 protein-SLIT ligand interaction. $K_D$ is the ratio of the rate of dissociation, also called the "off-rate ($k_{off}$)", to the association rate, or "on-rate ($k_{on}$)". Thus, $K_D$ equals $k_{off}/k_{on}$ and is expressed as a molar concentration (M), and the smaller the $K_D$, the stronger the affinity of binding. $K_D$ values can be determined using methods well established in the art. One exemplary method for measuring $K_D$ is surface plasmon resonance (SPR), a method well-known in the art (e.g., Nguyen et al. Sensors (Basel). 2015 May 5; 15(5): 10481-510). $K_D$ value may be measured by SPR using a biosensor system such as a BIACORE® system. BIAcore kinetic analysis comprises analyzing the binding and dissociation of an antigen from chips with immobilized molecules (e.g. molecules comprising epitope binding domains), on their surface. Another well-known method in the art for determining the $K_D$ of a protein is by using Bio-Layer Interferometry (e.g., Shah et al. J Vis Exp. 2014; (84): 51383). $K_D$ value may be measured using OCTET® technology (Octet QKe system, ForteBio). Alternatively or in addition, a KinExA® (Kinetic Exclusion Assay) assay, available from Sapidyne Instruments (Boise, Id.) can also be used. Any method known in the art for assessing the binding affinity between two binding partners is encompassed herein.

3. Recombinant ROBO2 Proteins

In some aspects, the instant disclosure provides recombinant ROBO2 proteins. In some embodiments, the recombinant ROBO2 proteins disclosed herein bind SLIT ligands (in particular, SLIT2 ligand), thereby preventing the binding of SLIT to cellular ROBO2 receptors, and are hence referred to as SLIT neutralizing ligand traps. Surprisingly, as shown in the Examples, a construct, ROBO2-Fc 2.1 (SEQ ID NO: 2; FIG. 1B), comprising the first two immunoglobulin-like domains (Ig1 and Ig2), Ig1-Ig2 inter-domain linker, along with the Ig2-3 inter-domain linker, VFER (SEQ ID NO: 12), and devoid of the three fibronectin type III (FNIII) repeats bound SLIT2 (FIG. 3). Crystal structure studies also show that the inclusion of the ROBO2 Ig2-Ig3 inter-domain linker, VFER (V200-F201-E202-R203; SEQ ID NO: 12) effectively stabilizes the structural fold in the C-terminal region of ROBO2's second Ig domain FIG. 15), and notably increases the expression level of the recombinant ROBO2 protein.

In some aspects, the instant disclosure provides recombinant polypeptides comprising a SLIT-binding moiety and a half-life extending moiety. The "SLIT-binding moiety" confers SLIT-binding ability to the recombinant ROBO2 protein. In some embodiments, the SLIT-binding moiety comprises a portion of a ROBO2 extracellular domain. In some embodiments, the portion of the ROBO2 extracellular domain comprises at least two immunoglobulin-like (Ig-like) domains, and a C-terminus sequence consisting of VFER (SEQ ID NO: 12). In some embodiments, the at least two Ig-like domains are selected from the group consisting of Ig1, Ig2, Ig3, Ig4 and Ig5. In some embodiments, the at least two Ig-like domains are selected from the group consisting of the sequence of SEQ ID NO: 9, SEQ ID NO: 11, SEQ ID NO: 13 and SEQ ID NO: 14. In some embodiments, the portion of the ROBO2 extracellular domain comprises the first two Ig-like domains (Ig1 and Ig2) of ROBO2, In some embodiments, the portion of the ROBO2 extracellular domain comprises SEQ ID NO: 9 and/or SEQ ID NO: 11.

Figure 4C:
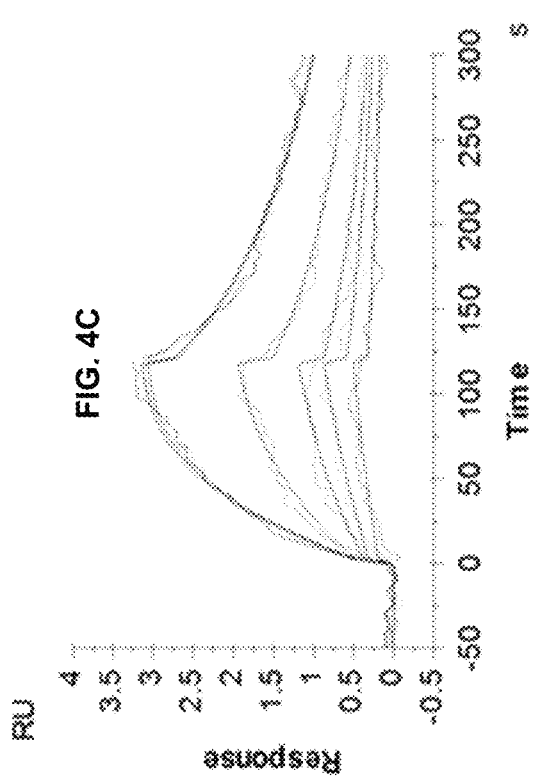
Figure 5:
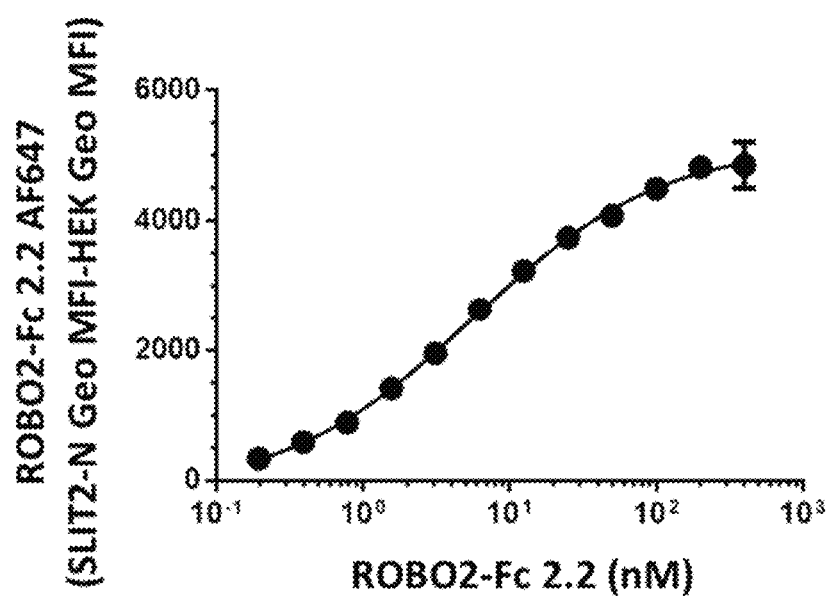
FIG. 5 demonstrates that ROBO2-Fc 2.2 (SEQ ID NO: 1) binds with high affinity having an $EC_{50}$ of 9 nM to human SLIT2-N that is overexpressed on human embryonic kidney (HEK293) cells. A 12-point, 2-fold dilution series of ROBO2-Fc 2.2 labeled with Alexa Fluor 647 (AF647) was incubated with either SLIT2-N expressing HEK293 cells or control HEK293 cells. The data are presented as the geometric mean fluorescence intensity (Geo MFI) of ROBO2-Fc 2.2 AF647 on SLIT2-N HEK293 cells minus the geometric mean fluorescence intensity of ROBO2-Fc 2.2 AF647 on control HEK293 cells.

Protein production studies also determined that the production of the recombinant ROBO2 proteins, disclosed and exemplified herein, can be dramatically increased by including the ROBO2 pre-Ig1 sequence (SEQ ID NO: 8). Addition of this sequence increases protein production in transiently and/or stably transfected mammalian cells by about 25-fold while preserving high affinity binding to SLIT (FIGS. 3-5).

Accordingly, in some embodiments, the portion of the ROBO2 extracellular domain further comprises the ROBO2 pre-Ig1 sequence. In some embodiments, the ROBO2 pre-Ig1 sequence comprises SEQ ID NO: 8.

In some embodiments, the portion of the ROBO2 extracellular domain comprises ROBO2 pre-Ig1 sequence, Ig1, Ig1-Ig2 inter-domain linker, Ig2, and Ig2-Ig3 inter-domain linker. Exemplary sequences of the ROBO2 pre-Ig1 sequence (SEQ ID NO: 8), Ig1 (SEQ ID NO: 9), Ig1-Ig2 inter-domain linker (SEQ ID NO: 10), Ig2 (SEQ ID NO: 11), and Ig2-Ig3 inter-domain linker (SEQ ID NO: 12) are shown in Table 23 and also illustrated in FIG. 2. The present invention is not limited to the sequences disclosed herein. Corresponding residues from other ROBO2 homologs, isoforms, variants, or fragments can be identified according to sequence alignment or structural alignment that is known in the art. For example, alignments can be done by hand or by using well-known sequence alignment programs such as ClustalW2, or "BLAST 2 Sequences" using default parameters.

In some embodiments, the portion of the ROBO2 extracellular domain comprises amino acid residues 1 to 203 according to the numbering of SEQ ID NO: 1. In some embodiments, the recombinant ROBO2 protein comprises a portion of the ROBO2 extracellular domain that shares at least 90%, at least 91%, at least 92%, at least 93%, at least 94%, at least 95%, at least 96%, at least 97%, at least 98%, or at least 99% identity to amino acid residues 1 to 203 according to the numbering of SEQ ID NO: 1. In some embodiments, the recombinant ROBO2 protein comprises an extracellular domain consisting of amino acid residues 1 to 203 according to the numbering of SEQ ID NO: 1.

In some aspects, the ROBO2 is human ROBO2. In some aspects, the ROBO2 is rat ROBO2. In some aspects, the ROBO2 is mouse ROBO2. In some aspects, the ROBO2 is primate ROBO2. In some aspects, the ROBO2 is ape ROBO2. In some aspects, the ROBO2 is monkey ROBO2. In some aspects, the ROBO2 is cynomologus monkey ROBO2.

In addition to the SLIT-binding moiety, the novel, recombinant ROBO2 proteins comprise a half-life extending moiety. The "half-life extending moiety" extends the serum half-life in vivo of the recombinant ROBO2 protein compared to the same ROBO2 protein without the half-life extending moiety. Examples of half-life extending moieties include, but are not limited to, polyhistidine, Glu-Glu, glutathione S transferase (GST), thioredoxin, protein A, protein G, an immunoglobulin domain, maltose binding protein (MBP), human serum albumin (HSA), or polyethylene glycol (PEG). In some embodiments, the half-life extending moiety comprises an immunoglobulin domain. In some embodiments, the immunoglobulin domain comprises an Fc domain. In some embodiments, the Fc domain is derived from any one of the known heavy chain isotypes: IgG ($\gamma$), IgM ($\mu$), IgD ($\delta$), IgE ($\epsilon$), or IgA ($\alpha$). In some embodiments, the Fc domain is derived from any one of the known heavy chain isotypes or subtypes: $IgG_1$ ($\gamma$1), $IgG_2$ ($\gamma$2), $IgG_3$ ($\gamma$3), $IgG_4$ ($\gamma$4), $IgA_1$ ($\alpha$1), $IgA_2$ ($\alpha$2). In some embodiments, the Fc domain is the Fc domain of human $IgG_1$.

In some embodiments, the Fc domain comprises an uninterrupted native sequence (i.e., wild type sequence) of a Fc domain. In some embodiments, the immunoglobulin Fc domain comprises a variant Fc domain resulting in altered biological activity. For example, at least one point mutation or deletion may be introduced into the Fc domain so as to reduce or eliminate the effector activity (e.g., WO 2005/063815), and/or to increase the homogeneity during the production of the recombinant protein. In some embodiments, the Fc domain is the Fc domain of human $IgG_1$ and comprises one or more of the following effector-null substitutions: L234A, L235A, and G237A (Eu numbering) or L228A, L229A and G231A relative to the numbering of SEQ ID NO: 1. In some embodiments, the Fc domain does not comprise the lysine located at the C-terminal position of human IgG1 (i.e., K447 by Eu numbering). The absence of the lysine may increase homogeneity during the production of the recombinant protein. In some embodiments, the Fc domain comprises the lysine located at the C-terminal position (K447, Eu numbering).

In some embodiments, the recombinant ROBO2 polypeptide comprises one, two, three or four intra-chain disulfide bonds which may be located in the ROBO2 extracellular domain or in the Fc domain. In some embodiments, the recombinant ROBO2 polypeptide comprises four intra-chain disulfide bonds, two of which are located in the ROBO2 extracellular domain and two are located in the Fc domain. In some embodiments, the intra-chain disulfide bonds located in the ROBO2 extracellular domain are between Cys31 and Cys89, and between Cys133 and Cys182, all according to the numbering of SEQ ID NO: 1. In some embodiments, the intra-chain disulfide bonds located in the Fc domain are between Cys255 and Cys315, and between Cys361 and Cys419 all according to the numbering of SEQ ID NO: 1.

In some embodiments, two of the recombinant ROBO2 polypeptides associate, either covalently, for example, by a disulfide bond, a polypeptide bond or a crosslinking agent, or non-covalently, to produce a homodimeric protein. In some embodiments, two recombinant ROBO2 polypeptides are associated covalently to form a homodimer by means of at least one, and more preferably, two inter-chain disulfide bonds via cysteine residues, preferably located within the immunoglobulin Fc region of each polypeptide. In some embodiments, the two inter-chain disulfide bonds are between Cys220 and Cys223. In some embodiments, less than 90%, less than 80%, less than 70%, less than 60%, less than 50%, less than 40%, less than 30%, less than 20%, less than 10%, less than 8%, less than 5%, less than 4%, less than 2%, less than 1% of the recombinant ROBO2 polypeptides are associated to form a homodimer.

In some embodiments, a recombinant ROBO2 polypeptide associates with another polypeptide, either covalently, for example, by a disulfide bond, a polypeptide bond or a crosslinking agent, or non-covalently, to produce a heterodimeric protein. In some embodiments, the heterodimeric protein is bispecific or multispecific. In some embodiments the other polypeptide comprises an immunoglobulin domain. In some embodiments, the polypeptides are associated covalently to form a heterodimer by means of at least one, and more preferably, two inter-chain disulfide bonds via cysteine residues, preferably located within the immunoglobulin Fc region of each polypeptide. In some embodiments, the two inter-chain disulfide bonds are between Cys220 and Cys223 of the recombinant ROBO2 polypeptide. In some embodiments, the heterodimeric protein comprises two different recombinant ROBO2 polypeptides.

In some embodiments, the Fc domain of the recombinant ROBO2 protein comprises amino acid residues 210 to 440 according to the numbering of SEQ ID NO: 1. In some embodiments, the recombinant ROBO2 protein comprises a Fc domain sharing at least 90%, at least 91%, at least 92%, at least 93%, at least 94%, at least 95%, at least 96%, at least 97%, at least 98%, or at least 99% amino acid sequence identity to amino acid residues 210 to 440 according to the numbering of SEQ ID NO: 1. In some embodiments, the recombinant ROBO2 protein comprises a Fc domain consisting of amino acid residues 210 to 440 of according to the numbering SEQ ID NO: 1.

In some embodiments, the extracellular domain of the recombinant ROBO2 protein is contiguous with the immunoglobulin domain. That is, the last C-terminal amino acid residue of the extracellular domain of the ROBO2 protein is covalently linked by a peptidyl bond with the first N-terminal amino acid residue of the immunoglobulin domain. In some embodiments, the extracellular domain of the recombinant ROBO2 protein is connected via a linker to the immunoglobulin domain. In some embodiments, the linker is a peptidyl linker. In some embodiments, the peptidyl linker comprises about 1 to 30 amino acid residues. In some embodiments, the peptidyl linker is selected from the group consisting of a glycine rich peptide; a peptide comprising glycine and serine; a peptide having a sequence [Gly-Gly-Ser]$_n$, wherein n is 1, 2, 3, 4, 5, or 6 (SEQ ID NO: 22); and a peptide having a sequence [Gly-Gly-Gly-Gly-Ser]$_n$, wherein n is 1, 2, 3, 4, 5, or 6 (SEQ ID NO: 23). In some embodiments, the peptidyl linker is Gly-Gly-Ser-Gly-Gly-Ser (SEQ ID NO: 15). A glycine rich peptide linker comprises a peptide linker, wherein at least 25% of the residues are glycine. Glycine rich peptide linkers are well known in the art (e.g., Chichili et al. Protein Sci. 2013 February; 22(2): 153-167).

In some embodiments, the recombinant ROBO2-Fc protein comprises the sequence of SEQ ID NO: 1. In some embodiments, the recombinant ROBO2-Fc protein consists of the sequence of SEQ ID NO: 1. In some embodiments, the recombinant ROBO2-Fc protein comprises an amino acid sequence having at least 90%, at least 91%, at least 92%, at least 93%, at least 94%, at least 95%, at least 96%, at least 97%, at least 98%, or at least 99% identity to the sequence of SEQ ID NO: 1. In some embodiments, the recombinant ROBO2-Fc protein comprises an amino acid sequence having at least 95% identity to the sequence of SEQ ID NO: 1. In some embodiments, the recombinant ROBO2-Fc protein comprises an amino acid sequence having at least 96% identity to the sequence of SEQ ID NO: 1. In some embodiments, the recombinant ROBO2-Fc protein comprises an amino acid sequence having at least 97% identity to the sequence of SEQ ID NO: 1. In some embodiments, the recombinant ROBO2-Fc protein comprises an amino acid sequence having at least 98% identity to the sequence of SEQ ID NO: 1. In some embodiments, the recombinant ROBO2-Fc protein comprises an amino acid sequence having at least 99% identity to the sequence of SEQ ID NO: 1.

In some embodiments, no more than 10, no more than 9, no more than 8, no more than 7, no more than 6, no more than 5, no more than 4, no more than 3, no more than 2, or no more than 1 substitution is made relative to the sequence of SEQ ID NO: 1. In some embodiments, no more than 5 substitutions are made relative to the sequence of SEQ ID NO: 1. In some embodiments, no more than 4 substitutions are made relative to the sequence of SEQ ID NO: 1. In some embodiments, no more than 3 substitutions are made relative to the sequence of SEQ ID NO: 1. In some embodiments, no more than 2 substitutions are made relative to the sequence of SEQ ID NO: 1. In some embodiments, no more than 1 substitution is made relative to the sequence of SEQ ID NO: 1. In some embodiments, the substitution(s) do not change the $K_D$ by more than 1000-fold, more than 100-fold, or 10-fold compared to the $K_D$ of the protein comprising the sequence of SEQ ID NO: 1. In certain embodiments, the substitution is a conservative substitution according to Table 1.

TABLE 1

Amino Acid Substitutions

| Original Residue | Conservative Substitutions | Exemplary Substitutions |
|---|---|---|
| Ala (A) | Val | Val; Leu; Ile |
| Arg (R) | Lys | Lys; Gln; Asn |
| Asn (N) | Gln | Gln; His; Asp, Lys; Arg |
| Asp (D) | Glu | Glu; Asn |
| Cys (C) | Ser | Ser; Ala |
| Gln (Q) | Asn | Asn; Glu |
| Glu (E) | Asp | Asp; Gln |
| Gly (G) | Ala | Ala |
| His (H) | Arg | Asn; Gln; Lys; Arg |
| Ile (I) | Leu | Leu; Val; Met; Ala; Phe; Norleucine |
| Leu (L) | Ile | Norleucine; Ile; Val; Met; Ala; Phe |
| Lys (K) | Arg | Arg; Gln; Asn |
| Met (M) | Leu | Leu; Phe; Ile |
| Phe (F) | Tyr | Leu; Val; Ile; Ala; Tyr |
| Pro (P) | Ala | Ala |
| Ser (S) | Thr | Thr |
| Thr (T) | Ser | Ser |
| Trp (W) | Tyr | Tyr; Phe |
| Tyr(Y) | Phe | Trp; Phe; Thr; Ser |
| Val (V) | Leu | Ile; Leu; Met; Phe; Ala; Norleucine |

In some embodiments, one of more of the ROBO2 amino acid residues listed in Tables 4-15 are not substituted (for example, E6, D7, F8, P9, V200, F201, E202, R203 each numbered relative to SEQ ID NO: 1). In some embodiments, none of the amino acid resides listed in Tables 4-15 (for example, E6, D7, F8, P9, V200, F201, E202, R203 numbered relative to SEQ ID NO: 1) are substituted. ROBO2 amino acid residues disclosed in Tables 4-15 are amino acid residues believed to be important for supporting the structural integrity of the SLIT-binding domain, according to the crystal structure study (see Example 5). Amino acid substitutions at these positions could potentially affect SLIT binding. Accordingly, it may be desirable that the substitution does not occur at these positions. In some embodiments, the recombinant ROBO2 protein comprises a portion of the ROBO2 extracellular domain that shares at least 90%, at least 91%, at least 92%, at least 93%, at least 94%, at least 95%, at least 96%, at least 97%, at least 98%, or at least 99% identity to the amino acid residues 1 to 203 of the sequence set forth in SEQ ID NO: 1, and further comprises one or more residues E6, D7, F8, P9, V200, F201, E202, and R203 (numbering according to the sequence of SEQ ID NO:1).

Figure 11:
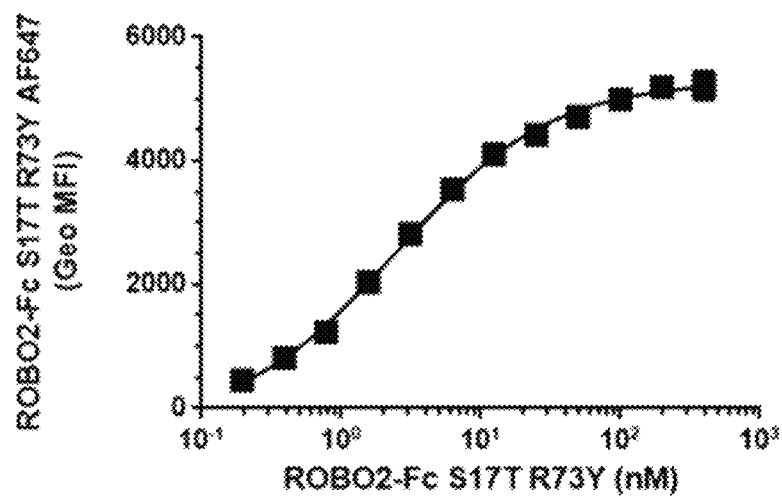
FIG. 11 demonstrates that ROBO2-Fc S17T/R73Y binds to human SLIT2-N overexpressed on human embryonic kidney (HEK293) cells with high affinity having an $EC_{50}$ of 2.5 nM. A 12-point, 2-fold dilution series of ROBO2-Fc S17T/R73Y labeled with alexa fluor 647 (AF647) was incubated with either SLIT2-N expressing HEK293 cells or control HEK293 cells. The data are presented as the geometric mean fluorescence intensity (Geo MFI) of ROBO2-Fc S17T/R73Y AF647 on SLIT2-N HEK293 cells minus the geometric mean fluorescence intensity of ROBO2-Fc S17T/R73Y AF647 on control HEK293 cells.
Figure 12:
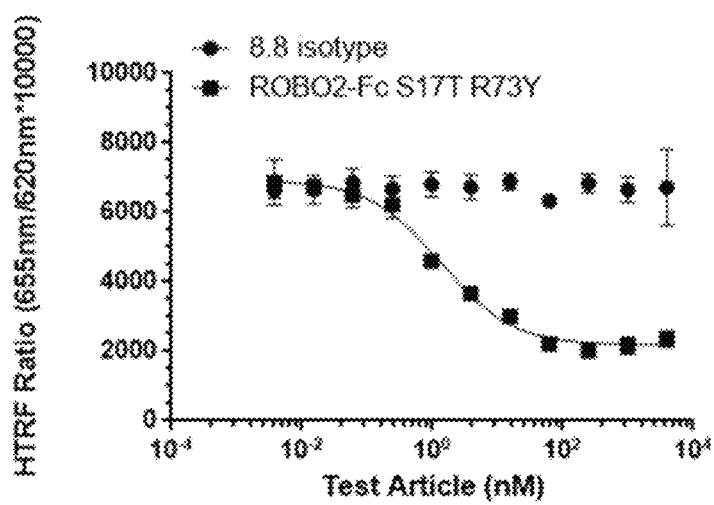
FIG. 12 demonstrates the dose-dependent inhibition of SLIT2-N binding to cell surface ROBO2 by ROBO2-Fc S17T/R73Y as assessed by Homogenous Time Resolved Fluorescence (HTRF). An 11-point, 4-fold dose titration of ROBO2-Fc S17T/R73Y (black squares) or an isotype control antibody (black circles) was added to a human SLIT2-N human ROBO2 HTRF assay. ROBO2-Fc S17T/R73Y was a potent neutralizer of human SLIT2-N:human ROBO2 binding with an $IC_{50}$ of 1.4 nM.
Figure 13:
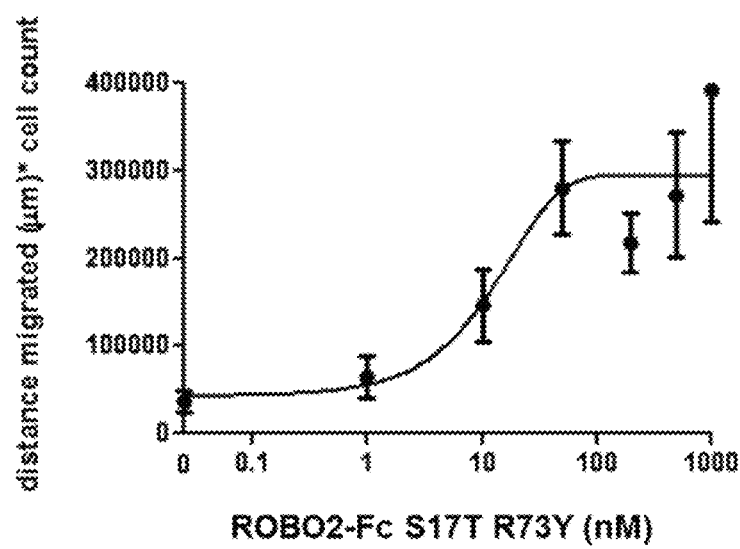
FIG. 13 depicts the dose-dependent inhibition of SLIT2-N mediated inhibition of neuronal cell migration by ROBO2-Fc S17T/R73Y. Subventricular zone (SVZ) neuronal tissue cell explants were cultured overnight in the presence of 1 nM SLIT2-N and titrated amounts of ROBO2-Fc S17T/R73Y. ROBO2-Fc S17T/R73Y was able to restore neuronal cell migration in a dose-dependent manner with an $IC_{50}$ of 11.5 nM.

In some aspects, one or more point mutations relative to the sequence of SEQ ID NO: 1 may be introduced to increase the affinity of the recombinant ROBO2 protein to a SLIT ligand, e.g., SLIT2. As shown in the Examples, the binding affinity to SLIT2 can be increased by about 10-fold by introducing point mutations S17T and R73Y relative to the sequence of SEQ ID NO: 1 (FIGS. 11-13). Accordingly, in some aspects, the instant disclosure provides a recombinant ROBO2 protein having one or more of the following mutations: S17T and R73Y relative to the sequence of SEQ ID NO: 1. In some embodiments, the recombinant ROBO2 protein comprises the sequence set forth in SEQ ID NO: 19.

In some embodiments, the recombinant ROBO2 protein consists of the sequence set forth SEQ ID NO: 19. In some embodiments, the recombinant ROBO2 protein does not comprise the C-terminal lysine located at amino acid residue 441 according to the numbering of SEQ ID NO: 19. In certain embodiments, the recombinant ROBO2 proteins of the invention have a $K_D$ of not more than about $1 \times 10^{-6}$ M, such as not more than about $1 \times 10^{-7}$ M, not more than about $9 \times 10^{-8}$ M, not more than about $8 \times 10^{-8}$ M, not more than about $7 \times 10^{-8}$ M, not more than about $6 \times 10^{-8}$ M, not more than about $5 \times 10^{-8}$ M, not more than about $4 \times 10^{-8}$ M, not more than about $3 \times 10^{-8}$ M, not more than about $2 \times 10^{-8}$ M, not more than about $1 \times 10^{-8}$ M, not more than about $9 \times 10^{-9}$ M, not more than about $8 \times 10^{-9}$ M, not more than about $7 \times 10^{-9}$ M, not more than about $6 \times 10^{-9}$ M, not more than about $5 \times 10^{-9}$ M, not more than about $4 \times 10^{-9}$ M, not more than about $3 \times 10^{-9}$ M, not more than about $2 \times 10^{-9}$ M, not more than about $1 \times 10^{-9}$ M, not more than about $9 \times 10^{-10}$ M, not more than about $8 \times 10^{-10}$ M, not more than about $7 \times 10^{-10}$ M, not more than about $6 \times 10^{-10}$ M, not more than about $5 \times 10^{-10}$ M, not more than about $4 \times 10^{-10}$ M, not more than about $3 \times 10^{-10}$ M, not more than about $2 \times 10^{-10}$ M, not more than about $1 \times 10^{-10}$ M, not more than about $9 \times 10^{-11}$ M, not more than about $8 \times 10^{-11}$ M, not more than about $7 \times 10^{-11}$ M, not more than about $6 \times 10^{-11}$ M, not more than about $5 \times 10^{-11}$ M, not more than about $4 \times 10^{-11}$ M, not more than about $3 \times 10^{-11}$ M, not more than about $2 \times 10^{-11}$ M, not more than about $1 \times 10^{-11}$ M, not more than about $9 \times 10^{-12}$ M, not more than about $8 \times 10^{-12}$ M, not more than about $7 \times 10^{-12}$ M, not more than about $6 \times 10^{-12}$ M, not more than about $5 \times 10^{-12}$ M, not more than about $4 \times 10^{-12}$ M, not more than about $3 \times 10^{-12}$ M, not more than about $2 \times 10^{-12}$ M, not more than about $1 \times 10^{-12}$ M, not more than about $9 \times 10^{-13}$ M, not more than about $8 \times 10^{-13}$ M, not more than about $7 \times 10^{-13}$ M, not more than about $6 \times 10^{-13}$ M, not more than about $5 \times 10^{-13}$ M, not more than about $4 \times 10^{-13}$ M, not more than about $3 \times 10^{-13}$ M, not more than about $2 \times 10^{-13}$ M, not more than about $1 \times 10^{-13}$ M.

In certain embodiments, the recombinant ROBO2 proteins of the invention have a $K_D$ ranging from about $1 \times 10^{-7}$ M to about $1 \times 10^{-14}$ M, from about $9 \times 10^{-8}$ M to about $1 \times 10^{-14}$ M, from about $8 \times 10^{-8}$ M to about $1 \times 10^{-14}$ M, from about $7 \times 10^{-8}$ M to about $1 \times 10^{-14}$ M, from about $6 \times 10^{-8}$ M to about $1 \times 10^{-14}$ M, from about $5 \times 10^{-8}$ M to about $1 \times 10^{-14}$ M, from about $4 \times 10^{-8}$ M to about $1 \times 10^{-14}$ M, from about $3 \times 10^{-8}$ M to about $1 \times 10^{-14}$ M, from about $2 \times 10^{-8}$ M to about $1 \times 10^{-14}$ M, from about $1 \times 10^{-8}$ M to about $1 \times 10^{-14}$ M, from about $9 \times 10^{-9}$ M to about $1 \times 10^{-14}$ M, from about $8 \times 10^{-9}$ M to about $1 \times 10^{-14}$ M, from about $7 \times 10^{-9}$ M to about $1 \times 10^{-14}$ M, from about $6 \times 10^{-9}$ M to about $1 \times 10^{-14}$ M, from about $5 \times 10^{-9}$ M to about $1 \times 10^{-14}$ M, from about $4 \times 10^{-9}$ M to about $1 \times 10^{-14}$ M, from about $3 \times 10^{-9}$ M to about $1 \times 10^{-14}$ M, from about $2 \times 10^{-9}$ M to about $1 \times 10^{-14}$ M, from about $1 \times 10^{-9}$ M to about $1 \times 10^{-14}$ M, from about $1 \times 10^{-7}$ M to about $1 \times 10^{-13}$ M, from about $9 \times 10^{-8}$ M to about $1 \times 10^{-13}$ M, from about $8 \times 10^{-8}$ M to about $1 \times 10^{-13}$ M, from about $7 \times 10^{-8}$ M to about $1 \times 10^{-13}$ M, from about $6 \times 10^{-8}$ M to about $1 \times 10^{-13}$ M, from about $5 \times 10^{-8}$ M to about $1 \times 10^{-13}$ M, from about $4 \times 10^{-8}$ M to about $1 \times 10^{-13}$ M, from about $3 \times 10^{-8}$ M to about $1 \times 10^{-13}$ M, from about $2 \times 10^{-8}$ M to about $1 \times 10^{-13}$ M, from about $1 \times 10^{-8}$ M to about $1 \times 10^{-13}$ M, from about $9 \times 10^{-9}$ M to about $1 \times 10^{-13}$ M, from about $8 \times 10^{-9}$ M to about $1 \times 10^{-13}$ M, from about $7 \times 10^{-9}$ M to about $1 \times 10^{-13}$ M, from about $6 \times 10^{-9}$ M to about $1 \times 10^{-13}$ M, from about $5 \times 10^{-9}$ M to about $1 \times 10^{-13}$ M, from about $4 \times 10^{-9}$ M to about $1 \times 10^{-13}$ M, from about $3 \times 10^{-9}$ M to about $1 \times 10^{-13}$ M, from about $2 \times 10^{-9}$ M to about $1 \times 10^{-13}$ M, or from about $1 \times 10^{-9}$ M to about $1 \times 10^{-13}$ M.

In some embodiments, the recombinant ROBO2 protein binds SLIT2 with a $K_D$ of or less than: about 10 nM, about 5 nM, about 2 nM, about 1 nM, about 900 pM, about 800 pM, about 700 pM, about 600 pM, about 500 pM, about 400 pM, about 300 pM, about 250 pM, about 200 pM, about 150 pM, about 100 pM, about 50 pM, about 40 pM, about 30 pM, about 25 pM, about 20 pM, about 15 pM, about 10 pM, about 5 pM, or about 1 pM. In some embodiments, the recombinant ROBO2 protein binds SLIT2 with a $K_D$ of about 600 pM. In some embodiments, the recombinant ROBO2 protein binds SLIT2 with a $K_D$ of about 500 pM. In some embodiments, the recombinant ROBO2 protein binds SLIT2 with a $K_D$ of about 400 pM. In some embodiments, the recombinant ROBO2 protein binds SLIT2 with a $K_D$ of about 300 pM. In some embodiments, the recombinant ROBO2 protein binds SLIT2 with a $K_D$ of about 250 pM. In some embodiments, the recombinant ROBO2 protein binds SLIT2 with a $K_D$ of about 200 pM.

In general, a recombinant ROBO2-Fc protein should bind to a SLIT ligand (e.g., SLIT2) with high affinity, in order to effectively block the activities of ROBO2. It is desirable that the recombinant ROBO2-Fc protein have binding affinities ($K_D$) in low nanomolar and picomolar range, such as about $1 \times 10^{-8}$ M or lower.

In some embodiments, the recombinant ROBO-Fc protein binds SLIT2 with a $K_D$ that is at least about 2-fold, about 4-fold, about 6-fold, about 8-fold, about 10-fold, about 20-fold, about 40-fold, about 60-fold, about 80-fold, about 100-fold, about 120-fold, about 140-fold, about 160-fold, lower than the $K_D$ value for binding of ROBO1 to SLIT2. In some embodiments, the recombinant ROBO2-Fc protein binds SLIT2 with a $K_D$ that is at least about 2-fold, about 4-fold, about 6-fold, about 8-fold, about 10-fold, about 20-fold, about 40-fold, about 60-fold, about 80-fold, about 100-fold, about 120-fold, about 140-fold, about 160-fold, lower than the $K_D$ value for binding of a ROBO1-Fc protein to SLIT2.

Biological Activity Assays

In certain embodiments, the recombinant ROBO2-Fc protein disclosed herein reduces at least one biological activity of ROBO2-SLIT signaling. Such activity includes, but is not limited to, binding between ROBO2 and SLIT ligand, binding of intracellular signaling molecules (such as srGAP1 or Nck) to the intracellular domain of ROBO2, and/or downstream activities of ROBO2-SLIT signaling, such as, actin polymerization, podocyte adhesion, and/or SLIT2-N mediated inhibition of neuronal cell migration, among other ROBO2-SLIT activities known in the art. Whether a recombinant ROBO2-Fc protein reduces an activity of ROBO2 can be assessed by a number of assays well known in the art. For example, assays known in the art can be used to determine whether the recombinant ROBO2-Fc protein: (a) inhibits the binding of SLIT to ROBO2; (b) reduces the binding of srGAP1 and ROBO2; (c) reduces the binding of Nck and ROBO2; (d) inhibits ROBO2-dependent SLIT2-N activity; (e) inhibits actin polymerization; (f) inhibits podocyte adhesion; and/or (g) inhibits SLIT2-N mediated inhibition of neuronal cell migration.

In certain embodiments, the recombinant ROBO2-Fc protein inhibits the binding of SLIT ligand to ROBO2 (e.g., can be assessed by assessing competitive binding between the recombinant ROBO2-Fc protein and ROBO2 to SLIT2).

For example, an assay may compare (i) the binding of ROBO2 and SLIT in the presence of the recombinant ROBO2-Fc protein with (ii) the binding of ROBO2 and SLIT in the absence of the recombinant ROBO2-Fc protein. The reduction in binding of ROBO2 and SLIT can be at least about 10%, at least about 20%, at least about 30%, at least about 40%, at least about 50%, at least about 60%, at least about 70%, at least about 80%, at least about 90%, at least about 95%, at least about 96%, at least about 97%, at least about 98%, or at least about 99%, in the presence of the recombinant ROBO2-Fc protein compared with binding of ROBO2 and SLIT in the absence of the test recombinant ROBO2-Fc protein. The expected binding of SLIT to ROBO2 in the absence of the recombinant ROBO2-Fc protein can be set as 100%.

In certain embodiments, the recombinant ROBO2-Fc protein inhibits the binding of SLIT to ROBO2, with a half maximal inhibitory concentration ($IC_{50}$) of not more than about $1 \times 10^{-7}$ M, not more than about $1 \times 10^{-8}$ M, not more than about $1 \times 10^{-9}$ M, not more than about $1 \times 10^{-10}$ M, not more than about $1 \times 10^{-11}$ M, not more than about $1 \times 10^{-12}$ M, not more than about $1 \times 10^{-13}$ M, not more than about $1 \times 10^{-14}$ M, not more than about $1 \times 10^{-15}$ M, from about $1 \times 10^{-7}$ M to about $5 \times 10^{-14}$ M, from about $1 \times 10^{-7}$ M to about $1 \times 10^{-14}$ M, from about $1 \times 10^{-7}$ M to about $5 \times 10^{-13}$ M, from about $1 \times 10^{-7}$ M to about $1 \times 10^{-13}$ M, from about $1 \times 10^{-7}$ M to about $5 \times 10^{-12}$ M, or from about $1 \times 10^{-7}$ M to about $1 \times 10^{-12}$ M. In some embodiments, the recombinant ROBO2-Fc protein has a half maximal inhibitory concentration ($IC_{50}$) of not more than 15 nM, about 13 nM, about 11 nM, about 9 nM, about 7 nM, about 6 nM, about 5 nM, about 4 nM, about 3 nM, about 2 nM, about 1 nM as measured by a homogenous time-resolved fluorescence (HTRF) assay for inhibition of binding of ROBO2 to SLIT2. The $IC_{50}$ may be assessed using a fragment of SLIT or ROBO2, such as SLIT-N, and Ig domain 1 of ROBO2, or Ig domains 1 & 2 of ROBO2.

The inhibitory activity of a recombinant ROBO2-Fc protein can also be assessed by measuring the level of ROBO2-dependent SLIT-N activity, such as actin polymerization, podocyte adhesion, and/or SLIT2-N mediated inhibition of neuronal cell migration. For example, the assay can compare (i) neuronal cell migration in the presence of ROBO2, SLIT, and the recombinant ROBO2-Fc protein with (ii) neuronal cell migration in the presence of ROBO2, SLIT, but in the absence of the recombinant ROBO2-Fc protein. The increase in neuronal cell migration can be at least about 10%, at least about 20%, at least about 30%, at least about 40%, at least about 50%, at least about 60%, at least about 70%, at least about 80%, at least about 90%, at least about 95%, at least about 96%, at least about 97%, at least about 98%, or at least about 99%, in the presence of the recombinant ROBO2-Fc protein compared with neuronal cell migration in the absence of the recombinant ROBO2-Fc protein. The baseline neuronal cell migration in the absence of the recombinant ROBO2-Fc protein can be set as 0%.

In certain embodiments, the recombinant ROBO2-Fc protein inhibits ROBO2-dependent SLIT-N activity, such as actin polymerization, podocyte adhesion, and/or SLIT2-N mediated inhibition of neuronal cell migration, with a half maximal inhibitory concentration ($IC_{50}$) of not more than about $1 \times 10^{-7}$ M, not more than about $1 \times 10^{-8}$ M, not more than about $1 \times 10^{-9}$ M, not more than about $1 \times 10^{-10}$ not more than about $1 \times 10^{-11}$ M, not more M, than about $1 \times 10^{-12}$ M, not more than about $1 \times 10^{-13}$ M, not more than about $1 \times 10^{-14}$ M, not more than about $1 \times 10^{-15}$ M, from about $1 \times 10^{-7}$ M to about $5 \times 10^{-14}$ M, from about $1 \times 10^{-7}$ M to about $1 \times 10^{-14}$ M, from about $1 \times 10^{-7}$ M to about $5 \times 10^{-13}$ M, from about $1 \times 10^{-7}$ M to about $1 \times 10^{-13}$ M, from about $1 \times 10^{-7}$ M to about $5 \times 10^{-12}$ M, or from about $1 \times 10^{-7}$ M to about $1 \times 10^{-12}$ M. In certain embodiments, $IC_{50}$ of from about $1 \times 10^{-10}$ M to about $1 \times 10^{-13}$ M is preferred. In certain embodiments, $IC_{50}$ of from about $5 \times 10^{-11}$ M to about $5 \times 10^{-12}$ M is preferred. In some embodiments, the recombinant ROBO-Fc protein has a half maximal inhibitory concentration ($IC_{50}$) of not more than about 75 nM, about 65 nM, about 55 nM, about 45 nM, about 35 nM, about 25 nM, about 15 nM, about 5 nM as assessed by measuring SLIT2-N mediated inhibition of neuronal cell migration.

In certain embodiments, the characteristics of the recombinant ROBO-Fc protein of the invention is further assessed using other biological activity assays, e.g., in order to evaluate its potency, pharmacological activity, and potential efficacy as a therapeutic agent. Such assays are known in the art and depend on the intended use for the recombinant protein. Examples include e.g., toxicity assays, immunogenicity assays, stability assays, anti-drug antibody assays, and/or PK/PD profiling.

Nucleic Acids and Methods of Producing Recombinant ROBO2 proteins

The invention also provides polynucleotides encoding the recombinant ROBO2 proteins of the invention. The invention also provides a method of making any of the polynucleotides described herein. Polynucleotides can be made and expressed by procedures known in the art.

In one aspect, the invention provides polynucleotides or compositions comprising polynucleotides encoding a recombinant ROBO2 protein comprising a portion of a ROBO2 extracellular domain (ECD) and further comprising an immunoglobulin domain, wherein the extracellular domain comprises: at least two immunoglobulin-like (Ig-like) domains; and a C-terminus sequence consisting of the sequence of SEQ ID NO: 12.

In one aspect, the invention provides polynucleotides or compositions, comprising polynucleotides encoding a recombinant ROBO2 protein comprising amino acid residues 1 to 203 according the numbering set forth in SEQ ID NO: 1 and further comprising an immunoglobulin domain.

In some embodiments, the invention provides polynucleotides or compositions, comprising polynucleotides encoding any one of the following recombinant ROBO2 proteins: ROBO2-Fc 2.2 (SEQ ID NO: 1), ROBO2-Fc 2.1 (SEQ ID NO: 2), ROBO2-Fc 2.0 (SEQ ID NO: 3), ROBO2-Fc 1.1 (SEQ ID NO: 4), ROBO2-Fc 1.0 (SEQ ID NO: 5), ROBO2-Fc 3.0 (SEQ ID NO: 6), ROBO2-Fc 4.0 (SEQ ID NO: 7), and ROBO2-Fc S17T R73Y (SEQ ID NO: 19). In some embodiments, the invention provides polynucleotides or compositions, comprising polynucleotides encoding ROBO2-Fc 2.2 (SEQ ID NO: 1). In some embodiments, the invention provides polynucleotides or compositions, comprising polynucleotides encoding ROBO2-Fc 2.1 (SEQ ID NO: 2). In some embodiments, the invention provides polynucleotides or compositions, comprising polynucleotides encoding ROBO2-Fc 2.0 (SEQ ID NO: 3).

The invention also provides polynucleotides or compositions comprising the same, wherein the polynucleotide comprises the sequence of the DNA insert of the plasmid deposited with the ATCC having ATCC Accession No. PTA-124008.

In another aspect, the invention provides polynucleotides and variants thereof encoding a recombinant ROBO2-Fc protein, wherein such variant polynucleotides share at least 70%, at least 75%, at least 80%, at least 85%, at least 87%, at least 89%, at least 90%, at least 91%, at least 92%, at least 93%, at least 94%, at least 95%, at least 96%, at least 97%, at least 98%, or at least 99% sequence identity to any nucleic acid disclosed herein such as, but not limited to, a nucleic acid comprising the nucleic acid of SEQ ID NOs: 1, 2, 3, 4, 5, 6, 7 and 19 and the nucleic acid sequence of the insert of the plasmid deposited with the ATCC having ATCC Accession No. PTA-124008. In some embodiments, such variant polynucleotides share at least 95%, sequence identity to any nucleic acid disclosed herein such as, but not limited to, a nucleic acid comprising the nucleic acid of SEQ ID NOs: 1, 2, 3, 4, 5, 6, 7 and 19. In some embodiments, such variant polynucleotides share at least 96%, sequence identity to any nucleic acid disclosed herein such as, but not limited to, a nucleic acid comprising the nucleic acid of SEQ ID NOs: 1, 2, 3, 4, 5, 6, 7 and 19. In some embodiments, such variant polynucleotides share at least 97%, sequence identity to any nucleic acid disclosed herein such as, but not limited to, a nucleic acid comprising the nucleic acid of SEQ ID NOs: 1, 2, 3, 4, 5, 6, 7 and 19. In some embodiments, such variant polynucleotides share at least 98%, sequence identity to any nucleic acid disclosed herein such as, but not limited to, a nucleic acid comprising the nucleic acid of SEQ ID NOs: 1, 2, 3, 4, 5, 6, 7 and 19. In some embodiments, such variant polynucleotides share at least 99%, sequence identity to any nucleic acid disclosed herein such as, but not limited to, a nucleic acid comprising the nucleic acid of SEQ ID NOs: 1, 2, 3, 4, 5, 6, 7 and 19.

In another aspect, the invention includes polynucleotides and variants thereof comprising the nucleic acid sequence set forth in SEQ ID NO: 21. In some embodiments, the invention includes polynucleotides and variants thereof comprising the nucleic acid sequence set forth in SEQ ID NO: 21, and further comprising a nucleic acid sequence encoding the amino acid sequence set forth in SEQ ID NO:17 or SEQ ID NO: 18. In some embodiments, the nucleic acid sequence encoding the amino acid sequence set forth in SEQ ID NO: 17 or SEQ ID NO: 18 is N-terminal to the nucleic acid sequence set forth in SEQ ID NO: 21.

In one embodiment, the extracellular domain of ROBO2 and the immunoglobulin Fc domain are encoded by separate polynucleotides. Alternatively, both the extracellular domain of ROBO2 and the immunoglobulin Fc domain are encoded by a single polynucleotide.

Polynucleotides complementary to any such sequences are also encompassed by the present disclosure. Polynucleotides may be single-stranded (coding or antisense) or double-stranded, and may be DNA (recombinant, cDNA or synthetic) or RNA molecules. RNA molecules include hnRNA molecules, which contain introns and correspond to a DNA molecule in a one-to-one manner, and mRNA molecules, which do not contain introns. Additional coding or non-coding sequences may, but need not, be present within a polynucleotide of the present disclosure, and a polynucleotide may, but need not, be linked to other molecules and/or support materials.

Polynucleotides may comprise a native sequence (i.e., a wild type sequence) or may comprise a non-native (i.e., variant) of such a sequence. Polynucleotide variants contain one or more substitutions, additions, deletions and/or insertions such that the SLIT binding ability of the encoded polypeptide is not diminished, relative to a native molecule. The effect on the SLIT binding activity of the encoded polypeptide may generally be assessed as described herein. In some embodiments, variants exhibit at least about 70% identity, in some embodiments, at least about 80% identity, in some embodiments, at least about 90% identity, and in some embodiments, at least about 95% identity to a polynucleotide sequence that encodes a recombinant ROBO2-Fc protein comprising the native (wild type) sequences of ROBO2 and a Fc domain.

In some embodiments, variants encode a recombinant ROBO2 protein comprising amino acid residues having at least 20, at least 19, at least 18, at least 17, at least 16, at least 15, at least 14, at least 13, at least 12, at least 11, at least 10, at least 9, at least 8, at least 7, at least 6, at least 5, at least 4, at least 3, at least 2, or at least 1 amino acid substitutions of the amino acid residues 1 to 203 according the numbering set forth in SEQ ID NO: 1. In some embodiments, variants encode a recombinant ROBO2 protein comprising amino acid residues having at least 5 amino acid substitutions of the amino acid residues 1 to 203 according the numbering set forth in SEQ ID NO: 1. In some embodiments, variants encode a recombinant ROBO2 protein comprising amino acid residues having at least 4 amino acid substitutions of the amino acid residues 1 to 203 according the numbering set forth in SEQ ID NO: 1. In some embodiments, variants encode a recombinant ROBO2 protein comprising amino acid residues having at least 3 amino acid substitutions of the amino acid residues 1 to 203 according the numbering set forth in SEQ ID NO: 1. In some embodiments, variants encode a recombinant ROBO2 protein comprising amino acid residues having at least 2 amino acid substitutions of the amino acid residues 1 to 203 according the numbering set forth in SEQ ID NO: 1. In some embodiments, variants encode a recombinant ROBO2 protein comprising amino acid residues having at least 1 amino acid substitution of the amino acid residues 1 to 203 according the numbering set forth in SEQ ID NO: 1. These amounts are not meant to be limiting, and increments between the recited percentages are specifically envisioned as part of the disclosure.

Two polynucleotide or polypeptide sequences are said to be "identical" if the sequence of nucleotides or amino acids in the two sequences is the same when aligned for maximum correspondence as described below. Comparisons between two sequences are typically performed by comparing the sequences over a comparison window to identify and compare local regions of sequence similarity. A "comparison window" as used herein, refers to a segment of at least about 20 contiguous positions, usually 50 to about 450, or 100 to about 300, in which a sequence may be compared to a reference sequence of the same number of contiguous positions after the two sequences are optimally aligned.

Optimal alignment of sequences for comparison may be conducted using the MegAlign® program in the Lasergene® suite of bioinformatics software (DNASTAR®, Inc., Madison, Wis.), using default parameters. This program embodies several alignment schemes described in the following references: Dayhoff, M. O., 1978, A model of evolutionary change in proteins—Matrices for detecting distant relationships. In Dayhoff, M.O. (ed.) Atlas of Protein Sequence and Structure, National Biomedical Research Foundation, Washington D.C. Vol. 5, Suppl. 3, pp. 345-358; Hein J., 1990, Unified Approach to Alignment and Phylogenes pp. 626-645 Methods in Enzymology vol. 183, Academic Press, Inc., San Diego, Calif.; Higgins, D. G. and Sharp, P. M., 1989, CABIOS 5:151-153; Myers, E. W. and Muller W., 1988, CABIOS 4:11-17; Robinson, E. D., 1971, Comb. Theor. 11:105; Santou, N., Nes, M., 1987, Mol. Biol. Evol. 4:406-425; Sneath, P. H. A. and Sokal, R. R., 1973, Numerical Taxonomy the Principles and Practice of Numerical Taxonomy, Freeman Press, San Francisco, Calif.; Wilbur, W. J. and Lipman, D. J., 1983, Proc. Natl. Acad. Sci. USA 80:726-730.

In some embodiments, the "percentage of sequence identity" is determined by comparing two optimally aligned sequences over a window of comparison of at least 20 positions, wherein the portion of the polynucleotide or polypeptide sequence in the comparison window may comprise additions or deletions (i.e., gaps) of 20 percent or less, usually 5 to 15 percent, or 10 to 12 percent, as compared to the reference sequences (which does not comprise additions or deletions) for optimal alignment of the two sequences. The percentage is calculated by determining the number of positions at which the identical nucleic acid bases or amino acid residue occurs in both sequences to yield the number of matched positions, dividing the number of matched positions by the total number of positions in the reference sequence (i.e., the window size) and multiplying the results by 100 to yield the percentage of sequence identity.

Variants may also, or alternatively, be substantially homologous to a native gene, or a portion or complement thereof. Such polynucleotide variants are capable of hybridizing under moderately stringent conditions to a naturally occurring DNA sequence encoding a recombinant ROBO2-Fc protein comprising the native (wild type) sequences of ROBO2 and a Fc domain (or a complementary sequence).

Suitable "moderately stringent conditions" include pre-washing in a solution of 5×SSC, 0.5% SDS, 1.0 mM EDTA (pH 8.0); hybridizing at 50° C.-65° C., 5×SSC, overnight; followed by washing twice at 65° C. for 20 minutes with each of 2×, 0.5× and 0.2×SSC containing 0.1% SDS.

As used herein, "highly stringent conditions" or "high stringency conditions" are those that: (1) employ low ionic strength and high temperature for washing, for example 0.015 M sodium chloride/0.0015 M sodium citrate/0.1% sodium dodecyl sulfate at 50° C.; (2) employ a denaturing agent during hybridization, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) employ 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 μg/mL), 0.1% SDS, and 10% dextran sulfate at 42° C., with washes at 42° C. in 0.2×SSC (sodium chloride/sodium citrate) and 50% formamide at 55° C., followed by a high-stringency wash consisting of 0.1×SSC containing EDTA at 55° C. The skilled artisan will recognize how to adjust the temperature, ionic strength, etc. as necessary to accommodate factors such as probe length and the like.

It will be appreciated by those of ordinary skill in the art that, as a result of the degeneracy of the genetic code, there are many nucleotide sequences that encode a ROBO2-Fc polypeptide comprising an amino acid sequence as described herein. Some of these polynucleotides bear minimal homology to the nucleotide sequence of any native gene. Nonetheless, polynucleotides that vary due to differences in codon usage are specifically contemplated by the present disclosure. Further, alleles of the genes comprising the polynucleotide sequences provided herein are within the scope of the present disclosure. Alleles are endogenous genes that are altered as a result of one or more mutations, such as deletions, additions and/or substitutions of nucleotides. The resulting mRNA and protein may, but need not, have an altered structure or function. Alleles may be identified using standard techniques (such as hybridization, amplification and/or database sequence comparison).

The present invention also includes codon-optimized polynucleotides wherein the nucleic acid sequence has been optimized to maximize expression in a particular cell. In general, codon optimization refers to a process of modifying a nucleic acid sequence for enhanced expression in the host cells of interest by replacing at least one codon (e.g. about or more than about 1, 2, 3, 4, 5, 10, 15, 20, 25, 50, or more codons) of the native sequence with codons that are more frequently or most frequently used in the genes of that host cell while maintaining the native amino acid sequence, Various species exhibit particular bias for certain codons of a particular amino acid. Codon bias (differences in codon usage between organisms) often correlates with the efficiency of translation of messenger RNA (mRNA), which is in turn believed to be dependent on, among other things, the properties of the codons being translated and the availability of particular transfer RNA (tRNA) molecules. The predominance of selected tRNAs in a cell is generally a reflection of the codons used most frequently in peptide synthesis. Accordingly, genes can be tailored for optimal gene expression in a given organism based on codon optimization. Codon usage tables are readily available, and these tables can be adapted in a number of ways (e.g., Nakamura, Y., et al. "Codon usage tabulated from the international DNA sequence databases: status for the year 2000" Nucl. Acids Res. 28:292 (2000)). Computer algorithms for codon optimizing a particular sequence for expression in a particular host cell are also available, such as Gene Forge (Aptagen; Jacobus, Pa.), are also available. In some embodiments, one or more codons (e.g. 1, 2, 3, 4, 5, 10, 15, 20, 25, 50, or more, or all codons) in a sequence encoding a recombinant ROBO2-Fc protein correspond to the most frequently used codon for a particular amino acid.

Thus, in one aspect, the modified nucleic acid sequence provides a detectably greater level of expression of recombinant ROBO2 protein in a cell compared with the expression of recombinant ROBO2 protein from the wild type nucleic acid sequence of, e.g., nucleic acid encoding ROBO2-Fc 2.2 (SEQ ID NO:21), in an otherwise identical cell. This can be referred to as an "expression optimized" or "enhanced expression" nucleic acid, or simply, as a "modified nucleic acid."

"Optimized" or "codon-optimized" as referred to interchangeably herein, refers to a coding sequence that has been optimized relative to a wild type coding sequence (e.g., a coding sequence for human ROBO2 and/or human Fc domain) to increase expression of the coding sequence, e.g., by minimizing usage of rare codons, decreasing the number of CpG dinucleotides, removing cryptic splice donor or acceptor sites, removing Kozak sequences, removing ribosomal entry sites, and the like.

Examples of modifications include elimination of one or more cis-acting motifs and introduction of one or more Kozak sequences. In one embodiment, one or more cis-acting motifs are eliminated and one or more Kozak sequences are introduced.

Examples of cis acting motifs that may be eliminated include internal TATA-boxes; chi-sites; ribosomal entry sites; ARE, INS, and/or CRS sequence elements; repeat sequences and/or RNA secondary structures; (cryptic) splice donor and/or acceptor sites, branch points; and SalI.

In one embodiment, the GC content (e.g., the number of G and C nucleotides present in a nucleic acid sequence) is enhanced relative to wild-type ROBO2 and/or human IgG1 Fc domain gene sequence of the novel ROBO2 proteins of the invention. The GC content is preferably at least 5%, more preferably, at least 6%, yet more preferably, at least 7%, even more preferably, at least 8%, more preferably, at least 9%, even more preferably, at least 10%, yet more preferably, at least 12%, even more preferably, at least 14%, yet more preferably, at least 15%, more preferably, at least 17%, even more preferably, at least 20%, even further preferably, at least 30%, yet more preferably, at least 40%, more preferably, at least 50%, even more preferably, at least 60%, and most preferably, at least 70% greater than the wild type gene (e.g., SEQ ID NO:21).

In another embodiment, the GC content is expressed as a percentage of G (guanine) and C (cytosine) nucleotides in the sequence. That is, the GC content of the wild type nucleic acid encoding ROBO2-Fc 2.2 (SEQ ID NO:21) is less than the GC content of a codon-optimized nucleic acid sequence encoding ROBO2-Fc 2.2.

In one embodiment, the GC content of a modified nucleic acid of the invention is greater than the GC content of the wild type nucleic acid encoding ROBO2-Fc 2.2 comprising the nucleic acid sequence of SEQ ID NO:21. One skilled in the art would appreciate, knowing the degeneracy of the nucleic acid code, that irrespective of the sequence of the nucleic acid encoding the protein, the amino acid sequence of ROBO2-Fc 2.2 expressed therefrom is, preferably, the amino acid sequence of SEQ ID NO:1.

It is known that methylation of CpG dinucleotides plays an important role in the regulation of gene expression in eukaryotes. Specifically, methylation of CpG dinucleotides in eukaryotes essentially serves to silence gene expression through interfering with the transcriptional machinery. As such, because of the gene silencing evoked by methylation of CpG motifs, the nucleic acids and vectors of the invention having a reduced number of CpG dinucleotides will provide for high and long-lasting transgene expression level.

Potential CpG Islands can be identified using publicly available software found at, e.g., http://www.bioinformatics.org/sms2/cpg_islands.html. The CpG Islands software can report potential CpG island regions using the method described by Gardiner-Garden and Frommer, 1987, J. Mol. Biol. 196(2):261-282, among many other methods well-known in the art for identifying potential CpG islands. The calculation can be performed using a 200 basepair (bp) window moving across the sequence at 1 bp intervals. CpG islands are defined as sequence ranges where the Obs/Exp value is greater than 0.6 and the GC content is greater than 50%. The expected number of CpG dimers in a window can be calculated as the number of 'C's in the window multiplied by the number of 'G's in the window, divided by the window length. Thus, the potential CpG islands present in a nucleic acid sequence can be readily determined by inputting the sequence at issue into the window provided by the software (indicated by the instructions to "Paste the raw sequence or one or more FASTA sequences into the text area below. Input limit is 100000 characters."). CpG islands are often found in the 5' regions of vertebrate genes, therefore this program can be used to highlight potential genes in genomic sequences.

The polynucleotides of this disclosure can be obtained using chemical synthesis, recombinant methods, or PCR. Methods of chemical polynucleotide synthesis are well known in the art and need not be described in detail herein. One of skill in the art can use the sequences provided herein and a commercial DNA synthesizer to produce a desired DNA sequence.

For preparing polynucleotides using recombinant methods, a polynucleotide comprising a desired sequence can be inserted into a suitable vector, and the vector in turn can be introduced into a suitable host cell for replication and amplification, as further discussed herein. Polynucleotides may be inserted into host cells by any means known in the art. Cells are transformed by introducing an exogenous polynucleotide by direct uptake, endocytosis, transfection, F-mating or electroporation. Once introduced, the exogenous polynucleotide can be maintained within the cell as a non-integrated vector (such as a plasmid) or integrated into the host cell genome. The polynucleotide so amplified can be isolated from the host cell by methods well known within the art. See, e.g., Sambrook et al., 1989.

Alternatively, PCR allows reproduction of DNA sequences. PCR technology is well known in the art and is described in U.S. Pat. Nos. 4,683,195, 4,800,159, 4,754,065 and 4,683,202, as well as PCR: The Polymerase Chain Reaction, Mullis et al. eds., Birkauswer Press, Boston, 1994.

RNA can be obtained by using the isolated DNA in an appropriate vector and inserting it into a suitable host cell. When the cell replicates and the DNA is transcribed into RNA, the RNA can then be isolated using methods well known to those of skill in the art, as set forth in Sambrook et al., 1989, for example.

Suitable cloning vectors may be constructed according to standard techniques, or may be selected from a large number of cloning vectors available in the art. While the cloning vector selected may vary according to the host cell intended to be used, useful cloning vectors will generally have the ability to self-replicate, may possess a single target for a particular restriction endonuclease, and/or may carry genes for a marker that can be used in selecting clones containing the vector. Suitable examples include plasmids and bacterial viruses, e.g., pUC18, pUC19, Bluescript (e.g., pBS SK+) and its derivatives, mp18, mp19, pBR322, pMB9, ColE1, pCR1, RP4, phage DNAs, and shuttle vectors such as pSA3 and pAT28. These and many other cloning vectors are available from commercial vendors such as BioRad, Stratgene, and Invitrogen.

Expression vectors are further provided. Expression vectors generally are replicable polynucleotide constructs that contain a polynucleotide according to the disclosure. It is implied that an expression vector must be replicable in the host cells either as episomes or as an integral part of the chromosomal DNA. Suitable expression vectors include but are not limited to plasmids, viral vectors, including adenoviruses, adeno-associated viruses, retroviruses, cosmids, and expression vector(s) disclosed in PCT Publication No. WO 87/04462. Vector components may generally include, but are not limited to, one or more of the following: a signal sequence; an origin of replication; one or more marker genes; suitable transcriptional controlling elements (such as promoters, enhancers and terminator). For expression (i.e., translation), one or more translational controlling elements are also usually required, such as ribosome binding sites, translation initiation sites, and stop codons.

In some embodiments, a vector comprises the nucleic acid molecule set forth in SEQ ID NO: 21. In some embodiments, a vector comprises the nucleic acid molecule set forth in SEQ ID NO: 21 and a nucleic acid sequence encoding the amino acid sequence set forth in SEQ ID NO: 17 or SEQ ID NO: 18. In some embodiments, the nucleic acid sequence encoding the amino acid sequence set forth in SEQ ID NO: 17 or SEQ ID NO: 18 is N-terminal to the nucleic acid sequence set forth in SEQ ID NO: 21.

The vectors containing the polynucleotides of interest and/or the polynucleotides themselves, can be introduced into the host cell by any of a number of appropriate means, including electroporation, transfection employing calcium chloride, rubidium chloride, calcium phosphate, DEAE-dextran, or other substances; microprojectile bombardment; lipofection; and infection (e.g., where the vector is an infectious agent such as vaccinia virus). The choice of introducing vectors or polynucleotides will often depend on features of the host cell.

Exemplary host cells include an *E. coli* cell, a yeast cell, an insect cell, a simian COS cell, a Chinese hamster ovary (CHO) cell, or a myeloma cell. Preferred host cells include a CHO cell, a Human embryonic kidney (HEK) 293 cell, or a Sp2.0 cell, among many cells well-known in the art.

The host cells may be cultured under conditions which allow expression of the encoded recombinant ROBO2 protein. In some embodiments, the encoded recombinant ROBO2-Fc protein comprises the ROBO2 leader sequence set forth in SEQ ID NO: 17 or the Ig leader sequence set forth in SEQ ID NO: 18. In some embodiments, the ROBO2 leader sequence (SEQ ID NO: 17) is cleaved during protein production to produce mature ROBO2-Fc. In some embodiments, the Ig leader sequence (SEQ ID NO: 18) is cleaved during protein production to produce mature ROBO2-Fc, e.g., ROBO2-Fc 2.2.

4. Formulations and Uses

The recombinant ROBO2 proteins of the invention can be formulated as a pharmaceutical composition. The pharmaceutical composition may further comprise a pharmaceutically acceptable carrier, excipient, and/or stabilizer (Remington: The Science and practice of Pharmacy 20th Ed., 2000, Lippincott Williams and Wilkins, Ed. K. E. Hoover), in the form of lyophilized formulation or aqueous solution. As used herein, "pharmaceutically acceptable carrier" or "pharmaceutical acceptable excipient" includes any material which, when combined with an active ingredient, allows the ingredient to retain biological activity and is non-reactive with the subject's immune system. Examples include, but are not limited to, any of the standard pharmaceutical carriers such as a phosphate buffered saline solution, water, emulsions such as oil/water emulsion, and various types of wetting agents. Preferred diluents for aerosol or parenteral administration are phosphate buffered saline (PBS) or normal (0.9%) saline. Compositions comprising such carriers are formulated by well-known conventional methods (see, for example, Remington's Pharmaceutical Sciences, 18th edition, A. Gennaro, ed., Mack Publishing Co., Easton, Pa., 1990; and Remington, The Science and Practice of Pharmacy, 20th Ed., Mack Publishing, 2000).

Acceptable carriers, excipients, or stabilizers are nontoxic to recipients at the dosages and concentrations, and may comprise buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrans; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG). Pharmaceutically acceptable excipients are further described herein.

Diagnostic Uses

The recombinant ROBO2 proteins of the invention can be used for various therapeutic or diagnostic purposes. For example, the recombinant ROBO2 proteins of the invention may be used as an affinity purification agent (e.g., for in vitro purification of SLIT ligands, such as SLIT2), as a diagnostic agent (e.g., for detecting expression of a SLIT ligand (e.g., SLIT2 in specific cells, tissues, or serum). Exemplary diagnostic assays for a SLIT ligand, such as SLIT2, may comprise, e.g., contacting a sample, obtained from a patient, with a recombinant ROBO2 protein of the invention, wherein the recombinant ROBO2 protein is labeled with a detectable label or reporter molecule.

The invention encompasses use of the recombinant ROBO2 proteins disclosed herein as diagnostic imaging methods for the visualization of a SLIT ligand, such as SLIT2, in a sample, cell, tissue or patient. For instance, the recombinant ROBO2 protein can be conjugated to an imaging agent such that the presence of the recombinant ROBO2 protein can be detected thereby detecting the presence of a SLIT ligand, such as SLIT2.

Therapeutic Uses

Exemplary therapeutic uses of the recombinant ROBO2 proteins of the invention include treating a renal disease, such as a glomerular disease, focal segmental glomerular disease (FSGS). The recombinant ROBO2 proteins of the invention may also be used in prophylactic treatment (e.g., administering to a subject who has not exhibited a disease symptom but is susceptible to a renal disease such as a glomerular disease, FSGS).

In another aspect, the invention includes treatment of any disorder, disease or condition mediated by or associated with an increased level of protein in the urine compared with the level of protein in urine in the absence of the disease, disorder or condition. Such disease, disorder or condition includes, but is not limited to, lupus nephritis, IgA nephropathy, membranous nephropathy (MN), minimal change disease (MCD), fibrosis (such as liver fibrosis), nonalcoholic steatohepatitis (NASH), proteinuria, albuminuria, glomerulonephritis, diabetic nephropathy, nephrotic syndrome, focal glomerulosclerosis, acute renal failure, acute tubulointerstitial nephritis, pyelonephritis, renal graft rejection, and reflux nephropathy.

For therapeutic applications, the recombinant ROBO2 proteins of the invention can be administered to a mammal, especially a human, by conventional techniques, such as intravenously (as a bolus or by continuous infusion over a period of time), intramuscularly, intraperitoneally, intracerebrospinally, subcutaneously, intra-articularly, intrasynovially, intrathecally, orally, topically, or by inhalation. The recombinant ROBO2 proteins of the invention also can be suitably administered by intra-tumoral, peri-tumoral, intra-lesional, or peri-lesional routes.

Accordingly, in one aspect, the invention provides a method of reducing the activity of ROBO2, comprising administering to a subject (e.g., a human) in need thereof a therapeutically effective amount of a recombinant ROBO2 protein of the invention.

In another aspect, the invention provides a method of preserving or modulating podocyte function, comprising administering to a subject (e.g., a human) in need thereof a therapeutically effective amount of a recombinant ROBO2 protein of the invention.

In certain embodiments, the subject suffers from or is susceptible to a renal disease. In certain embodiments, the renal disease is a glomerular disease. In certain embodiments, the renal disease is FSGS.

In certain embodiments, the subject suffers from or is susceptible to nephropathy.

In another aspect, the invention provides a recombinant ROBO2 protein of the invention for use in a method of treatment disclosed herein. For example, the invention provides a recombinant ROBO2 protein of the invention for use in reducing the activity of ROBO2 in a cell, reducing the activity of ROBO2 in a subject, preserving podocyte function in a subject, modulating podocyte function in a subject, treating a glomerular disease in a subject and treating nephropathy in a subject.

In a further aspect, the invention provides the use of a recombinant ROBO2 protein of the invention in the manufacture of a medicament for reducing the activity of ROBO2 in a cell, reducing the activity of ROBO2 in a subject, preserving podocyte function in a subject, modulating podocyte function in a subject, treating a glomerular disease in a subject and treating nephropathy in a subject.

Dosing and Administration

In certain embodiments, the recombinant ROBO2 protein of the invention is administered subcutaneously. In certain embodiments, the recombinant ROBO2 protein of the invention is administered intravenously.

The pharmaceutical compositions may be administered to a subject in need thereof at a frequency that may vary with the severity of the renal disease. In the case of prophylactic therapy, the frequency may vary depending on the subject's susceptibility or predisposition to a renal disease. In some embodiments, the pharmaceutical composition is administered as a single dose subcutaneously or intravenously. In some embodiments, the pharmaceutical composition is administered as multiple doses subcutaneously or intravenously.

The compositions may be administered to patients in need as a bolus or by continuous infusion. For example, a bolus administration of a recombinant ROBO2 protein may be in an amount of from 0.0025 to 200 mg/kg body weight, 0.025 to 0.25 mg/kg, 0.010 to 0.10 mg/kg or 0.10-0.50 mg/kg. For continuous infusion, a recombinant ROBO2 protein may be administered at 0.001 to 200 mg/kg body weight/minute, 0.0125 to 1.25 mg/kg/min, 0.010 to 0.75 mg/kg/min, 0.010 to 1.0 mg/kg/min. or 0.10-0.50 mg/kg/min for a period of 1-24 hours, 1-12 hours, 2-12 hours, 6-12 hours, 2-8 hours, or 1-2 hours.

For administration of recombinant ROBO2 proteins dosage amounts may be from about 1 mg/kg to about 10 mg/kg, from about 2 mg/kg to about 10 mg/kg, from about 3 mg/kg to about 10 mg/kg, from about 4 mg/kg to about 10 mg/kg, from about 5 mg/kg to about 10 mg/kg, from about 1 mg/kg to about 20 mg/kg, from about 2 mg/kg to about 20 mg/kg, from about 3 mg/kg to about 20 mg/kg, from about 4 mg/kg to about 20 mg/kg, from about 5 mg/kg to about 20 mg/kg, about 1 mg/kg or more, about 2 mg/kg or more, about 3 mg/kg or more, about 4 mg/kg or more, about 5 mg/kg or more, about 6 mg/kg or more, about 7 mg/kg or more, about 8 mg/kg or more, about 9 mg/kg or more, about 10 mg/kg or more, about 11 mg/kg or more, about 12 mg/kg or more, about 13 mg/kg or more, about 14 mg/kg or more, about 15 mg/kg or more, about 16 mg/kg or more, about 17 mg/kg or more, about 19 mg/kg or more, or about 20 mg/kg or more. The frequency of the administration would depend upon the severity of the condition. Frequency could range from three times per week to once every two or three weeks.

Additionally, the compositions may be administered to patients via subcutaneous injection. For example, a dose of 1 to 200 mg recombinant ROBO2 protein can be administered to patients via subcutaneous or intravenous injection administered twice a week, once a week, once every two weeks, once every three weeks, once every four weeks, once every five weeks, once every six weeks, once every seven weeks, once every eight weeks, once every nine weeks, once every ten weeks, twice a month, once a month, once every two months, or once every three months.

In certain embodiments, the half-life of the recombinant ROBO2 protein in human is about 24 hours, about 2 days, about 4 days, about 5 days, about 6 days, about 7 days, about 8 days, about 9 days, about 10 days, about 11 days, about 12 days, about 13 days, about 14 days, about 15 days, about 16 days, about 17 days, about 18 days, about 19 days, about 20 days, about 21 days, about 22 days, about 23 days, about 24 days, about 25 days, about 26 days, about 27 days, about 28 days, about 29 days, about 30 days, from about 5 days to about 40 days, from about 5 days to about 35 days, from about 5 days to about 30 days, from about 5 days to about 25 days, from about 10 days to about 40 days, from about 10 days to about 35 days, from about 10 days to about 30 days, from about 10 days to about 25 days, from about 15 days to about 40 days, from about 15 days to about 35 days, from about 15 days to about 30 days, or from about 15 days to about 25 days, In certain embodiments, the pharmaceutical composition is administered subcutaneously or intravenously every 2-6 weeks, with a dose from about 0.1 mg/kg to about 10 mg/kg, from about 0.5 mg/kg to about 10 mg/kg, from about 1 mg/kg to about 10 mg/kg, from about 1.5 mg/kg to about 10 mg/kg, from about 2 mg/kg to about 10 mg/kg, from about 0.1 mg/kg to about 8 mg/kg, from about 0.5 mg/kg to about 8 mg/kg, from about 1 mg/kg to about 8 mg/kg, from about 1.5 mg/kg to about 8 mg/kg, from about 2 mg/kg to about 8 mg/kg, from about 0.1 mg/kg to about 5 mg/kg, from about 0.5 mg/kg to about 5 mg/kg, from about 1 mg/kg to about 5 mg/kg, from about 1.5 mg/kg to about 5 mg/kg, from about 2 mg/kg to about 5 mg/kg, about 0.5 mg/kg, about 1.0 mg/kg, about 1.5 mg/kg, about 2.0 mg/kg, about 2.5 mg/kg, about 3.0 mg/kg, about 3.5 mg/kg, about 4.0 mg/kg, about 4.5 mg/kg, about 5.0 mg/kg, about 5.5 mg/kg, about 6.0 mg/kg, about 6.5 mg/kg, about 7.0 mg/kg, about 7.5 mg/kg, about 8.0 mg/kg, about 8.5 mg/kg, about 9.0 mg/kg, about 9.5 mg/kg, or about 10.0 mg/kg.

In certain embodiments, the pharmaceutical composition is administered subcutaneously or intravenously every 2-6 weeks, with a dose of about 3.0 mg/kg. In certain embodiments, the pharmaceutical composition is administered subcutaneous or intravenously every 2-6 weeks, with a dose of from about 2.0 mg/kg to about 10.0 mg/kg.

In some embodiments, the pharmaceutical composition is administered subcutaneously or intravenously weekly or every 2 weeks, with a dose of about 25 mg, 50 mg, 75 mg, 100 mg, 125 mg, 150 mg, 175 mg, 200 mg, 225 mg, 250 mg, 275 mg, or 300 mg.

In one exemplary embodiment, the pharmaceutical composition is administered subcutaneously weekly or every 2 weeks. In certain embodiments, the pharmaceutical composition is administered subcutaneously weekly, with a dose of about 2 mg/kg. In certain embodiments, the pharmaceutical composition is administered subcutaneously weekly, with a dose of about 150 mg.

In certain embodiments, the pharmaceutical composition is administered intravenously or subcutaneously every 2-6 weeks, with a dose of about 10.0 mg/kg. In certain embodiments, the pharmaceutical composition is administered subcutaneous or intravenously every 2-6 weeks, with a dose of from about 1.0 mg/kg to about 10.0 mg/kg.

In one exemplary embodiment, the pharmaceutical composition is administered intravenously every month.

The recombinant ROBO2 protein of the invention can be used as monotherapy or in combination with other therapies to treat, e.g., a renal disease. Other therapies for treating real disease are well-known in the art and are not listed herein.

5. Kits

The invention also provides kits or an article of manufacture comprising a recombinant ROBO2 protein of the invention, and instructions for use. Accordingly, in some embodiments, the disclosure provides a kit or an article of manufacture, comprising a container, a composition within the container comprising a recombinant ROBO2 protein, and a package insert containing instructions to administer a therapeutically effective amount of the recombinant ROBO2 protein for treatment of a patient in need thereof.

In certain embodiments, the kit can contain both a first container having a dried protein and a second container having an aqueous formulation. In certain embodiments, kits containing single and multi-chambered pre-filled syringes (e.g., liquid syringes and lyosyringes) are included.

The instructions relating to the use of recombinant ROBO2 proteins of the invention generally include information as to dosage, dosing schedule, and route of administration for the intended treatment. The containers may be unit doses, bulk packages (e.g., multi-dose packages) or sub-unit doses. Instructions supplied in the kits of the invention are typically written instructions on a label or package insert (e.g., a paper sheet included in the kit), but machine-readable instructions (e.g., instructions carried on a magnetic or optical storage disk) are also provided.

The kits of this invention are in suitable packaging. Suitable packaging includes, but is not limited to, vials, bottles, jars, flexible packaging (e.g., sealed Mylar or plastic bags), and the like. Also contemplated are packages for use in combination with a specific device, such as an inhaler, nasal administration device (e.g., an atomizer) or an infusion device such as a minipump. A kit may have a sterile access port (for example the container may be an intravenous solution bag or a vial having a stopper pierceable by a hypodermic injection needle). The container may also have a sterile access port (for example the container may be an intravenous solution bag or a vial having a stopper pierceable by a hypodermic injection needle). The container may further comprise a second pharmaceutically active agent.

Kits may optionally provide additional components such as buffers and interpretive information. Normally, the kit comprises a container and a label or package insert(s) on or associated with the container.

6. Biological Deposit

Representative materials of the present invention were deposited in the American Type Culture Collection, 10801 University Boulevard, Manassas, Va. 20110-2209, USA, on Feb. 23, 2017. Vector ROBO2-Fc 2.2 having ATCC Accession No. PTA-124008 comprises a DNA insert encoding SEQ ID NO: 1. The deposits were made under the provisions of the Budapest Treaty on the International Recognition of the Deposit of Microorganisms for the Purpose of Patent Procedure and Regulations thereunder (Budapest Treaty). This assures maintenance of a viable culture of the deposit for 30 years from the date of deposit. The deposit will be made available by ATCC under the terms of the Budapest Treaty, and subject to an agreement between Pfizer Inc. and ATCC, which assures permanent and unrestricted availability of the progeny of the culture of the deposit to the public upon issuance of the pertinent U.S. patent or upon laying open to the public of any U.S. or foreign patent application, whichever comes first, and assures availability of the progeny to one determined by the U.S. Commissioner of Patents and Trademarks to be entitled thereto according to 35 U.S.C. Section 122 and the Commissioner's rules pursuant thereto (including 37 C.F.R. Section 1.14 with particular reference to 886 OG 638).

Pfizer Inc., an Applicant of the present application has agreed that if a culture of the materials on deposit should die or be lost or destroyed when cultivated under suitable conditions; the materials will be promptly replaced on notification with another of the same. Availability of the deposited material is not to be construed as a license to practice the invention in contravention of the rights granted under the authority of any government in accordance with its patent laws.

EXAMPLES

Exemplary methods and materials are described herein, although methods and materials similar or equivalent to those described herein can also be used in the practice or testing of the present invention. The materials, methods, and examples are illustrative only and not intended to be limiting.

Example 1. Generation of ROBO2-Fc 2.2

Selection of ROBO2-Fc 2.2 Through Design of Multiple ROBO2-Fc Fusion Proteins

In order to select the optimal ROBO2-Fc ligand trap, multiple proteins were generated consisting of varying lengths of the ROBO2 extracellular domain fused to an IgG1 Fc domain through a glycine-serine (GS) linker. Studies have shown that for the ROBO1 and ROBO2 receptors their Ig1 domain is sufficient to bind to the D2 leucine rich repeat (LRR) domain of SLIT ligands. ROBO2 contains 5 Ig domains (Ig 1-5). Selection criteria first focused on generating a ROBO2-Fc fusion protein with the minimal ROBO2 sequence that could bind SLIT2 and then focused on optimizing that molecule for recombinant protein expression in HEK 293 cells. Initially, 4 DNA constructs were generated for expression of polypeptide sequences consisting of the Ig1 domain (ROBO2-Fc 1.0; SEQ ID NO: 5), Ig1 and Ig2 domains (ROBO2-Fc 2.0; SEQ ID NO: 3), Ig1, Ig2, and Ig3 domains (ROBO2-Fc 3.0; SEQ ID NO: 6), and Ig1, Ig2, Ig3, and Ig4 domains (ROBO2-Fc 4.0; SEQ ID NO: 7) fused to the Fc portion of human IgG1 through a GS linker (Table 23). Expression of the constructs was driven by the Ig leader (SEQ ID NO: 18). The ROBO2-Fc 1.0, 2.0 and 3.0 proteins did not bind SLIT2. ROBO2-Fc 4.0 did bind. In order to minimize the ROBO2 portion of the Fc fusion more proteins were generated including a version with the Ig1 domain comprising at the C-terminal the Ig1-Ig2 inter-domain linker (SEQ ID NO: 10) (ROBO2-Fc 1.1; SEQ ID NO: 4). Another construct involved including the Ig1 and Ig2 domains and the Ig2-Ig3 inter-domain linker (VFER (SEQ ID NO: 12)) (ROBO2-Fc 2.1; SEQ ID NO: 2). Addition of VFER (SEQ ID NO: 12) at the C-terminus of the Ig1-Ig2 domains, to create the ROBO2-Fc 2.1 protein, enabled robust binding to SLIT2 (FIG. 3). ROBO2-Fc 1.1 did not bind SLIT2. Utilizing the Octet Red, ROBO2-Fc proteins were loaded onto anti human-Fc (AHC) sensors at 10 ug/ml and incubated with 100 nM SLIT2 for 7 minutes and then the sensors were moved to buffer alone for 640 seconds. ROBO2-Fc 4.0 was included as a positive control for binding.

Recombinant protein expression of ROBO2-Fc 2.1 in HEK 293 cells was very poor (3 µg/ml). In order to increase expression, the ROBO2 pre-Ig1 sequence (SEQ ID NO: 8) was added and the ROBO2 leader sequence (SEQ ID NO: 17) was also included to the ROBO2-Fc 2.1 expression construct to create the ROBO2-Fc 2.2 expression construct. The ROBO2 leader sequence (SEQ ID NO: 17) is cleaved during protein production to produce mature ROBO2-Fc 2.2. Addition of the ROBO2 pre-Ig1 sequence (SEQ ID NO: 8) increased protein expression over 25-fold compared to expression of an otherwise identical expression construct not encoding the pre-Ig1 sequence SRLRQEDFP (SEQ ID NO: 8) in an otherwise identical host cell. The increased expression did not affect the biological activity of ROBO2-Fc 2.2 which still bound SLIT2 with high affinity (FIGS. 3-4A-C).

Example 2. Characterization of ROBO2-Fc 2.2 Binding and Neutralizing Activities

ROBO2-Fc 2.2 was screened in numerous assays for SLIT2-N binding, neutralization of SLIT2-N binding, and inhibition of SLITx-N functional activity. ROBO2-Fc 2.2 binding to SLIT2 was assessed in two ways; first, by surface plasmon resonance (SPR), and second, using a cell based flow cytometry assay to detect ROBO2-Fc 2.2 binding to cell expressed human SLIT2-N.

SPR Analysis

Human SLIT2 shares a high level of homology with cynomolgus monkey SLIT2; the overall homology is 99% and homology in the leucine-rich repeat domain 2 (D2) of SLIT2 that contains the ROBO2 binding site is 100%. Similar to cynomolgus monkey, human and rat SLIT2 share a high degree of homology with overall sequence identity and within the D2 binding domain being 97%. Binding of ROBO2-FC 2.2 to the N terminal fragment of human and rat SLIT2 which contains the D2 region (SLIT2-N), and the specific SLIT2 D2 domain of human and cynomolgus monkey (100% identical) was assessed by SPR. For each cycle of the kinetic titration experiment (FIGS. 4A-4C), the ROBO2-Fc 2.2 molecule was non-covalently captured by Anti-Human Fc (AHFc) attached to a C1 chip, which bound to the human IgG1 Fc region of ROBO2-Fc 2.2. The captured ROBO2-Fc 2.2 was then exposed to varying concentrations of the SLIT2 ligands to monitor association and dissociation kinetics. ROBO2-Fc 2.2 was diluted to 2 nM. HBS-EP was used as a diluent. Human/cynomolgus monkey SLIT2-D2, human SLIT2-N and rat SLIT2-N were diluted to 2 nM in HBS-EPB from their stock concentrations. An 8 point 2-fold dilution series was performed on the SLIT2 ligands, ranging from 2 nM to 15.6 pM using HBS-EPB as the diluent. ROBO2-Fc 2.2 was captured until a reading of 10-15 RU equivalents and then exposed to titrated amounts of a specific SLIT2 analyte, (i.e. human/cynomolgus monkey SLIT2-D2, human SLIT2-N, or rat SLIT2-N). Association of the indicated SLIT2 ligand was followed for 120s and dissociation monitored for 180s. The apparent binding affinity was determined using a simple 1:1 interaction model of the kinetic rate constants. The $K_D$ of ROBO2-Fc 2.2 binding to human/cynomolgus monkey SLIT2-D2 (ROBO2 binding domain, 100% identical) was determined to be 0.293 nM (FIG. 4A). The $K_D$ of ROBO2-Fc 2.2 binding to human SLIT2-N(N terminal fragment) was determined to be 0.279 nM (FIG. 4B), and, finally, the $K_D$ of ROBO2-Fc 2.2 binding to rat SLIT2-N was determined to be 0.543 nM (FIG. 4C).

Flow Cytometry Assay

ROBO2-Fc 2.2 was conjugated to Alexa Fluor (AF) 647 according to the manufacturer's instructions. Human embryonic kidney (HEK293) overexpressing human SLIT2-N were re-suspended in buffer containing 5% fetal bovine serum in preparation for staining. To stain cells with ROBO2-Fc 2.2-AF647, 2× stocks were prepared and an 11-12 point, 2-fold dilution series was made in fluorescence-activated cell sorting (FACS) buffer. Cells and the relevant dilution of ROBO2-Fc 2.2-AF647 were combined in a 96-well u-bottomed plate and incubated at 4° C. for 45 minutes. After incubation, 150 µL of FACS buffer was added per well to wash the cells. After washing, cells were resuspended in buffer for data acquisition on a Fortessa Flow Cytometer. Data was analyzed using FlowJo software and are represented as geometric mean fluorescence intensity (Geo MFI) of SLIT2-N expressing HEK293 cells minus the Geo MFI of control HEK293 cells. ROBO2-Fc 2.2 binds to human SLIT2-N overexpressed on HEK293 cells in a dose-dependent manner with high affinity having an $EC_{50}$ of 9 nM (FIG. 5).

Homogenous Time Resolved Fluorescence (HTRF) Assay

ROBO2-Fc inhibits binding of a SLIT ligand, such as SLIT2, to a cellular ROBO2 receptor likely by acting as a ligand trap. A ROBO2-SLITx-N HTRF dye labeling assay was used to assess the ability of ROBO2-Fc 2.2 to neutralize SLIT ligand binding to human ROBO2. In this assay, terbium (Tb) labeled (donor), SNAP-tagged (SNAP-Tag® New England Biolabs; see also, Keppler et al., 2003, Nat. Biotechnol. 21:86) human ROBO2 expressing HEK293 cells were incubated with 5 nM d2-labeled (acceptor) SLITx-N from various species (prepared using a Cisbio d2 dye labeling kit according to manufacturer's instructions), in the presence of titrated amounts of ROBO2-Fc 2.2 for 1 hour. After incubation, fluorescence at 665 nm and 620 nm was measured on an Envision multilabel plate reader. The HTRF Ratio was calculated as follows: fluorescence at 665 nm/fluorescence at 620 nm×10,000. Maximal signal was defined as the HTRF ratio of Tb-labeled ROBO2 cells with d2-labeled SLIT2-N in the absence of ROBO2-Fc 2.2, the minimum signal was defined as the HTRF ratio of Tb-labeled ROBO2 expressing HEK293 cells only. Neutralization of 3 different SLIT ligands (SLIT1-N, SLIT2-N and SLIT3-N) from several species, including human, cynomolgus monkey, rabbit, rat and mouse, were used in the assay. The $IC_{50}$ for each SLITx-N was determined using an 11-point, 4-fold dilution series with a top concentration of 4000 nM. The geometric mean of the $IC_{50}$ across 3 independent experiments was calculated and is summarized for all the ligands evaluated (Table 2).

TABLE 2

Summary Table of Results for ROBO-Fc 2.2 Inhibition of the SLITx-N:human ROBO2 HTRF Assay

| SLIT Ligand | Species | $IC_{50}$ (Geo Mean, nM) | 95% CI (nM) | n |
|---|---|---|---|---|
| SLIT1-N | Human | 5.9 | 4.4-8.0 | 3 |
| SLIT1-N | Cynomolgus Monkey | 6.5 | 4.8-8.9 | 3 |
| SLIT1-N | Rabbit | 9.8 | 6.4-15.0 | 3 |
| SLIT1-N | Rat | 8.3 | 5.5-12.5 | 3 |
| SLIT2-N | Human | 3.9 | 1.5-10.6 | 4 |
| SLIT2-N | Rabbit | 5.7 | 2.9-10.9 | 3 |
| SLIT2-N | Mouse | 5.4 | 4.6-6.4 | 3 |
| SLIT3-N | Human | 5.1 | 3.5-7.4 | 3 |
| SLIT3-N | Cynomolgus Monkey | 3.6 | 2.0-6.4 | 3 |
| SLIT3-N | Rabbit | 10.2 | 7.5-13.9 | 3 |
| SLIT3-N | Rat | 3.0 | 1.7-5.2 | 3 |
| SLIT3-N | Mouse | 4.3 | 2.2-8.5 | 3 |

CI = confidence interval; Geo Mean = geometric mean; HTRF = Homogenous time resolved fluorescence; $IC_{50}$ = Inhibitory concentration at 50% activity; n = Number of determinations; ROBO2 = Roundabout guidance receptor 2; SLIT = Slit guidance ligand; x = 1, 2 or 3.

The dose-dependent inhibition of SLIT ligand binding from various species to human ROBO2 by ROBO2-Fc 2.2 as assessed by HTRF. The $IC_{50}$ was determined using an 11-point, 4-fold dose titration of ROBO-Fc 2.2 in the HTRF assay against a panel of human, cynomolgus monkey, rabbit, rat or mouse SLIT ligands. ROBO2-Fc 2.2 was a potent neutralizer of human, cynomolgus monkey, rabbit and rat SLIT1-N binding to human ROBO2 with $IC_{50}$s ranging from a low of 5.9 nM (human) to a high of 9.8 nM (rabbit); ROBO2-Fc 2.2 also demonstrated dose dependent inhibition of SLIT2-N binding to human ROBO2 with the $IC_{50}$s ranging from 3.9 nM (human) to 5.7 nM (rabbit). ROBO2-Fc 2.2 was a potent neutralizer of SLIT3-N binding to human ROBO2 with $IC_{50}$s ranging from 3.6 nM (cynomolgus monkey) to 10.2 nM (rabbit). Finally, ROBO2-Fc 2.2 was a potent neutralizer of both human SLIT2-N:human ROBO2 (FIG. 6A) and rat SLIT2-N:human ROBO2 (FIG. 6B) binding with an $IC_{50}$ of 7 nM or 4 nM, respectively.

Neuronal Cell Migration Assay

Figure 7:
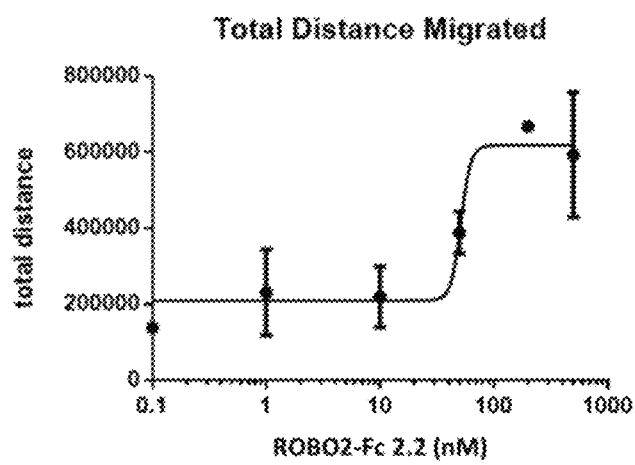
FIG. 7 depicts the dose-dependent inhibition of SLIT2-N mediated inhibition of neuronal cell migration by ROBO2-Fc 2.2. Subventricular zone (SVZ) neuronal tissue cell explants were cultured overnight in the presence of 1 nM SLIT2-N and a dose range of ROBO2-Fc 2.2. ROBO2-Fc 2.2 was able to restore neuronal cell migration in a dose-dependent manner with an $IC_{50}$ of 51 nM.

The final selection screen was functional neutralization of ROBO2-dependent SLIT2-N activity. SLIT2-ROBO2 interactions are key regulators of axonal migration during development. It is known that SLIT2 is chemo-repulsive to subventricular zone neurons and that this activity is ROBO2 dependent. Neuronal tissue explants from the subventricular zone (SVZ) of rats were isolated and embedded in a collagen matrix. In the presence of SLIT2-N, neuronal cell migration is inhibited (SVZ assay); tissue explants were incubated in the presence of 1 nM SLIT2-N with or without titrated amounts of ROBO2-Fc 2.2. After incubation, cells were fixed with 4% paraformaldehyde and stained with Hoechst 33342. Wide-field fluorescence images were acquired on the Operetta High Content Imager (Perkin Elmer) with a 10× high NA objective. Nine fields per well with 5% overlap were taken to capture the entire center area of the well. A Z-stack for each field was acquired consisting of 6 planes with 1 μm distance between each plane to capture the full depth of the tissue explant. Analysis was performed in Volocity software (Perkin Elmer). All fields in each well were stitched together. The area of the tissue explant in the center and each nucleus outside of the tissue explant were detected by Hoechst 33342 staining. Individual nuclei were counted and the distance of the center of each nucleus to the closest edge of the tissue explant was measured in μm. The mean migration distance of nuclei in the well was multiplied by the nuclei count to obtain the total migration distance for each well. ROBO2-Fc 2.2 was able to restore neuronal cell migration in a dose-dependent manner with an $IC_{50}$ of 51 nM (FIG. 7). These results demonstrate that ROBO2-Fc 2.2 can not only inhibit the binding of SLIT2 to ROBO2, but also has a potent dose-dependent neutralizing effect on the ROBO2-dependent SLIT2 chemo-repulsive activity for SVZ neurons.

Example 3. In Vivo Effects of Novel ROBO2 Proteins

Figure 8:
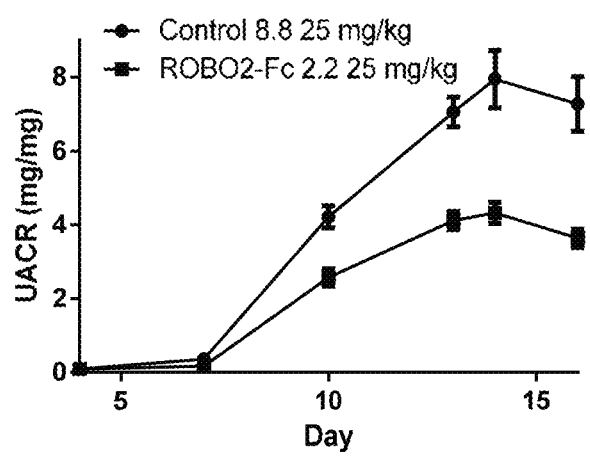
FIG. 8 demonstrates inhibition of proteinuria with treatment of ROBO2-Fc 2.2 in the rat Passive Heymann Nephritis model with an exemplary prophylactic dosing regimen. Twelve animals in each of the indicated groups were treated subcutaneously with the indicated dose of ROBO2-Fc 2.2 or an irrelevant isotype control monoclonal antibody (control) every three days starting the day before the induction of the model on day 0. The Y axis indicates the ratio of urine albumin to creatinine (mg/mg) as a measure of leakage of protein into the urine, indicative of podocyte damage. Lewis rats were injected with sheep anti-sera raised against rat kidney brush border (anti-Fx1a, basement membrane and podocytes). The rats developed an immune response to the sheep sera which bound the rat podocytes. As podocytes are damaged and effaced, proteinuria increases. Treatment with the highest dose of ROBO2-Fc 2.2 at 25 mg/kg reduced proteinuria 45% maximally with a p value less than 0.001 by repeated measure ANOVA statistical analyses compared to the control antibody treatment. The dose effect was also statistically significant with a p value less than 0.001.
Figure 9:
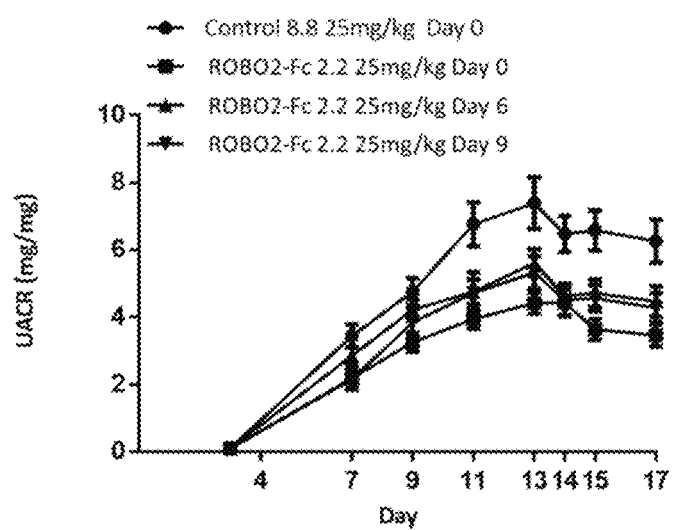
FIG. 9 demonstrates inhibition of proteinuria with treatment of ROBO2-Fc 2.2 in the rat Passive Heymann Nephritis model with an exemplary therapeutic dosing regimen. Twelve animals in each of the indicated groups were treated subcutaneously with the indicated dose of ROBO2-Fc 2.2 or an irrelevant control monoclonal antibody (control) every three days with the following dosing regimen: control antibody was administered on day 0 (circles) and ROBO2-Fc 2.2 was administered on day 0 (squares), day 6 (triangles) or day 9 (inverted triangles). The Y axis indicates the ratio of urine albumin to creatinine (mg/mg) as a measure of leakage of protein into the urine, indicative of podocyte damage. Lewis rats were injected with sheep anti-sera raised against rat kidney brush border (anti-Fx1a, basement membrane and podocytes). The rats developed an immune response to the sheep sera which bound the rat podocytes. As podocytes are damaged and effaced, proteinuria increased. Treatment with ROBO2-Fc 2.2 administered on day 0, 6 and 9 reduced proteinuria to a similar extent, 40% maximally and with a p value less than 0.001 by repeated measure ANOVA statistical analyses for each ROBO2-Fc 2.2 treated group compared to the control antibody treatment.

Passive Heymann's Nephritis is a rat model of nephrotoxic injury affecting glomerular podocytes, leading to an increase in proteinuria. This model was used to assess the efficacy of ROBO2-Fc 2.2 to reduce proteinuria. Treatment of rats with ROBO2-Fc 2.2 not only reduced proteinuria but also protected podocyte foot process architecture. As shown in FIG. 8 and FIG. 9, treatment of rats with either a prophylactic or therapeutic dosing regimen of ROBO2-Fc 2.2 reduced the amount of proteinuria. Lewis rats were injected with sheep antisera raised against rat kidney brush border (anti-Fx1a (Probetex Inc, basement membrane and podocytes). The rats develop an immune response to the sheep sera. Complement activation leads to podocyte effacement and an increase in proteinuria between day 3 and 12 followed by a plateau. This mechanism closely resembles that found in Membranous Nephropathy where autoantibodies against the podocyte protein PLA2R (in 70% of cases) cause podocyte effacement and nephrotic range proteinuria following complement engagement. Rats were pretreated 24 hours before the administration of sheep antisera with a dose range to cover approximately 50, 90 and 99% (1, 5, and 25 mg/kg) of glomerular ROBO2 and every 72 hours thereafter (prophylactic dosing regimen). For the therapeutic dosing regimen ROBO2-Fc 2.2 was administered on day 6 or day 9 (5 or 8 days after administration of sheep antisera), a dose given 24 hours prior to the administration of sheep antisera was also included in the study. The maximal reduction in proteinuria was 45% when treatment began prophylactically (FIG. 8) and a repeated measures ANOVA statistical analysis confirmed the dose response with a p value less than 0.001. Treatment with ROBO2-Fc 2.2 administered on day 0, 6 and 9 reduced proteinuria to a similar extent (FIG. 9), 40% maximally and with a p value less than 0.001 by repeated measure ANOVA statistical analyses for each ROBO2-Fc 2.2 treated group compared to the control antibody treatment. There was no reduction in immune complex deposition in the kidney as determined by complement IHC scoring, indicating the response was due to a podocyte protective effect.

To further provide confidence in the modulation of podocyte function and structure, quantitative analysis of electron micrographs of podocyte substructure was performed as described below.

Collection, Sampling, and Sectioning

Full face sample kidneys (one kidney per animal) fixed by immersion (4% formaldehyde/1% glutaraldehyde) were received, trimmed to include just the cortex, and five samples of each kidney were embedded in epoxy resin. The first embedded sample of each kidney was sectioned. If it contained three glomeruli the sample was thin sectioned and imaged. If this first sample did not contain glomeruli, the other embedded samples from that kidney were sequentially sectioned and similarly evaluated to find a sample with three glomeruli.

Viewing and Imaging

Selected kidney samples were digitally imaged using a transmission electron microscope (Hitachi H-7100) and a digital CCD camera system (Advanced Microscopy Techniques, Danvers, Mass.). Without repetition, three capillary loops of the first three glomeruli found at 200× magnification, were imaged at 5,000× and 10,000× magnification. This resulted in 18 digital images per kidney (i.e., three glomeruli per kidney sample × three areas per glomerulus×2 magnifications). To allow evaluation in a blinded fashion, each image was identified only with study number, animal number, sample number, and magnification.

Podocyte Foot Process Width and Slit-Diaphragm Density Measurement

ImageJ software (version 1.47v; National Institutes of Health, Bethesda, Md., USA) was used to manually trace and measure the width of foot processes adjacent to per unit length of the glomerular basement membrane (GBM) on high magnification transmission electron microscopy images. Briefly, measurements were carried out in six rats per group and nine 5000×TEM images from each rat. The podocyte foot process width was measured from one end of the slit diaphragm to the other by drawing a line parallel to the GBM. This was repeated for all the foot processes of the image. These results were then adjusted for scale bar and the harmonic mean for each image was calculated.

Slit diaphragm density: The slit diaphragm density was calculated by counting the number of slit diaphragms and divided by the total GBM length spanning the area of these slit diaphragms. Briefly, measurements were carried out in six rats per group and nine 5000×TEM images from each rat. The density was calculated by dividing the number of slit diaphragms to the GBM length. If more than one GBM area was visible or the GBM was disconnected due to non-visibility of the foot processes, the above procedure was repeated and average of these measurements were used to calculate the slit diaphragm density. The distance between slit diaphragms of interdigitating foot processes was calculated across multiple capillary loops, determining the average foot process width. The foot process width of an effaced podocyte will be larger than that of a normal uneffaced podocyte.

Figure 10A:
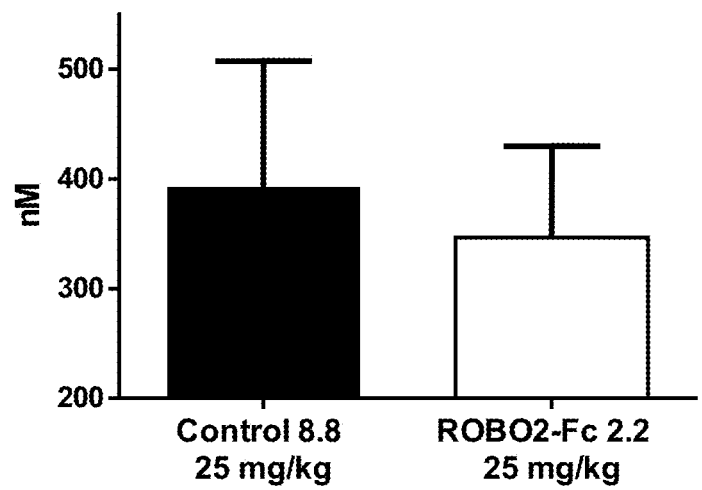
FIGS. 10A-10B demonstrate that treatment with ROBO2-Fc 2.2 reduces damage to podocyte substructure in the Passive Heymann Nephritis Model. Twelve animals in each of the indicated groups were treated subcutaneously with the indicated dose of ROBO2-Fc 2.2 or an irrelevant control monoclonal antibody every three days at 25 mg/kg to achieve 100% target coverage starting the day before the induction of the model on day 0. Following animal sacrifice at day 16, selected kidney samples were digitally imaged using a transmission electron microscope. Without repetition, three capillary loops of the first three glomeruli found at 200× magnification, were imaged at 5000× and 10,000× magnification. ImageJ software (version 1.47v; National Institutes of Health, Bethesda, Md., USA) was used to manually trace and measure the width of adjacent foot processes as well as the density of slit diaphragms per unit length of the glomerular basement membrane (GBM) on high magnification transmission electron microscopy images. Samples were analyzed over 3 separate experiments. The podocyte foot processes of the ROBO2-Fc 2.2 treated animal were significantly shorter than the control antibody treated animals (FIG. 10A), and the density of slit diaphragms was significantly higher in ROBO2-Fc 2.2 treated animals (FIG. 10B; p value less than 0.01 by two tailed T test) indicating that they were less effaced and were protected from the glomerular insult.
Figure 10B:
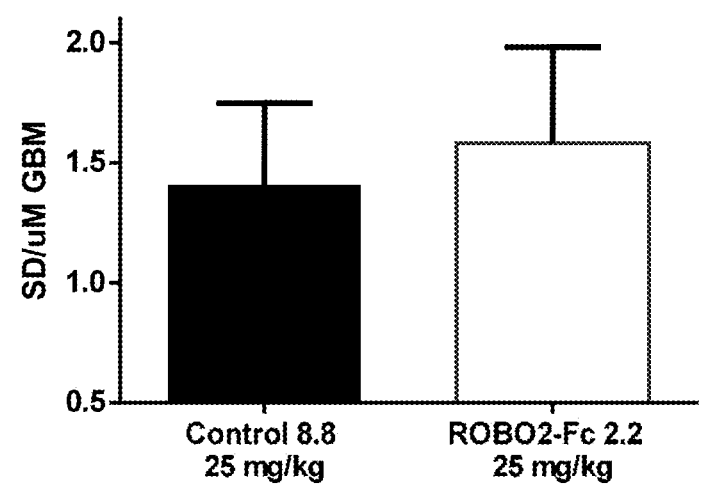

As shown in FIG. 10A, the foot process width of the ROBO2-Fc 2.2 treated animals at the 25 mg/kg dose was significantly shorter that the control antibody treated animals. These data demonstrate that the reduction of proteinuria was due to an alteration in podocyte substructure. Additionally, as shown in FIG. 10B, the treatment with ROBO2-Fc 2.2 increased the density of slit diaphragms (p value less than 0.01 by two tailed T test) indicating that they were less effaced and protected from the glomerular insult.

These results demonstrate that ROBO2-Fc 2.2 is efficacious at inhibiting two hallmarks of glomerular disease: proteinuria and diffuse podocyte effacement. Thus, these results support the use of ROBO2-Fc 2.2 as a potential therapeutic to treat glomerular diseases, such as, but not limited to, Focal Segmental Glomerulosclerosis (FSGS).

The key pharmacologic properties for ROBO2-Fc 2.2 are summarized in Table 3.

TABLE 3

Summary of Key Pharmacologic Properties of ROBO2-Fc 2.2

| Assay | Pharmacodynamic Activity |
|---|---|
| In Vitro Assays | |
| Surface Plasmon Resonance | |
| Human and Cynomolgus Monkey SLIT2-D2 | KD = 293 ± 70 pM |
| Human SLIT2-N | KD = 279 ± 37 pM |
| Rat SLIT2-N | KD = 543 ± 72 pM |
| Cell Based Binding Assays (Flow Cytometry) | |
| Human SLIT2-N Homogenous Time Resolved Fluorescence | EC50 = 8.6 ± 5.0 nM |
| Human SLIT2-N | IC50 = 7.0 ± 3.9 nM |
| Rat SLIT2-N | IC50 = 4.0 ± 0.7 nM |
| In Vivo Assay | |
| Rat Passive Heymann's Nephritis | Dosing prior to nephrotoxic injury or on Day 6 or 9 (5 or 8 days after injury) significantly reduced proteinuria |

In vitro pharmacology studies demonstrated that ROBO2-Fc 2.2 bound with the same high affinity to human SLIT2-N and the identical human and cynomolgus monkey SLIT2-D2 domain. ROBO2-Fc 2.2 bound to the rat SLIT2-N with high affinity as well. ROBO2-Fc 2.2 bound cells expressing human SLIT2-N in a dose-dependent manner. Additionally, ROBO2-Fc 2.2 potently inhibited the binding of rat and human SLIT2-N to human ROBO2 in a cell-based binding HTRF assay. In vivo mechanistic, pharmacology, and efficacy studies were also conducted using a rat model of proteinuric glomerular disease. Administration of ROBO2-Fc 2.2, in either a prophylactic or therapeutic dosing regimen, led to a statistically significant reduction of proteinuria in the PHN model. These results support the use of ROBO2-Fc 2.2 to treat glomerular diseases such as Focal Segmental Glomerulosclerosis (FSGS).

Example 4. Characterization of ROBO2-Fc S17T/R73Y Binding and Neutralizing Activities Flow Cytometry Assay ROBO2-Fc S17T/R73Y was conjugated to Alexa Fluor (AF) 647 according to the manufacturer's instructions. Cells overexpressing human SLIT2-N were resuspended in buffer containing 5% fetal bovine serum in preparation for staining. To stain cells with ROBO2-Fc S17T/R73Y-AF647, 2× stocks were prepared and an 11-12 point, 2-fold dilution series was made in FACS buffer. Cells and the relevant dilution of ROBO2-Fc S17T/R73Y-AF647 were combined in a 96-well u-bottomed plate and placed at 4° C. for 45 minutes. After incubation, 150 µL of FACS buffer was added per well to wash the cells. After washing, cells were resuspended in buffer for data acquisition on a Fortessa Flow Cytometer. Data was analyzed using FlowJo software and are represented as geometric mean fluorescence intensity (Geo MFI) of SLIT2-N expressing HEK293 cells—the Geo MFI of control HEK293 cells. ROBO2-Fc S17T/R73Y bound to human SLIT2-N overexpressed on human embryonic kidney (HEK293) cells with high affinity having an $EC_{50}$ of 2.5 nM (FIG. 11).

Homogenous Time Resolved Fluorescence (HTRF) Assay

A ROBO2-SLIT2-N homogenous time resolved fluorescence (HTRF) assay was used to assess the ability of ROBO2-Fc S17T/R73Y to block the interaction of SLIT2-N and cell expressed ROBO2. In this assay, terbium (Tb) labeled (donor), SNAP-tagged ROBO2 expressing HEK293 cells were incubated with 5 nM d2-labeled (acceptor) human SLIT2-N in the presence of titrated amounts of ROBO2-Fc S17T/R73Y for 1 hour per manufacturer's instructions (Cisbio HTRF d2 Labeling kit 62D2DPEA and Terbium Cryptate Labeling kit 62TBSPEA). After incubation, fluorescence at 665 nm and 620 nm was measured on an Envision multilabel plate reader. The HTRF Ratio was calculated as follows: fluorescence at 665 nm/fluorescence at 620 nm×10,000. Maximal signal was defined as the HTRF ratio of Tb-labeled ROBO2 cells with d2-labeled SLIT2-N in the absence of ROBO2-Fc S17T R73Y, the minimum signal was defined as the HTRF ratio of Tb-labeled ROBO2 expressing HEK293 cells only. ROBO2-Fc S17T R73Y was a potent neutralizer of human SLIT2-N:human ROBO2 binding with an $IC_{50}$ of 1.4 nM (FIG. 12).

Neuronal Cell Migration Assay

As was done for ROBO2-Fc 2.2, ROBO2-Fc S17T/R73Y was evaluated for the ability to reverse SLIT2-N mediated inhibition of neuronal cell migration in a dose-dependent manner. Neuronal tissue explants from the subventricular zone (SVZ) of rats were isolated and embedded in a collagen matrix. In the presence of SLIT2-N, neuronal cell migration is inhibited (SVZ assay); tissue explants were incubated in the presence of 1 nM SLIT2-N with or without titrated amounts of ROBO2-Fc S17T R73Y. After incubation, cells were fixed with 4% paraformaldehyde and stained with Hoechst 33342. Wide-field fluorescence images were acquired on the Operetta High Content Imager (Perkin Elmer) with a 10× high NA objective. Nine fields per well with 5% overlap were taken to capture the entire center area of the well. A Z-stack for each field was acquired consisting of 6 planes with 1 µm distance between each plane to capture the full depth of the tissue explant. Analysis was performed using Volocity software (Perkin Elmer). All fields in each well were stitched together. The area of the tissue explant in the center and each nucleus outside of the tissue explant were detected by Hoechst 33342 staining. Individual nuclei were counted and the distance of the center of each nucleus to the closest edge of the tissue explant was measured in µm. The mean migration distance of nuclei in the well was multiplied by the nuclei count to obtain the total migration distance for each well. ROBO2-Fc S17T/R73Y was able to restore neuronal cell migration in a dose-dependent manner with an $IC_{50}$ of 11.5 nM (FIG. 13).

These results demonstrate that like ROBO2-Fc 2.2, ROBO2-Fc S17T/R73Y can not only inhibit the binding of SLIT2 to ROBO2, but also has a potent dose-dependent neutralizing functional effect on the ROBO2-dependent SLIT2 chemo-repulsive activity for SVZ neurons. Thus, these data suggest that like ROBO2-Fc 2.2, ROBO2-Fc S17T/R73Y can be a potential therapeutic that may be useful to treat glomerular diseases involving ROBO2-SLIT interaction, such as, Focal Segmental Glomerulosclerosis (FSGS).

Example 5. Structural Analysis of ROBO2-Fc 2.2

Material Preparation, Crystallization, Data Collection, and Structure Determination:

Expression and Purification of a ROBO2-His Construct

A ROBO2 construct consisting of the ROBO2 pre-Ig1 sequence (SEQ ID NO: 8), Ig1 domain, Ig2 domain and the ROBO2 Ig2-3 inter-domain linker (SEQ ID NO: 12) with a 6× histidine tag (SEQ ID NO: 25) at the C-terminus (ROBO2-His ("His6" disclosed as SEQ ID NO: 25)) was expressed in HEK293 cells. The construct was purified through Ni Excel column with imidazole gradient elution. The construct was further purified to homogeneity via size exclusion chromatography using HiLoad 26/200 Superdex 200 (GE Healthcare).

Crystallization

Crystals of ROBO2-His were obtained under the following condition: 100 mM Sodium Citrate pH 4.5, 12% PEG8000, which yielded crystals that diffracted to 2.19 Å.

Data Collection

Crystals were transiently cryo-protected and synchrotron data collection was performed remotely at Advanced Photon Source (APS). Image frames were processed using software AutoPROC (Global Phasing Ltd). The data belongs to space group $P2_1$, with unit cells as follows: a=79.307 Å, b=50.887 Å, c=93.854 Å, $\alpha=\gamma=90°$, $\beta=114.92$, with two copies of the human ROBO2 (Ig1+Ig2) per asymmetric unit.

Structure Determination and Refinement

Molecular Replacement searches using homology model of ROBO1 (Ig1+Ig2, PDB code: 2V9Q) yielded convincing solutions of each component. Refinement was performed using software autoBUSTER (Global Phasing Ltd), and the final R/Rfree factors at 2.19 Å are 0.2119 and 0.2425, respectively, with RMSD of bond 0.010 Å, RMSD of angles 1.19°.

Structural Results and Analysis:

Enhancement of Expression Via the ROBO2 Pre-Ig1 Sequence

In Example 1, it has been demonstrated that inclusion of the wild-type ROBO2 pre-Ig1 sequence SRLRQEDFP (SEQ ID NO: 8) drastically improved the level of expression for ROBO2-Fc 2.2. It is evident from the crystal structure of ROBO2-His6 ("His6" disclosed as SEQ ID NO: 25) that Asp7 (D7), Phe8 (F8), and Pro9 (P9) are substantially involved in the interactions vital for structural integrity of ROBO2's first Ig domain (FIG. 14). Asp7 forms a hydrogen bond with Tyr94, while Phe8 forms a double bond with Arg36 and Asn93 (Tables 4-5; distance between the neighboring residues is within a distance of 3.8 Å or less). In addition, Asp7 (D7), Phe8 (F8), and Pro9 (P9) also involve extensive van der Waals' contacts with neighboring residues, rendering more than 50% of their surface areas buried (Tables 6-9). Without wishing to be bound by any particular theory, these data demonstrate that the ROBO2 pre-Ig1 sequence bridges together the two β-sheets of ROBO2's first Ig domain and thereby significantly stabilizes the structural fold of the N-terminal region. Surprisingly, these data suggest that the stabilization of the structural fold mediates the increased expression of the properly folded ROBO2-Fc 2.2 compared with the expression of ROBO2-Fc constructs lacking the pre-Ig1 sequence.

TABLE 4

Hydrogen bonds involving N-terminal residues of ROBO2 (copy1)

| Residue_1 | Residue_1 # | Residue_2 | Residue_2 # | Distance (Å) |
|---|---|---|---|---|
| ASP | 7 | TYR | 94 | 2.73 |
| PHE | 8 | ARG | 36 | 3.3 |
| PHE | 8 | ASN | 93 | 2.84 |
| PHE | 8 | ARG | 36 | 3.01 |

TABLE 5

Hydrogen bonds involving N-terminal residues of ROBO2 (copy2)

| Residue_1 | Residue_1 # | Residue_2 | Residue_2 # | Distance (Å) |
|---|---|---|---|---|
| ASP | 7 | TYR | 94 | 2.58 |
| PHE | 8 | ARG | 36 | 3.14 |
| PHE | 8 | ASN | 93 | 2.97 |
| PHE | 8 | ARG | 36 | 2.79 |

TABLE 6

Minimum distance interaction table for the N-terminal residues of ROBO2 (copy1)

| Residue_1 | Residue_1 # | Residue_2 | Residue_2 # | Distance (Å) |
|---|---|---|---|---|
| GLU | 6 | ARG | 36 | 3.44 |
| ASP | 7 | ARG | 36 | 3.18 |
| ASP | 7 | TYR | 94 | 2.73 |
| ASP | 7 | LEU | 95 | 3.54 |
| PHE | 8 | GLY | 35 | 3.55 |
| PHE | 8 | ARG | 36 | 3.01 |
| PHE | 8 | GLU | 34 | 3.89 |
| PHE | 8 | LEU | 95 | 3.78 |
| PHE | 8 | ASN | 93 | 2.84 |
| PRO | 9 | ASN | 93 | 3.71 |
| PRO | 9 | LEU | 95 | 3.59 |
| PRO | 9 | ARG | 11 | 3.82 |

TABLE 7

Minimum distance interaction table for the N-terminal residues of ROBO2 (copy2)

| Residue_1 | Residue_1 # | Residue_2 | Residue_2 # | Distance (Å) |
|---|---|---|---|---|
| GLU | 6 | ARG | 36 | 3.74 |
| ASP | 7 | ARG | 36 | 3.19 |
| ASP | 7 | TYR | 94 | 2.58 |
| ASP | 7 | LEU | 95 | 3.56 |
| PHE | 8 | GLY | 35 | 3.4 |
| PHE | 8 | ARG | 36 | 2.79 |
| PHE | 8 | GLU | 34 | 3.91 |
| PHE | 8 | LEU | 95 | 3.6 |
| PHE | 8 | ASN | 93 | 2.97 |
| PRO | 9 | ASN | 93 | 3.85 |
| PRO | 9 | LEU | 95 | 3.58 |
| PRO | 9 | ARG | 11 | 3.75 |

TABLE 8

N-terminal residue buried surface area (BSA) analysis (copy1)

| Residue | Residue # | Complex ASA | Free ASA | BSA | BSA % |
|---|---|---|---|---|---|
| GLU | 6 | 197.12 | 218.69 | 21.57 | 9.86 |
| ASP | 7 | 64.6 | 148.81 | 84.21 | 56.59 |
| PHE | 8 | 82.91 | 179.66 | 96.75 | 53.85 |
| PRO | 9 | 80.69 | 173.68 | 92.99 | 53.54 |

TABLE 9

N-terminal residue buried surface area (BSA) analysis (copy2)

| Residue | Residue # | Complex ASA | Free ASA | BSA | BSA % |
|---|---|---|---|---|---|
| GLU | 6 | 191.1 | 216.4 | 25.3 | 11.69 |
| ASP | 7 | 59.52 | 147.69 | 88.17 | 59.7 |
| PHE | 8 | 82.87 | 181.29 | 98.42 | 54.29 |
| PRO | 9 | 78.78 | 172.08 | 93.3 | 54.22 |

Figure 15:
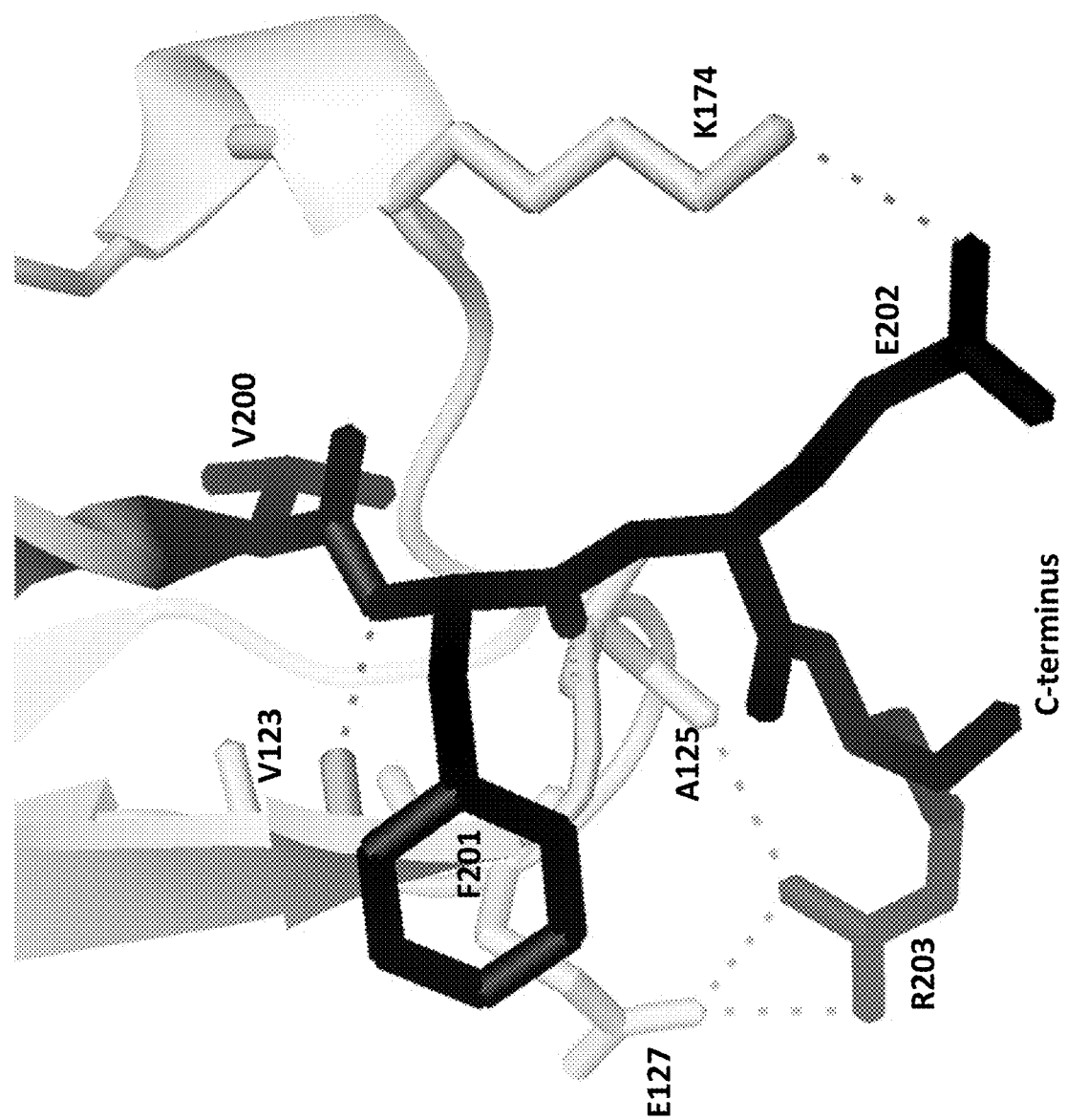
FIG. 15 shows a drawing depicting the crystal structure of the ROBO2-His construct. The crystal structure of ROBO2-His6 ("His6" disclosed as SEQ ID NO: 25) reveals that the ROBO2 Ig2-3 inter-domain linker, Valine200-Phenylalanine201-Glutamic acid202-Arginine203 (SEQ ID NO: 12), effectively stabilizes the structural fold in the C-terminal region of ROBO2's Ig2 domain.

Enhancement of Expression Via the ROBO2 Ig2-3 Inter-Domain Linker:

Inclusion of the ROBO2 Ig2-3 inter-domain linker V200-F201-E202-R203 (VFER; SEQ ID NO: 12) notably increased the expression level of ROBO2-Fc 2.2. Val200 is part of the last β-strand in the Ig2 domain of ROBO2. V200 is deeply encircled by neighboring residues through extensive van der Waals' contacts (Tables 10-11); consequently 85% of its surface area has been buried (Tables 12-13). In addition to Val200, Phe201-Glu202-Arg203 are also substantially involved in hydrogen bonding and van der Waals' interactions within the region (Tables 10-11, 14-15). Collectively, these data suggest that these four amino acid residues effectively stabilize the structural fold in the C-terminal region of ROBO2's Ig2 domain (FIG. 15). Without wishing to be bound by any particular theory, these data suggest that the stabilization of the structural fold increases the expression of the properly folded ROBO2-Fc 2.2 compared with the decreased expression of ROBO2-Fc constructs lacking the Ig2-3 interdomain linker.

TABLE 10

Minimum distance interaction table for the C-terminal residues of ROBO2 (copy1)

| Residue_1 | Residue_1 # | Residue_2 | Residue_2 # | Distance (Å) |
|---|---|---|---|---|
| VAL | 200 | ARG | 173 | 3.66 |
| VAL | 200 | VAL | 123 | 3.17 |
| VAL | 200 | THR | 172 | 3.33 |
| VAL | 200 | LYS | 174 | 3.28 |
| VAL | 200 | ALA | 125 | 3.84 |
| PHE | 201 | LYS | 174 | 3.87 |
| PHE | 201 | VAL | 122 | 3.62 |
| PHE | 201 | ALA | 124 | 3.54 |
| PHE | 201 | ALA | 125 | 2.87 |
| PHE | 201 | VAL | 123 | 2.93 |
| GLU | 202 | LYS | 174 | 3.54 |
| ARG | 203 | ALA | 125 | 3.62 |
| ARG | 203 | GLU | 127 | 3.53 |

TABLE 11

Minimum distance interaction table for the C-terminal residues of ROBO2 (copy2)

| Residue_1 | Residue_1 # | Residue_2 | Residue_2 # | Distance (Å) |
|---|---|---|---|---|
| VAL | 200 | ARG | 173 | 3.55 |
| VAL | 200 | VAL | 123 | 3.27 |
| VAL | 200 | THR | 172 | 3.27 |
| VAL | 200 | LYS | 174 | 3.88 |
| VAL | 200 | ALA | 125 | 3.75 |
| PHE | 201 | VAL | 122 | 3.6 |
| PHE | 201 | ALA | 124 | 3.56 |
| PHE | 201 | ALA | 125 | 2.84 |
| PHE | 201 | VAL | 123 | 2.94 |
| GLU | 202 | LYS | 174 | 3.43 |
| ARG | 203 | ALA | 125 | 3.03 |
| ARG | 203 | GLU | 127 | 3.12 |

TABLE 12

C-terminal residue buried surface area (BSA) analysis (copy1)

| Residue | Residue # | Complex ASA | Free ASA | BSA | BSA % |
|---|---|---|---|---|---|
| VAL | 200 | 21.95 | 207.67 | 185.72 | 89.43 |
| PHE | 201 | 93.47 | 167.02 | 73.55 | 44.04 |

TABLE 12-continued

C-terminal residue buried surface area (BSA) analysis (copy1)

| Residue | Residue # | Complex ASA | Free ASA | BSA | BSA % |
|---|---|---|---|---|---|
| GLU | 202 | 138.33 | 166.75 | 28.42 | 17.04 |
| ARG | 203 | 96.04 | 153.35 | 57.31 | 37.37 |

TABLE 13

C-terminal residue buried surface area (BSA) analysis (copy2)

| Residue | Residue # | Complex ASA | Free ASA | BSA | BSA % |
|---|---|---|---|---|---|
| VAL | 200 | 27.85 | 206.09 | 178.24 | 86.49 |
| PHE | 201 | 99.37 | 171.31 | 71.94 | 41.99 |
| GLU | 202 | 113.98 | 153.45 | 39.47 | 25.72 |
| ARG | 203 | 77.8 | 159.3 | 81.5 | 51.16 |

TABLE 14

Hydrogen bonds involving C-terminal residues of ROBO2 (copy1)

| Residue_1 | Residue_1 # | Residue_2 | Residue_2 # | Distance (Å) |
|---|---|---|---|---|
| VAL | 200 | LYS | 174 | 3.28 |
| PHE | 201 | ALA | 125 | 2.87 |
| PHE | 201 | VAL | 123 | 2.93 |

TABLE 15

Hydrogen bonds involving C-terminal residues of ROBO2 (copy2)

| Residue_1 | Residue_1 # | Residue_2 | Residue_2 # | Distance (Å) |
|---|---|---|---|---|
| PHE | 201 | ALA | 125 | 2.84 |
| PHE | 201 | VAL | 123 | 2.94 |
| GLU | 202 | LYS | 174 | 3.43 |
| ARG | 203 | ALA | 125 | 3.03 |
| ARG | 203 | GLU | 127 | 3.23 |
| ARG | 203 | GLU | 127 | 3.12 |

Example 6. Structural Analysis of ROBO2-Fc S17T/R73Y

Material Preparation, Crystallization, Data Collection, and Structure Determination:
Expression The human ROBO2 S17T/R73Y-His6 construct ("His6" disclosed as SEQ ID NO: 25) consists of human ROBO2 Ig1 domain with 2 point mutations (S17T and R73Y) followed by a C-terminal His×6 Tag (SEQ ID NO: 25). The human SLIT2 construct consists of the D2 domain of SLIT2 (271-479) followed by a C-terminal His6 Tag (SEQ ID NO: 25). These constructs were expressed in HEK293 cells separately and the conditioned media was harvested 120 hours post transfection.
Purification of Human ROBO2 S17T/R73Y-His6 ("His6" Disclosed as SEQ ID NO: 25) and SLIT2 D2 Domain Human ROBO2 S17T/R73Y-His6 ("His6" disclosed as SEQ ID NO: 25) was purified from conditioned media using Nickel Sepharose HP (GE Healthcare) and a gradient of imidazole. The peak fractions were combined and diluted to 20 mM NaCl, adjusted to pH 6.0 and loaded onto a HiTrap, Q Sepharose Fast Flow (Q FF) column placed in tandem with a HiTrap Strong sulfopropyl (SP). High Performance (HP) column. After extensive wash, Q FF column was removed and a gradient of NaCl was applied to SP HP column. Fractions were pooled based on extent of glycosylation and were dialyzed against TBS.

Human SLIT2 D2 domain was captured from conditioned media using Nickel Sepharose HP (GE Healthcare) and purified with gradient of imidazole. The peak fractions were pooled and further purified through Superdex 200 size exclusion chromatography under buffer containing 50 mM Tris HCl pH 7.5, 1000 mM NaCl. Fractions containing SLIT2 D2 were pooled and adjusted to 500 mM NaCl.
Complex Formation of Human ROBO2 S17T/R73Y-His and SLIT2 D2 Domain Due to unexpected interaction between SLIT2 and the resin of the gel filtration column, the complex of ROBO2 S17T/R73Y-His6 ("His6" disclosed as SEQ ID NO: 25) and SLIT2 could not be obtained through size exclusion chromatography. Instead, purified ROBO2 S17T/R73Y-His6 ("His6" disclosed as SEQ ID NO: 25) was mixed with SLIT2 D2 domain at 1:1 molar ratio and concentrated for crystallization attempts.
Crystallization Crystals of ROBO2 S17T/R73Y-His6 ("His6" disclosed as SEQ ID NO: 25) in complex with SLIT2 D2 domain were obtained in the following condition: 100 mM Sodium Citrate pH5.5, 15% PEG6000. It yielded crystals that diffracted to 1.78 Å.
Data Collection Crystals were transiently cryo-protected and synchrotron data collection was performed remotely at Advanced Photon Source (APS). Image frames were processed using software AutoPROC (Global Phasing Ltd). The data belongs to space group $P2_12_12_1$, with unit cells as follows: a=163.251 Å, b=41.896 Å, c=50.938 Å, α=β=γ=90°, with one copy of the complex per asymmetric unit.
Structure Determination and Refinement Molecular Replacement searches using homology model of ROBO1 Ig1 domain and SLIT2 D2 domain (PDB code: 2V9T) yielded convincing solutions of each component. Refinement was performed using software autoBUSTER (Global Phasing Ltd), and the final R/Rfree factors at 1.78 Å are 0.1848 and 0.2354, respectively, with RMSD of bond 0.010 Å, RMSD of angles 1.10°.
Structural Results and Analysis The crystal structure of ROBO2 S17T/R73Y-His6-SLIT2 ("His6" disclosed as SEQ ID NO: 25) aligns extensively with that of ROBO1-SLIT2 and the ROBO-SLIT interface is highly conserved between ROBO2 and ROBO1. Therefore, the publicly available ROBO1-SLIT2 structure can be used as a substitute for ROBO2-SLIT2 for structural comparison to probe the impacts of S17T and R73Y.

Figure 16:
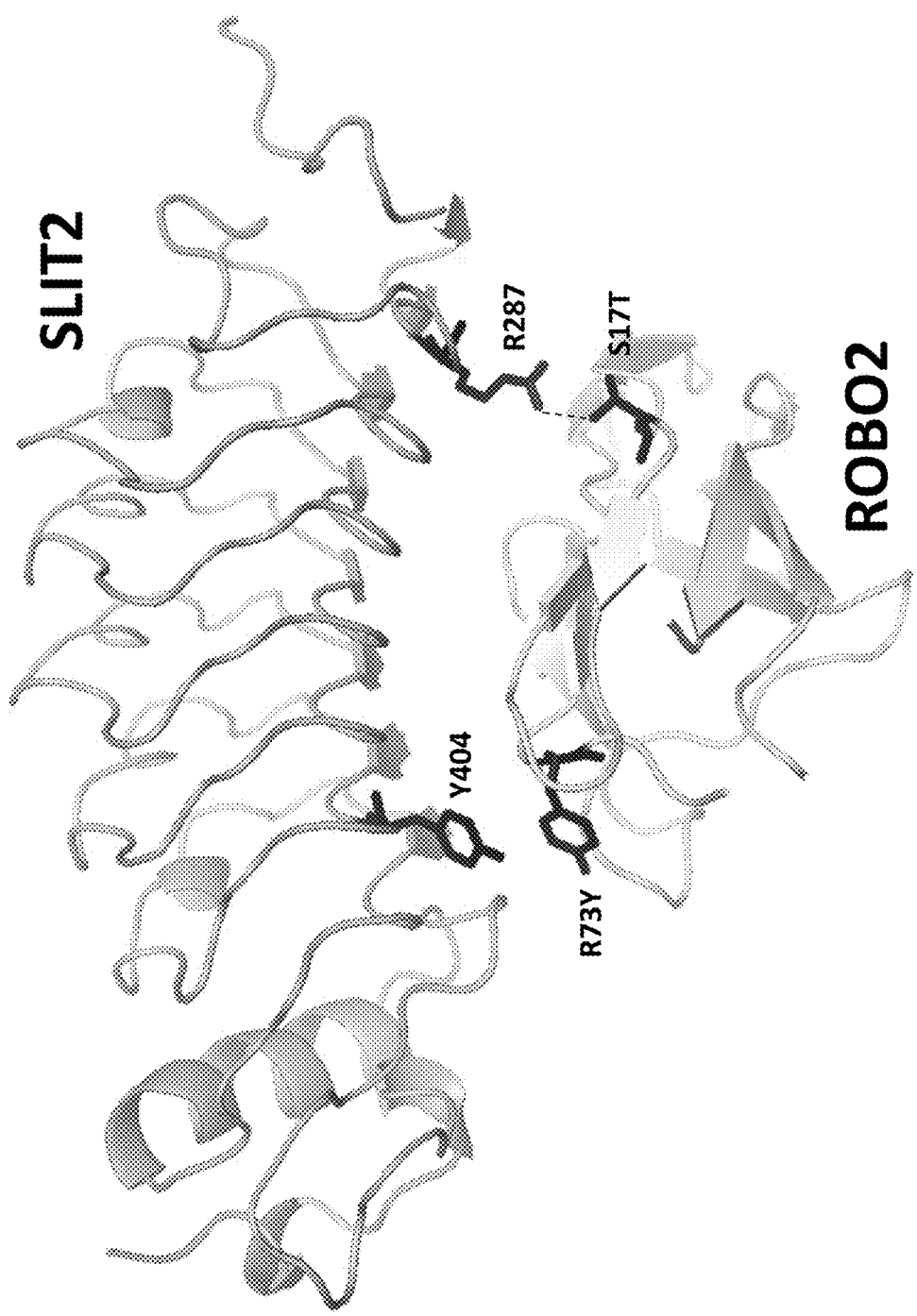
FIG. 16 shows the crystal structure of the first immunoglobulin-like domain (Ig1) of ROBO2 S17T/R73Y in complex with SLIT2.

Ser17 (S17) of ROBO2 interacts with Arg287 of SLIT2 via a hydrogen bond (FIG. 16). The hydrogen bond with Arginine is conserved regardless of the mutation; however, Thr17 provides additional van der Waals' contact with Arg287, and thus elicits slight energetic advantage over the wild-type Ser17.

R73Y of ROBO2 interacts with Tyr404 of SLIT2 (FIG. 16). The van der Waals' interactions caused by pi-pi stacking of two tyrosine residues are clearly more superior over those between a tyrosine and a flexible arginine side-chain. This is evident through the percentage of buried surface area (42% for Tyr73 vs. 22% for Arg73; Tables 16-19). The Arg to Tyr mutation in ROBO2 S17T/R73Y is likely to be the main contributor for the increase in affinity compared with wild type ROBO2 comprising S17 and R73.

In addition, S17T and R73Y are located at the opposite ends of the ROBO2-SLIT2 interface (FIG. 16). Without wishing to be bound by any particular theory, stabilizing interactions at these positions likely help ROBO2 to better 'stick' with SLIT2, and thus increases global binding affinity of the two proteins.

TABLE 16

Interaction table for the key mutations in ROBO2

| Residue_1 | Residue_1 # | Chain | Residue_2 | Residue_2 # | Chain | Distance (Å) |
|---|---|---|---|---|---|---|
| THR | 17 | ROBO2 | ARG | 287 | SLIT2 | 3.28 |
| TYR | 73 | ROBO2 | TYR | 404 | SLIT2 | 3.43 |

TABLE 17

Interaction table for the corresponding wild-type residues in ROBO1

| Residue_1 | Residue_1 # | Chain | Residue_2 | Residue_2 # | Chain | Distance (Å) |
|---|---|---|---|---|---|---|
| SER | 17 | ROBO1 | ARG | 287 | SLIT2 | 3.25 |
| ARG | 73 | ROBO1 | TYR | 404 | SLIT2 | 3.01 |

TABLE 18

Buried surface area analysis for the key mutations in ROBO2

| Residue | Residue # | Chain | Complex ASA | Free ASA | BSA | BSA % |
|---|---|---|---|---|---|---|
| THR | 17 | ROBO2 | 64.76 | 99.97 | 35.21 | 35.22 |
| TYR | 73 | ROBO2 | 44.17 | 75.85 | 31.68 | 41.77 |

TABLE 19

Buried surface area analysis for the corresponding wild-type residues in ROBO1

| Residue | Residue # | Chain | Complex ASA | Free ASA | BSA | BSA % |
|---|---|---|---|---|---|---|
| SER | 17 | ROBO1 | 53.39 | 79.32 | 25.93 | 32.69 |
| ARG | 73 | ROBO1 | 98.23 | 125.94 | 27.71 | 22 |

Example 7: Post-Translational Modifications of ROBO2-Fc 2.2

LC/MS—Peptide Mapping

Analysis of post-translational modifications of ROBO2-Fc 2.2 was accomplished by peptide mapping. Briefly, ROBO2-Fc 2.2 was reduced, alkylated and digested with the lysine specific protease, Lysyl Endopeptidase (Lys-C). The Lys-C proteolytic peptides were analyzed by reversed-phase high performance liquid chromatography (RP-HPLC) with UV detection at 214 nm.

All major and minor peaks in the peptide map for ROBO2-Fc 2.2 were identified by on-line electrospray ionization mass spectrometry (RP-HPLC/ESI MS or LC/MS). The observed masses for each peak were consistent with the expected Lys-C proteolytic peptides from ROBO2-Fc 2.2. These LC/MS-peptide mapping results demonstrate that ROBO2-Fc 2.2 contains the correct amino acid sequence, as predicted from the cDNA sequence. LC/MS analysis indicated the presence of N-linked oligosaccharides in peptide K6 (which was detected as K4K5K6), which contains a $N^{102}AS$ consensus sequence for N-linked glycosylation. The major oligosaccharide structures identified in the K4K5K6 glycopeptide include biantennary complex-type structures containing either two galactose residues with one terminal N-acetylneuraminic acid residue (G2F+1NeuAc) or two terminal N-acetylneuraminic acid residues (G2F+2NeuAc). A minor level K4K5K6 glycopeptide containing two terminal galactose residues (G2F) was observed. Other minor level species representing triantennary and tetraantennary complex-type structures with core-substituted fucose containing up to four terminal N-acetylneuraminic acid residues were observed.

LC/MS analysis also indicated the presence of N-linked oligosaccharides in peptide K19 (observed as K18K19), which contains the $N^{291}ST$ consensus sequence for N-linked glycosylation. The major oligosaccharide structures identified on K18K19 include asialo-biantennary complex-type structures containing zero (G0F) or 1 (G1F) terminal galactose residues. Minor level K18K19 with the asialo-biantennary complex-type structure containing two galactose residues (G2F) was observed. Minor and trace level glycopeptide K18K19 containing truncated N-glycans and complex N-glycans containing up to two terminal N-acetylneuraminic acid residues were detected.

TABLE 20

LC/MS - N-linked glycosylation

| Characteristics | Results |
|---|---|
| N-linked glycosylation | N-linked glycosylation site occupancy confirmed at $N^{291}ST$ in the K18K19 peptide (Major >40%, Minor 5-40%, Trace <5%): N-glycans detected (identities and relative abundances): Major: G0F, G1F Minor: G0, G2F Trace: aglycosylated, G0 minus GlcNAc (truncated), G0F minus GlcNAc (truncated), Man5 (high mannose), G1, G1F + 1NeuAc, G2F + 1NeuAc, and G2F + 2NeuAc N-linked glycosylation site occupancy confirmed at $N^{102}AT$ in the K4K5K6 and K5K6 peptides in the peptide map (Major >40%, Minor 5-40%, Trace <5%): N-glycans detected (identities and relative abundances): Major: G2F + 1NeuAc, G2F + 2NeuAc Minor: G2F, G3-TriF + 2NeuAc, G3-TriF + 3NeuAc, G4-TetraF + 3NeuAc, and G2F + 2NeuAc (K5K6 peptide) Trace: G0 minus GlcNAc (truncated), G1F + 1NeuAc, G4-TetraF + 2NeuAc, G4 TetraF + 4NeuAc, G2F + 1NeuAc (K5K6 peptide) |

Example 8: Safety Pharmacology Study

ROBO2-Fc 2.2 was administered once weekly by intravenous (IV) injection for 6 weeks (total of 6 doses) at a dose of 50 mg/kg/dose to telemetered male monkeys to evaluate cardiovascular (CV) endpoints. Statistically significant differences in heart rate (HR) and activity were observed. However, these differences were small in magnitude, sporadic in nature, and not sustained over time; therefore, they were not considered ROBO2-Fc 2.2 related. IV administration of ROBO2-Fc 2.2 at 50 mg/kg/dose once weekly for 6 weeks produced no ROBO2-Fc 2.2-related changes in blood pressure (BP), HR, or activity at any time throughout the study. The $C_{max}$ values were 1060, 1030, and 1070 µg/mL on Days 1, 22, and 36, respectively.

In a repeat-dose exploratory toxicity study (ETS) in telemetered male and female cynomolgus monkeys, the effects of once weekly IV administration of ROBO2-Fc 2.2 at 50 mg/kg/dose for 29 days (total of 5 doses) on electrocardiogram (ECG) and blood pressure (BP) parameters and activity were assessed. There were no ROBO2-Fc 2.2-related effects on CV measurements collected through Day 9. On Day 29, combined sex $C_{max}$ was 497 µg/mL.

ECG and HR measurements were incorporated into the Good Laboratory Practice (GLP)-compliant 3-month repeat-dose toxicity study in male and female cynomolgus monkeys at doses of 20, 100, or 300 mg/kg/dose IV, or 300 mg/kg/dose subcutaneous (SC). There were no ROBO2-Fc 2.2-related effects on ECG or HR in this study at a mean combined sex $C_{max}$ up to 9210 µg/mL. In addition, there were no ROBO2-Fc 2.2-related clinical observations that would be suggestive of any respiratory or central nervous system effects.

In addition, neurofunctional endpoints were assessed in the 3-month toxicity study in rats. There were no ROBO2-Fc 2.2-related effects on locomotor activity or the functional observational battery at doses up to 425 mg/kg/dose IV or at 425 mg/kg/dose SC (mean combined sex $C_{max}$ up to 7610 µg/mL).

Example 9: Pharmacokinetics and Product Metabolism in Animals

Methods of Analysis

I. Quantitation of ROBO2-Fc 2.2 in Rat and Monkey Serum

An electrochemiluminescent (ECL) assay was validated for the quantitation of ROBO2-Fc 2.2 in Wistar Han rat and cynomolgus monkey serum on the Meso Scale Discovery (MSD®) assay platform (15-1611, 15-1609). In these assays, samples containing ROBO2-Fc 2.2 were incubated onto streptavidin-coated MSD plates coated with biotinylated anti-ROBO2-Fc antibody capture reagent. The bound ROBO2-Fc 2.2 was detected with ruthenylated mouse anti-human IgG Fc antibody. Final detection was achieved by adding MSD Read Buffer to produce an ECL signal that was read using a MSD plate reader. The resulting ECL signal was directly proportional to the concentration of ROBO2-Fc 2.2. Sample concentrations were determined by interpolation from a standard curve that was fit using a 4PL logistic (autoestimate) model with a weighting factor of 1/y. The range of quantitation in 100% serum was 50 to 1280 ng/mL with a minimum required dilution factor (MRD) of 20×.

II. Detection of Anti ROBO2-Fc 2.2 Antibodies in Rat and Monkey Serum

An ECL assay was validated to detect the presence of anti-drug antibodies (ADA) in Wistar Han rat and cynomolgus monkey serum using the MSD® assay platform. In these assays, biotin and ruthenium-labeled ROBO2-Fc 2.2 were co-incubated with study samples, positive controls (anti-ROBO2-Fc 2.2 antibodies in Wistar Han or cynomolgus monkey serum), or negative controls (pooled normal Wistar Han or cynomolgus monkey serum). Antibodies to ROBO2-Fc 2.2 present in the samples must bind to both the biotin- and ruthenium-labeled versions of ROBO2-Fc 2.2 to be detected in these assays. Bound ADA was captured using streptavidin-coated MSD plates. Final detection was achieved using tripropylamine to produce an ECL signal that was measured using a MSD plate reader and reported in relative light units (RLU).

Study samples were tested for ADA using a tiered strategy. Samples were initially tested in a screening assay at a minimum required dilution of 1:50. Samples that generated an RLU below the assay cutoff point were reported as negative (<1.70, the log 10 of the minimum required dilution factor, 50). Samples that generated an RLU at or above the assay cutoff point were reanalyzed in a full dilution series to confirm the positive result and determine the antibody titer. The antibody titer was defined as the reciprocal dilution of the sample that would have generated an RLU equivalent to the assay cutoff point RLU and the log (to base 10) of that titer was reported.

Conclusions regarding the induction of ADA were made based on the comparison of samples collected prior to dosing on Day 1 and post-dose sample results. If the pre-dose sample tested negative for ADA and the corresponding post-dose sample tested positive, the animal was considered to be positive for the induction of an ADA response to ROBO2-Fc 2.2. If both the pre-dose and post-dose samples tested positive for ADA, the animal was considered to be positive for the induction of an ADA response only if the post-dose sample titer was additively at least 0.48 (log 3, the serial dilution factor) or higher than the titer of the pre-dose sample.

Results

I. Pharmacokinetics

A. Single-Dose Pharmacokinetics

The serum PK of ROBO2-Fc 2.2 were determined in Lewis rats (n=3) and cynomolgus monkeys (n=2) following a single IV dose at 10 mg/kg. ROBO2-Fc 2.2 exhibited a clearance (CL) of 1.5 mL/h/kg in rats, 0.89 mL/h/kg in monkey, and a steady state volume of distribution (Vss) of 0.19 L/kg in rats, 0.09 L/kg in monkeys, resulting in a terminal half-life (t½) of approximately 5 and 8 days in rat and monkey, respectively. Following 10 mg/kg SC administration of ROBO2-Fc 2.2 to rats, the estimated bioavailability was 56%.

B. Repeat-Dose Pharmacokinetics (Toxicokinetics; TK)

Rat Toxicokinetics

TK and ADA evaluations were conducted after IV administration of 25, 125, or 425 mg/kg/dose, and after SC administration of 425 mg/kg/dose, given once every 3 days to male and female Wistar Han rats (n=6/sex/dose group) as part of a 3-month GLP pivotal toxicity study with a 6-week recovery phase.

There were no quantifiable concentrations of ROBO2-Fc 2.2 in samples collected and analyzed prior to dosing on Day 1, or in samples collected and analyzed from the vehicle control group. Quantifiable concentrations of ROBO2-Fc 2.2 were observed until Day 88 (last samples collected) and until the last day of the recovery phase (Day 135) in the ROBO2-Fc 2.2-dosed group.

There were no apparent sex-related differences in systemic exposure (as assessed by maximum concentration

[$C_{max}$] and area under the concentration curve (AUC) from time 0 to 72 hours [$AUC_{72}$]) in any dose group. Mean systemic exposure increased with increasing dose in an approximately dose-proportional manner from Day 1 to Day 88. ROBO2-Fc 2.2 systemic bioavailability was 24.4% and 25.4% after SC dosing on Days 1 and Day 88, respectively. Accumulation ratios (AUC, Day 88/Day 1) were <2.0 for the IV and SC groups (Table 21).

The incidence of ADA induction to ROBO2-Fc 2.2 in the 25, 125 and 425 mg/kg IV groups was 0.0% (0/12 animals), 0.0% (0/12 animals), and 0.0% (0/12 animals), respectively, and was 41.7% in the 425 mg/kg SC group (5/12 animals). Serum ROBO2-Fc 2.2 concentrations were similar in the ADA-positive animals compared with ADA-negative animals. However, it should be noted that circulating levels of ROBO2-Fc 2.2 present in samples may have interfered with the detection of ADA.

Cynomolgus Monkey Toxicokinetics

TK and ADA evaluations were conducted after IV administration of 20, 100, or 300 mg/kg/dose, and after SC administration of 300 mg/kg/dose, given once every week to male and female cynomolgus monkeys (n=3 or 5/sex/dose group) as part of a 3-month GLP pivotal toxicity study with a 6-week recovery phase).

There were no quantifiable concentrations of ROBO2-Fc 2.2 in samples collected and analyzed prior to dosing on Day 1, or in samples collected and analyzed from the vehicle control group. Quantifiable concentrations of ROBO2-Fc 2.2 were observed until Day 78 (last samples collected) and until the last day of the recovery phase (Day 127 or 128) in the ROBO2-Fc 2.2-dosed group.

There were no apparent sex-related differences in systemic exposure (as assessed by $C_{max}$ and $AUC_{168}$) in any dose group. Mean systemic exposure increased with increasing dose in an approximately dose-proportional manner from Day 1 to Day 78. ROBO2-Fc 2.2 systemic bioavailability (300 mg/kg IV and SC dose) was 53.7% and 77.0% after SC dosing on Day 1 and Day 78, respectively. Accumulation ratios (AUC, Day 78/Day 1) were <2.0 for the IV groups, and the ratio was 2.1 for the SC group (Table 21).

The incidence of ADA induction to ROBO2-Fc 2.2 in the 20, 100 and 300 mg/kg IV groups was 0% (0/6 animals), 0% (0/6 animals), and 20% (2/10 animals), respectively, and was 33% in the 300 mg/kg SC group (2/6 animals). Serum ROBO2-Fc 2.2 concentrations were similar in the ADA-positive animals compared to ADA-negative animals. However, it should be noted that circulating levels of ROBO2-Fc 2.2 present in samples may have interfered with the detection of ADA.

II. Distribution

The Vss of ROBO2-Fc 2.2 in rats (0.19 L/kg) and monkeys (0.09 L/kg) was low following a single IV dose, consistent with limited distribution into extracellular fluids for an Fc containing protein.

III. Pharmacokinetics-Pharmacodynamics and Human PK Predictions

Based on PK/PD modeling (incorporating predicted human PK, measured ROBO2 and SLIT2 serum and kidney concentration data) an estimated weekly human SC dose of 2 mg/kg (150 mg) is predicted to maintain $C_{min}$ target coverage>90% in the kidney. The projected human efficacious concentration ($C_{eff}$) of ~11 µg/ml serum provides target coverage>90% in the kidney. The projected human steady state $C_{max}$ and AUCtau associated with a weekly human SC dose of 2 mg/kg (150 mg) are 18.2 µg/mL and 2610 µg·h/mL, respectively.

A prediction of human PK for ROBO2-Fc 2.2 has been made by scaling the cynomolgus monkey intravenous PK data based on allometric exponents. In human, ROBO2-Fc 2.2 is predicted to exhibit a clearance of 0.5 mL/h/kg and a steady state volume of distribution of 90 mL/kg providing a terminal half-life of approximately 14 days. The human SC bioavailability is predicted to be 60%.

In initial clinical studies, the exposure limit will be set to a $C_{max}$ of 2930 µg/mL and AUC of 74500 µg·h/mL determined as associated with exposure margins of 161× and 29× the projected human efficacious exposure, respectively at the projected human efficacious dose (150 mg SC once weekly). This exposure limit is based on the identified no observed adverse effect level (NOAEL) from the 3-month GLP toxicity study in rats.

While no ROBO2-Fc 2.2-related effect on serum cytokine levels was noted in the 3-month GLP toxicity studies in rats or cynomolgus monkeys ETS following administration of ROBO2-Fc 2.2 once weekly at 10 mg/kg/dose SC or 50 or 200 mg/kg/dose IV, respectively, increases of TNF-α and/or IL-6 were observed in 1 of 8 human donors and 1 of 12 monkeys in vitro. Although translatability of the in vitro finding is not well understood, measures such as slow administration of ROBO2-Fc 2.2 via IV infusion (with a small fraction of the total dose given in the first hour prior to administration of the remaining dose over the second hour) in single ascending dose phase of the study to allow pause/termination of dosing, close monitoring of vital signs, clinical symptoms and assessment of cytokine levels will be implemented.

TABLE 21

Mean Overall (Male + Female) Toxicokinetic Parameters ± Standard Deviation[a] in Rats and Monkeys

| Species/Study Number | Dose (mg/kg/dose)[b] | Route | Day | $C_{max}$ (µg/mL) | $T_{max}$ (hours) | $AUC_{72}$ or $AUC_{168}$ (µg · h/mL)[c] | $AUC_{72}$ or $AUC_{168}$/Dose ([µg · h/mL]/[mg/kg]) |
|---|---|---|---|---|---|---|---|
| Rat[d] | 25 | IV | 1 | 431 | 0.50 | 10700 | 428 |
| 16GR156 | | IV | 88 | 674 | 0.50 | 20900 | 836 |
| (3-month) | 125 | IV | 1 | 2370 | 0.50 | 47100 | 377 |
| | | IV | 88 | 2930 | 0.50 | 74500 | 596 |
| | 425 | IV | 1 | 9270 | 0.50 | 180000 | 424 |
| | | IV | 88 | 7610 | 0.50 | 199000 | 468 |
| | 425[e] | SC | 1 | 760 | 48 | 43900 | 103 |
| | | SC | 88 | 842 | 24 | 50500 | 119 |
| Cynomolgus Monkey[f] | 20 | IV | 1 | 403 ± 48.7 | 0.5 ± 0.0 | 17200 ± 2480 | 859 ± 124 |
| 16GR143 | | IV | 78 | 470 ± 56.5 | 0.5 ± 0.0 | 24300 ± 3640 | 1210 ± 182 |
| (3-month) | 100 | IV | 1 | 2470 ± 246 | 0.5 ± 0.0 | 95100 ± 15100 | 951 ± 151 |
| | | IV | 78 | 2350 ± 503 | 0.5 ± 0.0 | 113000 ± 29300 | 1130 ± 293 |

TABLE 21-continued

Mean Overall (Male + Female) Toxicokinetic Parameters ± Standard Deviation[a] in Rats and Monkeys

| Species/Study Number | Dose (mg/kg/dose)[b] | Route | Day | $C_{max}$ (µg/mL) | $T_{max}$ (hours) | $AUC_{72}$ or $AUC_{168}$ (µg · h/mL)[c] | $AUC_{72}$ or $AUC_{168}$/Dose ([µg · h/mL]/[mg/kg]) |
|---|---|---|---|---|---|---|---|
| | 300 | IV | 1 | 7160 ± 565 | 0.5 ± 0.0 | 287000 ± 15500 | 958 ± 51.5 |
| | | IV | 78 | 9210 ± 1080 | 0.5 ± 0.0 | 427000 ± 49800 | 1420 ± 166 |
| | 300[g] | SC | 1 | 1260 ± 250 | 32 ± 20 | 155000 ± 29000 | 515 ± 96.7 |
| | | SC | 78 | 2340 ± 480 | 36 ± 29 | 328000 ± 73200 | 1090 ± 244 |

$AUC_{168}$ = Area under the concentration-time curve from time zero to 168 hours; $AUC_{72}$ = Area under the concentration-time curve from time zero to 72 hours; $C_{max}$ = Maximum observed concentration, IV = Intravenous; SC = Subcutaneous; $T_{max}$ = Time to first occurence of $C_{max}$.
[a]Standard deviation not reported for 16GR156 because non-serial sampling was used.
[b]In study 16GR156, animals were dosed once every 3 days. In study 16GR143, animals were dosed once every week.
[c]$AUC_{72}$ was used in study 16GR156 and $AUC_{168}$ was used in study 16GR143.
[d]N = 6/sex/dose group (3/sex/time point).
[e]Bioavailability (F %) overall after SC dosing, based on $AUC_{72}$ was 24.4 on Day 1 and 25.4 on Day 88.
[f]N = 3 or 5/sex/dose group.
[g]Bioavailability (F %) overall after SC dosing, based on $AUC_{168}$ was 53.7 on Day 1 and 77.0 on Day 78.

Example 10: Toxicology

ROBO2-Fc 2.2 was administered to rats and cynomolgus monkeys by IV and SC injection, in exploratory (non-Good Laboratory Practice [GLP]-compliant) and pivotal (GLP-compliant) toxicity studies up to 3 months (13 weeks) in duration. The no observed adverse effect levels (NOAELs) following 3 months of dosing were:
(i) 125 mg/kg/dose IV ($C_{max}$ of 2930 µg/mL and $AUC_{72}$ of 74,500 µg·h/mL) and 425 mg/kg/dose SC ($C_{max}$ of 842 µg/mL and $AUC_{72}$ of 50,500 µg·h/mL) in rats, and
(ii) 300 mg/kg/dose IV ($C_{max}$ of 9210 µg/mL and $AUC_{168}$ of 427,000 µg·h/mL) and SC ($C_{max}$ of 2340 µg/mL and $AUC_{168}$ of 328,000 µg·h/mL) in monkeys.

I. Repeat-Dose Toxicity

Exploratory and pivotal repeat-dose toxicity studies were conducted with ROBO2-Fc 2.2 in rats and cynomolgus monkeys.

A. Rat Study (i) Exploratory Toxicity Study (ETS)

In an exploratory toxicity study (ETS) in male rats, ROBO2-Fc 2.2 was administered once every 3 days for 14 days (5 doses total) at 200 mg/kg/dose IV or 10, 50, or 200 mg/kg/dose SC, and was tolerated at all doses. There were no ROBO2-Fc 2.2-related clinical signs and no changes in body weight or food consumption parameters.

ROBO2-Fc 2.2-related effects included minimal to moderate SC perivascular inflammation in SC injection sites at ≥10 mg/kg/dose SC; higher absolute thymic weights (1.21×-1.44× control) and relative thymic weights (1.17×-1.39× control for organ-to-body weight and 1.22×-1.46× control for organ-to-brain weight) at ≥10 mg/kg/dose SC and IV that were not associated with a microscopic correlate; higher urine creatinine (1.70× and 1.83× control) and lower urine volume (0.52× and 0.55× control, respectively) at 200 mg/kg/dose SC and IV; higher mean urine specific gravity (1.011×-1.012× control) at 200 SC and 200 IV mg/kg/dose; and higher mean serum cholesterol (1.38× control) at 200 mg/kg/dose IV. The clinical chemistry and organ weight findings were not associated with any microscopic findings.

(ii) Repeat-Dose Toxicity Study

In a pivotal, repeat-dose rat toxicity study, ROBO2-Fc 2.2 was administered once every 3 days for 3 months (31 total doses) at 25, 125, or 425 mg/kg/dose IV or at 425 mg/kg/dose SC to rats, followed by a 6-week recovery phase (control and 425 mg/kg/dose IV). The neurofunctional effects of ROBO2-Fc 2.2 were also evaluated. ROBO2-Fc 2.2-related clinical signs included skin lesions (dorsal, thorax, cranial, or injection site) noted in 4/10 male rats at 425 mg/kg/dose SC during the dosing phase. These changes were not considered adverse as the incidence was only slightly higher compared with control group (2/15 males), and changes were noted only sporadically in the dosing phase and not present in animals administered ROBO2-Fc 2.2 at doses up to 425 mg/kg/dose IV. There were no ROBO2-Fc 2.2-related body weight, food consumption, ophthalmology, neurofunctional, or macroscopic findings.

In males, renal findings consisted of minimal glomerulopathy at ≥125 mg/kg/dose IV. In females, minimal glomerulopathy was also observed, only at 425 mg/kg/dose IV, and accompanied by minimal to mild tubular basophilia and hyaline tubular casts, as well as higher urinary protein (100 mg/dL). The morphologic findings of glomerulopathy, tubular basophilia, and hyaline tubular casts in females were adverse because that combination along with non-adverse higher urine protein indicated impaired renal function. In males, glomerulopathy was non-adverse, because the finding was much less extensive in distribution, occurred in the absence of tubular basophilia and hyaline casts, and was not associated with higher urine protein. Glomerulopathy was characterized by aggregates of granular eosinophilic material in glomeruli in renal cortices observed by light microscopy and podocyte foot process fusion surrounding glomerular capillary loops observed by transmission electron microscopy. At the end of the recovery phase, glomerulopathy completely recovered in males, and partially recovered and was non-adverse in females. There was also complete recovery of tubular basophilia, hyaline tubular casts, and urinary protein in females. Higher serum total protein (1.09×-1.18×) and serum albumin (1.10×-1.20×) were seen in the male group at 425 mg/kg/dose IV, and in the female groups at ≥25 mg/kg/dose IV and 425 mg/kg/dose SC. This was observed in the female group at 425 mg/kg/dose IV despite higher urinary protein.

Additional ROBO2-Fc 2.2-related microscopic findings occurred in animals administered 425 mg/kg/dose SC, and consisted of an increased incidence and/or severity (moderate) of hemorrhage and inflammation of the injection site compared with controls (minimal to mild) and an increased incidence of minimal lymphoid hyperplasia in the draining lymph node. Increased hemorrhage and inflammation at the SC injection site were non-adverse because they were only slightly more severe than the concurrent controls and were not associated with significant tissue injury beyond what would be expected as a result of the injection procedure. The increased incidence of minimal lymphoid hyperplasia in the draining lymph node was not adverse as it was morphologically similar to controls and likely represented a minor immune response to the ROBO2-Fc 2.2 and/or the dosing procedure. It is expected that these findings would recover once injections were no longer administered.

ROBO2-Fc 2.2-related higher liver weights noted at the conclusion of the dosing phase were non-adverse and consisted of higher mean absolute and relative to body and brain weights (1.11× to 1.17× compared with control) in female groups at ≥125 mg/kg/dose IV and 425 mg/kg/dose SC. These higher liver weights were non-adverse because of the absence of correlating macroscopic and microscopic findings and absence of alterations in hepatic enzymes indicative of tissue injury. There was complete recovery of higher liver weights.

Additional clinical pathology coagulation and clinical chemistry parameter changes were non-adverse and consisted of higher fibrinogen (1.21×-1.48×) in male and female groups at ≥125 mg/kg/dose IV, higher cholesterol (1.37×-2.52×) and triglycerides (1.58×-3.11×) in male groups at ≥125 mg/kg/dose IV and female groups at ≥25 mg/kg/dose IV and 425 mg/kg/dose SC, and higher globulin (1.16×) and higher calcium (1.09×) in the female group at 425 mg/kg/dose IV. There was complete recovery of fibrinogen, cholesterol, triglycerides, total protein, serum albumin, and globulin in male and female groups, but only partial recovery in calcium (1.04× control group at recovery) in the female group at 425 mg/kg/dose IV. These clinical pathology changes were non-adverse based on the small magnitude of the differences between the ROBO2-Fc 2.2-administered and control group means and the absence of correlating macroscopic and microscopic findings.

A summary of the toxicokinetics in rats following 3 months of administration ROBO2-Fc 2.2 can be found in Table 22. Following IV administration of ROBO2-Fc 2.2 at 25, 125, or 425 mg/kg/dose, or SC administration at 425 mg/kg/dose once every three days for 3 months (31 total doses) to rats, 125 mg/kg/dose IV and 425 mg/kg/dose SC were identified as the NOAELs.

B. Monkey Study (i) Exploratory Toxicity Study (ETS)

In an ETS in male and female cynomolgus monkeys, ROBO2-Fc 2.2 was administered once weekly for 29 days (5 total doses) at 50 or 200 mg/kg/dose IV or at 10 mg/kg/dose SC. Cardiovascular effects were evaluated in telemetry-implanted animals in the 50 mg/kg/dose IV group. Selected animals were necropsied on Day 30, the day following the last dose. Two monkeys from the 50 mg/kg/dose IV group were retained to Day 71 for assessment of tolerability and toxicokinetics. Administration of ROBO2-Fc 2.2 was tolerated at all doses. There were no ROBO2-Fc 2.2-related effects on survival, clinical signs, body weight, food consumption, cardiovascular measurements, in vivo cytokine assessment, hematology and coagulation parameters, and macroscopic and microscopic findings. ROBO2-Fc 2.2-related effects included minor increases in aspartate aminotransferase in both females at 50 mg/kg/dose IV (1.26×-1.51× baseline) and in the 200 mg/kg/dose IV male and female animals (1.59× and 1.55× baseline, respectively) and minor increases in alanine aminotransferase in the same females at 50 mg/kg/dose IV (1.29×-2.05× baseline) and 200 mg/kg/dose IV (1.29× baseline). These enzyme increases were not associated with ROBO2-Fc 2.2-related microscopic changes in the livers of these animals.

(ii) Repeat-Dose Toxicity Study

In a pivotal repeat-dose cynomolgus monkey toxicity study, ROBO2-Fc 2.2 was administered once weekly for 3 months (13 total doses) at 20, 100, or 300 mg/kg/dose IV or at 300 mg/kg/dose SC, followed by a 6-week recovery phase (control and 300 mg/kg/dose IV). There were no adverse ROBO2-Fc 2.2-related findings in any endpoints evaluated in this study. There were no ROBO2-Fc 2.2-related clinical signs, body weight, food consumption, electrocardiogram/heart rate, hematology, coagulation, urinalysis, ophthalmology, organ weight, or macroscopic findings. ROBO2-Fc 2.2-related clinical chemistry alterations included increased cholesterol (1.25×-1.61× baseline) at 300 mg/kg/dose IV or SC, increased triglycerides (1.58×-4.59× baseline) at ≥20 mg/kg/dose IV or 300 mg/kg/dose SC, and decreased globulin (0.83×-0.87× baseline) at ≥100 mg/kg/dose IV or 300 mg/kg/dose SC. All clinical chemistry alterations were non-adverse due to their small magnitude of change and absence of associated tissue changes. Clinical chemistry alterations fully recovered with the exception of increased triglycerides which persisted in the 300 mg/kg/dose IV males following the recovery phase (2.78×-6.79× baseline); quantifiable concentrations of ROBO2-Fc 2.2 were present until Days 128/127 of the recovery phase.

Increased cellularity of lymphoid follicles was observed in the draining (left axillary) and axillary (right axillary) lymph nodes of animals administered 300 mg/kg/dose SC. This finding was characterized by minimally to mildly increased size and number of lymphoid follicles with prominent germinal center formation and was consistent with a response against antigenic stimuli. This finding was non-adverse due to its minimal to mild severity. It is expected that this finding would recover once injections were no longer administered. In contrast, no ROBO2-Fc 2.2-related microscopic findings were present in animals administered ROBO2-Fc 2.2 at doses up to 300 mg/kg/dose IV. A summary of the toxicokinetics in cynomolgus monkeys following 3 months of administration of ROBO2-Fc 2.2 can be found in Table 22. Following administration of ROBO2-Fc 2.2 at 20, 100, or 300 mg/kg/dose IV, or at 300 mg/kg/dose SC once weekly for 3 months (13 total doses) to monkeys, 300 mg/kg/dose IV and 300 mg/kg/dose SC were identified as the NOAELs.

II. Local Tolerance

IV and SC injection sites were evaluated microscopically in the exploratory and pivotal rat and cynomolgus monkey repeat-dose toxicity studies. There were no ROBO2-Fc 2.2-related findings in IV injection sites of rats. ROBO2-Fc 2.2-related findings were only noted in the SC injections sites of rats. In the rat ETS, minimal to moderate subcutaneous perivascular inflammation at ≥10 mg/kg/dose SC was attributed to the physical trauma of injection and considered non-adverse. In the pivotal rat study, increased severity (moderate) of hemorrhage and considered non-adverse because they were only slightly more severe than the concurrent controls and were not associated with significant tissue injury beyond what would be expected as a result of the injection procedure. Also in the pivotal rat study, ROBO2-Fc 2.2-related skin lesions (dorsal, thorax, cranial, or injection site) were noted in males at 425 mg/kg/dose SC during the dosing phase. These changes were not considered adverse as the incidence was only slightly higher compared with control group, and were noted sporadically in the dosing phase.

There were no ROBO2-Fc 2.2-related findings in IV injection sites of cynomolgus monkeys. Hemorrhage and/or neutrophilic inflammation of various severities present in the IV injection sites in most animals, including controls, in the ETS at doses up to 200 mg/kg/dose IV were not considered to be ROBO2-Fc 2.2 related, and there were no ROBO2-Fc 2.2-related IV injection site findings in the pivotal cynomolgus monkey study at doses up to 300 mg/kg/dose IV. There were no ROBO2-Fc 2.2-related findings in SC injection sites of monkeys.

III. Cytokine Release Assays

In an in vitro cytokine release assay (CRA) using human whole blood samples, ROBO2-Fc 2.2 elicited tumor necrosis factor-alpha (TNF-α) and interleukin-6 (IL-6) production in whole blood samples from 1 of 8 human donors tested. No ROBO2-Fc 2.2-related interferon-gamma (IFN-γ) release was observed in human whole blood samples incubated with ROBO2-Fc 2.2.

In an in vitro CRA using cynomolgus monkey whole blood samples collected prior to the initiation of dosing, ROBO2-Fc 2.2 elicited IL-6 production in whole blood samples from 1 of 12 cynomolgus monkeys tested, with no ROBO2-Fc 2.2-related TNF-α or IFN-γ release observed.

Additionally, blood samples were collected from cynomolgus monkeys in the ETS following administration of ROBO2-Fc 2.2 once weekly at 10 mg/kg/dose SC or 50 or 200 mg/kg/dose IV in order to characterize changes in cytokine concentrations. There were no ROBO2-Fc 2.2-related changes in serum concentrations of TNF-α, IL-6, or IFN-γ.

IV. C1q and FcγR Binding Assays

ROBO2-Fc 2.2 was evaluated in vitro in a complement protein 1q (C1q) binding ELISA to test its potential to elicit complement-dependent cytotoxicity (CDC), and in a fragment crystallizable gamma receptor (FcγR) binding assay to test its potential for antibody-dependent cell-mediated cytotoxicity (ADCC) activity. ROBO2-Fc 2.2 did not bind to C1q up to the concentrations tested and therefore is considered to have a low potential for inducing CDC. ROBO2-Fc 2.2 binding to all FcγRs tested was similar or lower compared with binding seen with the assay control antibody, and was lower compared with data from the positive control antibody. These data suggest that ROBO2-Fc 2.2 has low potential to elicit ADCC activity.

V. Relationship of Findings to Pharmacokinetics

ROBO2-Fc 2.2 exposure (as assessed by $C_{max}$ and AUC) increased with increasing dose in an approximately dose-proportional manner after repeat IV and SC dosing to rats and cynomolgus monkeys over the dose ranges tested. There were no apparent sex-related differences in exposure observed. The threshold concentrations of ROBO2-Fc 2.2 associated with key responses and exposure margins calculated against these key responses can be found in Table 22.

TABLE 22

Concentrations of ROBO2-Fc 2.2 Associated with Key Responses

| Key Response(s) | Dose (mg/kg/day) | $C_{max}^{a}$ (μg/mL) | $AUC_{last}^{a}$ (μg · h/mL) | $C_{max}$ Exposure Margin[b] | $AUC_{last}$ Exposure Margin[b] |
|---|---|---|---|---|---|
| Repeat-Dose Toxicity Studies 14-Day IV/SC ETS in Male Rats (13MA059; 5/group) | | | | | |
| Target organs: SC injection site: perivascular inflammation Lymphoid tissues: ↑ thymic weights | 10 SC | 33.7 | 2040 | 1.9 | <1 |
| Same as above | 50 SC | 73.7 | 3820 | 4.1 | 1.5 |
| Same as above, plus Kidney: ↑ urine creatinine, SG, ↓ urine volume | 200 SC | 245 | 12500 | 13 | 4.8 |
| Same as above, plus Liver: ↑ CHOL | 200 IV | 6550 | 68600 | 360 | 26 |
| 3-Month IV/SC Toxicity Study in Rats With a 6-Week Recovery (16GR156; 10 or 15/sex/group) | | | | | |
| Target organs: Liver: ↑: CHOL (F), TRIG (F) Other findings: ↑ ALB (F) | 25 IV | 674 | 20900 | 37 | 8.0 |
| Kidney: glomerulopathy (M) Liver: ↑: CHOL (M), TRIG (M), weights (F) Other findings: ↑ FIB, ↑ TP (F) | 125 IV (NOAEL) | 2930 | 74500 | 161 | 29 |
| Same as above, plus Kidney: glomerulopathy (F), tubular basophilia (F), hyaline casts (F), ↑ urinary protein (F) Liver: ↑: CHOL (M), TRIG (M) Other findings: ↑: GLOB (F), CA (F), FIB, TP (M), ALB (M) Recovery: partial recovery of glomerulopathy and CA (F), complete for all other findings | 425 IV | 7610 | 199000 | 418 | 76 |
| SC injection site: inflammation and hemorrhage Liver: ↑: CHOL (F), TRIG (F), weights (F) Lymphoid tissues: ↑ lymphoid hyperplasia in draining lymph nodes Other findings: ↑ ALB (F), skin lesions (M) | 425 SC (NOAEL) | 842 | 50500 | 46 | 19 |

TABLE 22-continued

Concentrations of ROBO2-Fc 2.2 Associated with Key Responses

| Key Response(s) | Dose (mg/kg/day) | $C_{max}{}^a$ (µg/mL) | $AUC_{last}{}^a$ (µg · h/mL) | $C_{max}$ Exposure Margin[b] | $AUC_{last}$ Exposure Margin[b] |
|---|---|---|---|---|---|
| 29-Day IV ETS in Telemetered Monkeys With a SC Arm (14MA014; 1 or 2/sex/group) | | | | | |
| Target organs: Liver: ↑: AST (F), ALT (F) | 50 IV | 1050 | 19100 | 58 | 7.3 |
| Same as above, plus Liver: ↑ AST (M) | 200 IV | 6420 | 96200 | 353 | 37 |
| 3-Month IV/SC Toxicity Study in Monkeys With a 6-Week Recovery (16GR143; 3 or 5/sex/group) | | | | | |
| Target organs: Liver: ↑ TRIG | 20 IV | 470 | 24300 | 26 | 9.3 |
| Same as above, plus Liver: ↓ GLOB | 100 IV | 2350 | 113000 | 129 | 43 |
| Same as above, plus Liver: ↑ CHOL Recovery: ↑ TRIG: complete for GLOB and CHOL | 300 IV (NOAEL) | 9210 | 427000 | 506 | 164 |
| Lymphoid tissues: ↑ cellularity of lymphoid follicles Liver: ↑: TRIG, CHOL; ↑ GLOB | 300 SC (NOAEL) | 2340 | 328000 | 129 | 126 |

ALB = Albumin; ALT = Alanine aminotransferase; AST = Aspartate aminotransferase; AUC = Area under the concentration-time curve; CHOL = Cholesterol; $C_{max}$ = Maximum (mean) plasma concentration; ETS = Exploratory Toxicity Study; F = Female; FIB = Fibrinogen; GLOB = Globulin; IV = Intravenous; M = Male; NOAEL = No observed adverse effect level; SC = Subcutaneous; SG = Specific gravity; TP = Total protein; TRIG = Triglyceride.
[a]AUC and $C_{max}$ values indicate mean serum concentrations. Reported values were obtained near termination.
[b]Exposure margins were calculated by dividing $C_{max}$ and $AUC_{last}$ values in animal toxicity studies by the projected human $C_{max}$ of 18.2 µg/mL and $AUC_{tau}$ = 2610 µg · h/mL at the projected efficacious human dose of 2 mg/kg [150 mg] SC weekly.

In sum, these data suggest that ROBO2-Fc 2.2 is a potential human therapeutic for various diseases, disorders and conditions.

The invention thus has been disclosed broadly and illustrated in reference to representative embodiments described above. Those skilled in the art will recognize that various modifications can be made to the present invention without departing from the spirit and scope thereof. All publications, patent applications, and issued patents, are herein incorporated by reference to the same extent as if each individual publication, patent application or issued patent were specifically and individually indicated to be incorporated by reference in its entirety. Definitions that are contained in text incorporated by reference are excluded to the extent that they contradict definitions in this disclosure.

It is appreciated that certain features of the invention, which are, for clarity, described in the context of separate embodiments, may also be provided in combination in a single embodiment. Conversely, various features of the invention which are, for brevity, described in the context of a single embodiment, may also be provided separately or in any suitable sub-combination.

It is specifically contemplated that any limitation discussed with respect to one embodiment of the invention may apply to any other embodiment of the invention. Furthermore, any composition of the invention may be used in any method of the invention, and any method of the invention may be used to produce or to utilize any composition of the invention. In particular, any aspect of the invention described in the claims, alone or in combination with one or more additional claims and/or aspects of the description, is to be understood as being combinable with other aspects of the invention set out elsewhere in the claims and/or description and/or sequence listings and/or drawings.

In so far as specific examples found herein do not fall within the scope of an invention, said specific example may be explicitly disclaimed.

The use of the term "or" in the claims is used to mean "and/or" unless explicitly indicated to refer to alternatives only or the alternatives are mutually exclusive, although the disclosure supports a definition that refers to only alternatives and "and/or." As used herein the specification, "a" or "an" may mean one or more, unless clearly indicated otherwise. As used herein in the claim(s), when used in conjunction with the word "comprising", the words "a" or "an" may mean one or more than one. As used herein "another" may mean at least a second or more. Unless otherwise defined herein, scientific and technical terms used in connection with the present invention shall have the meanings that are commonly understood by those of ordinary skill in the art. Further, unless otherwise required by context, singular terms shall include pluralities and plural terms shall include the singular. The words "comprises/comprising" and the words "having/including" when used herein with reference to the present invention are used to specify the presence of stated features, integers, steps or components but does not preclude the presence or addition of one or more other features, integers, steps, components or groups thereof.

Although the disclosed teachings have been described with reference to various applications, methods, and compositions, it will be appreciated that various changes and modifications can be made without departing from the teachings herein and the claimed invention below. The examples are provided to better illustrate the disclosed teachings and are not intended to limit the scope of the teachings presented herein. While the present teachings have been described in terms of these exemplary embodiments, numerous variations and modifications of these exemplary embodiments are possible without undue experimentation. All such variations and modifications are within the scope of the current teachings.

Where aspects or embodiments of the invention are described in terms of a Markush group or other grouping of alternatives, the present invention encompasses not only the entire group listed as a whole, but each member of the group individually and all possible subgroups of the main group, but also the main group absent one or more of the group members. The present invention also envisages the explicit exclusion of one or more of any of the group members in the claimed invention.

All references cited herein, including patents, patent applications, papers, text books, and the like, and the references cited therein, to the extent that they are not already, are hereby incorporated by reference in their entirety. In the event that one or more of the incorporated literature and similar materials differs from or contradicts this application, including but not limited to defined terms, term usage, described techniques, or the like, this application controls.

The description and examples detail certain specific embodiments of the invention and describes the best mode contemplated by the inventors. It will be appreciated, however, that no matter how detailed the foregoing may appear in text, the invention may be practiced in many ways and the invention should be construed in accordance with the appended claims and any equivalents thereof.

TABLE 23

| SEQ | DESCRIPTION | SEQUENCE |
|---|---|---|
| 1 | ROBO2-Fc 2.2 | SRLRQEDFPPRIVEHPSDVIVSKGEPTTLNCKAEGRPTPTIEWYK DGERVETDKDDPRSHRMLLPSGSLFFLRIVHGRRSKPDEGSYVC VARNYLGEAVSRNASLEVALLRDDFRQNPTDVVVAAGEPAILEC QPPRGHPEPTIYWKKDKVRIDDKEERISIRGGKLMISNTRKSDAG MYTCVGTNMVGERDSDPAELTVFERGGSGGSEPKSSDKTHTCP PCPAPEAAGAPSVFLFPPKPKDTLMISRTPEVTCVVVDVSHEDPE VKFNWYVDGVEVHNAKTKPREEQYNSTYRVVSVLTVLHQDWLN GKEYKCKVSNKALPAPIEKTISKAKGQPREPQVYTLPPSREEMTK NQVSLTCLVKGFYPSDIAVEWESNGQPENNYKTTPPVLDSDGSF FLYSKLTVDKSRWQQGNVFSCSVMHEALHNHYTQKSLSLSPG |
| 2 | ROBO2-Fc 2.1 | PRIVEHPSDVIVSKGEPTTLNCKAEGRPTPTIEWYKDGERVETDK DDPRSHRMLLPSGSLFFLRIVHGRRSKPDEGSYVCVARNYLGEA VSRNASLEVALLRDDFRQNPTDVVVAAGEPAILECQPPRGHPEP TIYWKKDKVRIDDKEERISIRGGKLMISNTRKSDAGMYTCVGTNM VGERDSDPAELTVFERGGSGGSEPKSSDKTHTCPPCPAPEAAG APSVFLFPPKPKDTLMISRTPEVTCVVVDVSHEDPEVKFNWYVD GVEVHNAKTKPREEQYNSTYRVVSVLTVLHQDWLNGKEYKCKV SNKALPAPIEKTISKAKGQPREPQVYTLPPSREEMTKNQVSLTCL VKGFYPSDIAVEWESNGQPENNYKTTPPVLDSDGSFFLYSKLTV DKSRWQQGNVFSCSVMHEALHNHYTQKSLSLSPGK |
| 3 | ROBO2-Fc 2.0 | PRIVEHPSDVIVSKGEPTTLNCKAEGRPTPTIEWYKDGERVETDK DDPRSHRMLLPSGSLFFLRIVHGRRSKPDEGSYVCVARNYLGEA VSRNASLEVALLRDDFRQNPTDVVVAAGEPAILECQPPRGHPEP TIYWKKDKVRIDDKEERISIRGGKLMISNTRKSDAGMYTCVGTNM VGERDSDPAELTGGSGGSEPKSSDKTHTCPPCPAPEAAGAPSV FLFPPKPKDTLMISRTPEVTCVVVDVSHEDPEVKFNWYVDGVEV HNAKTKPREEQYNSTYRVVSVLTVLHQDWLNGKEYKCKVSNKA LPAPIEKTISKAKGQPREPQVYTLPPSREEMTKNQVSLTCLVKGF YPSDIAVEWESNGQPENNYKTTPPVLDSDGSFFLYSKLTVDKSR WQQGNVFSCSVMHEALHNHYTQKSLSLSPGK |
| 4 | ROBO2-Fc 1.1 | PRIVEHPSDVIVSKGEPTTLNCKAEGRPTPTIEWYKDGERVETDK DDPRSHRMLLPSGSLFFLRIVHGRRSKPDEGSYVCVARNYLGEA VSRNASLEVALLRGGSGGSEPKSSDKTHTCPPCPAPEAAGAPS VFLFPPKPKDTLMISRTPEVTCVVVDVSHEDPEVKFNWYVDGVE VHNAKTKPREEQYNSTYRVVSVLTVLHQDWLNGKEYKCKVSNK ALPAPIEKTISKAKGQPREPQVYTLPPSREEMTKNQVSLTCLVKG FYPSDIAVEWESNGQPENNYKTTPPVLDSDGSFFLYSKLTVDKS RWQQGNVFSCSVMHEALHNHYTQKSLSLSPGK |
| 5 | ROBO2-Fc 1.0 | PRIVEHPSDVIVSKGEPTTLNCKAEGRPTPTIEWYKDGERVETDK DDPRSHRMLLPSGSLFFLRIVHGRRSKPDEGSYVCVARNYLGEA VSRNASLEGGSGGSEPKSSDKTHTCPPCPAPEAAGAPSVFLFP PKPKDTLMISRTPEVTCVVVDVSHEDPEVKFNWYVDGVEVHNAK TKPREEQYNSTYRVVSVLTVLHQDWLNGKEYKCKVSNKALPAPI EKTISKAKGQPREPQVYTLPPSREEMTKNQVSLTCLVKGFYPSDI AVEWESNGQPENNYKTTPPVLDSDGSFFLYSKLTVDKSRWQQG NVFSCSVMHEALHNHYTQKSLSLSPGK |
| 6 | ROBO2-Fc 3.0 | PRIVEHPSDVIVSKGEPTTLNCKAEGRPTPTIEWYKDGERVETDK DDPRSHRMLLPSGSLFFLRIVHGRRSKPDEGSYVCVARNYLGEA VSRNASLEVALLRDDFRQNPTDVVVAAGEPAILECQPPRGHPEP TIYWKKDKVRIDDKEERISIRGGKLMISNTRKSDAGMYTCVGTNM VGERDSDPAELTVFERPTFLRRPINQVVLEEEAVEFRCQVQGDP QPTVRWKKDDADLPRGRYDIKDDYTLRIKKTMSTDEGTYMCIAE NRVGKMEASATLTGGSGGSEPKSSDKTHTCPPCPAPEAAGAPS VFLFPPKPKDTLMISRTPEVTCVVVDVSHEDPEVKFNWYVDGVE VHNAKTKPREEQYNSTYRVVSVLTVLHQDWLNGKEYKCKVSNK ALPAPIEKTISKAKGQPREPQVYTLPPSREEMTKNQVSLTCLVKG FYPSDIAVEWESNGQPENNYKTTPPVLDSDGSFFLYSKLTVDKS RWQQGNVFSCSVMHEALHNHYTQKSLSLSPGK |

TABLE 23-continued

| SEQ | DESCRIPTION | SEQUENCE |
|---|---|---|
| 7 | ROBO2-Fc 4.0 | PRIVEHPSDVIVSKGEPTTLNCKAEGRPTPTIEWYKDGERVETDK DDPRSHRMLLPSGSLFFLRIVHGRRSKPDEGSYVCVARNYLGEA VSRNASLEVALLRDDFRQNPTDVVVAAGEPAILECQPPRGHPEP TIYWKKDKVRIDDKEERISIRGGKLMISNTRKSDAGMYTCVGTNM VGERDSDPAELTVFERPTFLRRPINQVVLEEEAVEFRCQVQGDP QPTVRWKKDDADLPRGRYDIKDDYTLRIKKTMSTDEGTYMCIAE NRVGKMEASATLTVRAPPQFVVRPRDQIVAQGRTVTFPCETKGN PQPAVFWQKEGSQNLLFPNQPQQPNSRCSVSPTGDLTITNIQRS DAGYYICQALTVAGSILAKAQLEVTGGSGGSEPKSSDKTHTCPP CPAPEAAGAPSVFLFPPKPKDTLMISRTPEVTCVVVDVSHEDPEV KFNWYVDGVEVHNAKTKPREEQYNSTYRVVSVLTVLHQDWLNG KEYKCKVSNKALPAPIEKTISKAKGQPREPQVYTLPPSREEMTKN QVSLTCLVKGFYPSDIAVEWESNGQPENNYKTTPPVLDSDGSFF LYSKLTVDKSRWQQGNVFSCSVMHEALHNHYTQKSLSLSPGK |
| 8 | ROBO2 pre-Ig1 sequence | SRLRQEDFP |
| 9 | ROBO2 Ig1 | PRIVEHPSDVIVSKGEPTTLNCKAEGRPTPTIEWYKDGERVETDK DDPRSHRMLLPSGSLFFLRIVHGRRSKPDEGSYVCVARNYLGEA VSRNASLE |
| 10 | ROBO2 Ig1-2 linker | VALLR |
| 11 | ROBO2 Ig2 | DDFRQNPTDVVVAAGEPAILECQPPRGHPEPTIYWKKDKVRIDD KEERISIRGGKLMISNTRKSDAGMYTCVGTNMVGERDSDPAELT |
| 12 | ROBO2 Ig2-3 linker | VFER |
| 13 | ROBO2 Ig3 | PTFLRRPINQVVLEEEAVEFRCQVQGDPQPTVRWKKDDADLPR GRYDIKDDYTLRIKKTMSTDEGTYMCIAENRVGKMEASATLT |
| 14 | ROBO2 Ig4 | VRAPPQFVVRPRDQIVAQGRTVTFPCETKGNPQPAVFWQKEGS QNLLFPNQPQQPNSRCSVSPTGDLTITNIQRSDAGYYICQALTVA GSILAKAQLEVT |
| 15 | GS Linker | GGSGGS |
| 16 | IgG1 Fc 3mut | EPKSSDKTHTCPPCPAPEAAGAPSVFLFPPKPKDTLMISRTPEVT CVVVDVSHEDPEVKFNWYVDGVEVHNAKTKPREEQYNSTYRVV SVLTVLHQDWLNGKEYKCKVSNKALPAPIEKTISKAKGQPREPQ VYTLPPSREEMTKNQVSLTCLVKGFYPSDIAVEWESNGQPENNY KTTPPVLDSDGSFFLYSKLTVDKSRWQQGNVFSCSVMHEALHN HYTQKSLSLSPGK |
| 17 | ROBO2 Leader | MSLLMFTQLLLCGFLYVRVDG |
| 18 | Ig Leader | MGWSCIIFLVATAGAHS |
| 19 | ROBO2-Fc S17T/R73Y | SRLRQEDFPPRIVEHPTDVIVSKGEPTTLNCKAEGRPTPTIEWYK DGERVETDKDDPRSHRMLLPSGSLFFLYIVHGRRSKPDEGSYVC VARNYLGEAVSRNASLEVALLRDDFRQNPTDVVVAAGEPAILEC QPPRGHPEPTIYWKKDKVRIDDKEERISIRGGKLMISNTRKSDAG MYTCVGTNMVGERDSDPAELTVFERGGSGGSEPKSSDKTHTCP PCPAPEAAGAPSVFLFPPKPKDTLMISRTPEVTCVVVDVSHEDPE VKFNWYVDGVEVHNAKTKPREEQYNSTYRVVSVLTVLHQDWLN GKEYKCKVSNKALPAPIEKTISKAKGQPREPQVYTLPPSREEMTK VNQVSLTCLVKGFYPSDIAVEWESNGQPENNYKTTPPVLDSDGSF FLYSKLTVDKSRWQQGNVFSCSVMHEALHNHYTQKSLSLSPGK |
| 20 | ROBO2 Ig1 S17T R73Y | PRIVEHPTDVIVSKGEPTTLNCKAEGRPTPTIEWYKDGERVETDK DDPRSHRMLLPSGSLFFLYIVHGRRSKPDEGSYVCVARNYLGEA VSRNASLE |
| 21 | ROBO2-Fc 2.2 | TCGCGTCTTCGCCAGGAGGACTTTCCCCCGCGGATTGTGGAG CATCCTTCCGATGTCATCGTCTCTAAGGGCGAGCCCACGACT CTGAACTGCAAGGCGGAGGGCCGGCCAACGCCCACCATTGA GTGGTACAAAGATGGGGAGCGAGTGGAGACTGACAAGGACG ATCCCCGGTCCCACAGGATGCTTCTGCCCAGCGGATCCTTAT TCTTCTTGCGCATCGTGCACGGGCGCAGGAGTAAACCTGATG AAGGAAGCTACGTTTGTGTTGCGAGGAACTATCTTGGTGAAG CAGTGAGTCGAAATGCGTCTCTGGAAGTGGCATTGTTACGAG ATGACTTCCGACAAAACCCCACAGATGTTGTAGTGGCAGCTG |

TABLE 23-continued

SEQUENCES

| SEQ | DESCRIPTION | SEQUENCE |
|---|---|---|
| | | GAGAGCCTGCAATCCTGGAGTGCCAGCCTCCCCGGGGACAC<br>CCAGAACCCACCATCTACTGGAAAAAAGACAAAGTTCGAATTG<br>ATGACAAGGAAGAAAGAATAAGTATCCGTGGTGGAAAACTGAT<br>GATCTCCAATACCAGGAAAAGTGATGCAGGGATGTATACTTGT<br>GTTGGTACCAATATGGTGGGAGAAAGGGACAGTGACCCAGCA<br>GAGCTGACTGTCTTTGAACGAGGCGGCAGCGGCGGCAGCGA<br>GCCCAAATCTTCTGACAAAACTCACACATGCCCACCGTGCCC<br>AGCACCTGAAGCTGCAGGGGCACCGTCAGTCTTCCTCTTCCC<br>CCCAAAACCCAAGGACACCCTCATGATCTCCCGGACCCCTGA<br>GGTCACATGCGTGGTGGTGGACGTGAGCCACGAAGACCCTG<br>AGGTCAAGTTCAACTGGTACGTGGACGGCGTGGAGGTGCATA<br>ATGCCAAGACAAAGCCGCGGGAGGAGCAGTACAACAGCACG<br>TACCGTGTGGTCAGCGTCCTCACCGTCCTGCACCAGGACTGG<br>CTGAATGGCAAGGAGTACAAGTGCAAGGTCTCCAACAAAGCC<br>CTCCCAGCCCCCATCGAGAAAACCATCTCCAAAGCCAAAGGG<br>CAGCCCCGAGAACCACAGGTGTACACCCTGCCCCCATCCCG<br>GGAGGAGATGACCAAGAACCAGGTCAGCCTGACCTGCCTGG<br>TCAAAGGCTTCTATCCCAGCGACATCGCCGTGGAGTGGGAGA<br>GCAATGGGCAGCCGGAGAACAACTACAAGACCACGCCTCCC<br>GTGCTGGACTCCGACGGCTCCTTCTTCCTCTATAGCAAGCTC<br>ACCGTGGACAAGAGCAGGTGGCAGCAGGGGAACGTCTTCTC<br>ATGCTCCGTGATGCATGAGGCTCTGCACAACCACTACACGCA<br>GAAGAGCCTCTCCCTGTCCCCCGGA |
| 22 | Peptidyl linker | [Gly-Gly-Ser]$_n$ n = 1, 2, 3, 4, 5, or 6 |
| 23 | Peptidyl Linker | [Gly-Gly-Gly-Gly-Ser]$_n$, n = 1, 2, 3, 4, 5, or 6 |
| 24 | Human ROBO2<br>(ROBO2 Leader<br>sequence<br>underlined) | <u>MSLLMFTQLLLCGFLYVRVDG</u><br>SRLRQEDFPPRIVEHPSDVIVSKGEPTTLNCKAEGRPTPTIEWYK<br>DGERVETDKDDPRSHRMLLPSGSLFFLRIVHGRRSKPDEGSYVC<br>VARNYLGEAVSRNASLEVALLRDDFRQNPTDVVVAAGEPAILEC<br>QPPRGHPEPTIYWKKDKVRIDDKEERISIRGGKLMISNTRKSDAG<br>MYTCVGTNMVGERDSDPAELTVFERPTFLRRPINQVVLEEEAVE<br>FRCQVQGDPQPTVRWKKDDADLPRGRYDIKDDYTLRIKKTMST<br>DEGTYMCIAENRVGKMEASATLTVRAPPQFVVRPRDQIVAQGRT<br>VTFPCETKGNPQPAVFWQKEGSQNLLFPNQPQQPNSRCSVSPT<br>GDLTITNIQRSDAGYYICQALTVAGSILAKAQLEVTDVLTDRPPPII<br>LQGPANQTLAVDGTALLKCKATGDPLPVISWLKEGFTFPGRDPR<br>ATIQEQGTLQIKNLRISDTGTYTCVATSSSGETSWSAVLDVTESG<br>ATISKNYDLSDLPGPPSKPQVTDVTKNSVTLSWQPGTPGTLPAS<br>AYIIEAFSQSVSNSWQTVANHVKTTLYTVRGLRPNTIYLFMVRAIN<br>PQGLSDPSPMSDPVRTQDISPPAQGVDHRQVQKELGDVLVRLH<br>NPVVLTPTTVQVTWTVDRQPQFIQGYRVMYRQTSGLQATSSWQ<br>NLDAKVPTERSAVLVNLKKGVTYEIKVRPYFNEFQGMDSESKTV<br>RTTEEAPSAPPQSVTVLTVGSYNSTSISVSWDPPPPDHQNGIIQE<br>YKIWCLGNETRFHINKTVDAAIRSVIIGGLFPGIQYRVEVAASTSA<br>GVGVKSEPQPIIIGRRNEVVITENNNSITEQITDVVKQPAFIAGIGG<br>ACWVILMGFSIWLYWRRKKRKGLSNYAVTFQRGDGGLMSNGSR<br>PGLLNAGDPSYPWLADSWPATSLPVNNSNSGPNEIGNFGRGDV<br>LPPVPGQGDKTATMLSDGAIYSSIDFTTKTSYNSSSQITQATPYA<br>TTQILHSNSIHELAVDLPDPQWKSSIQQKTDLMGFGYSLPDQNK<br>GNNGGKGGKKKKNKNSSKPQKNNGSTWANVPLPPPPVQPLPG<br>TELEHYAVEQQENGYDSDSWCPPLPVQTYLHQGLEDELEEDDD<br>RVPTPPVRGVASSPAISFGQQSTATLTPSPREEMQPMLQAHLDE<br>LTRAYQFDIAKQTWHIQSNNQPPQPPVPPLGYVSGALISDLETDV<br>ADDDADDEEEALEIPRPLRALDQTPGSSMDNLDSSVTGKAFTSS<br>QRPRPTSPFSTDSNTSAALSQSQRPRPTKKHKGGRMDQQPALP<br>HRREGMTDEEALVPYSKPSFPSPGGHSSSGTASSKGSTGPRKT<br>EVLRAGHQRNASDLLDIGYMGSNSQGQFTGEL |

TABLE 24

SEQUENCE ID ASSIGNMENTS

| ROBO2-Fc<br>Construct | Full<br>Construct | Leader | SRLRQEDFP<br>(SEQ ID NO: 8) | Ig1 | Ig1-2<br>Linker | Ig2 | Ig2-3<br>Linker | Ig3 | Ig4 | GS<br>Linker | IgG1<br>Fc 3mut |
|---|---|---|---|---|---|---|---|---|---|---|---|
| ROBO2-Fc 1.0 | 5 | 18 | X | 9 | X | X | X | X | X | 15 | 16 |
| ROBO2-FC 1.1 | 4 | 18 | X | 9 | 10 | X | X | X | X | 15 | 16 |

TABLE 24-continued

SEQUENCE ID ASSIGNMENTS

| | | | ROBO2-Fc Component | | | | | | | | |
|---|---|---|---|---|---|---|---|---|---|---|---|
| ROBO2-Fc Construct | Full Construct | Leader | SRLRQEDFP (SEQ ID NO: 8) | Ig1 | Ig1-2 Linker | Ig2 | Ig2-3 Linker | Ig3 | Ig4 | GS Linker | IgG1 Fc 3mut |
| ROBO2-FC 2.0 | 3 | 18 | X | 9 | 10 | 11 | X | X | X | 15 | 16 |
| ROBO2-FC 2.1 | 2 | 18 | X | 9 | 10 | 11 | 12 | X | X | 15 | 16 |
| ROBO2-FC 2.2 | 1 | 17 | 8 | 9 | 10 | 11 | 12 | X | X | 15 | 16 |
| ROBO2-FC 3.0 | 6 | 18 | X | 9 | 10 | 11 | 12 | 13 | X | 15 | 16 |
| ROBO2-FC 4.0 | 7 | 18 | X | 9 | 10 | 11 | 12 | 13 | 14 | 15 | 16 |
| ROBO2-FC S17T R73Y | 19 | 17 | 8 | 20 | 10 | 11 | 12 | X | X | 15 | 16 |

X = COMPONENT NOT PART OF CONSTRUCT

---

The invention claimed is:

1. A recombinant Roundabout Receptor 2 (ROBO2) protein comprising (i) a portion of ROBO2 extracellular domain, and (ii) an immunoglobulin domain, wherein said portion of ROBO2 extracellular domain consists of amino acid residues 1 to 203 according to the numbering of SEQ ID NO: 1.

2. The recombinant ROBO2 protein of claim 1, wherein said immunoglobulin domain is a Fc domain of an $IgA_1$, $IgA_2$, IgD, IgE, IgM, $IgG_1$, $IgG_2$, $IgG_3$, or $IgG_4$.

3. The recombinant ROBO2 protein of claim 2, wherein said Fc domain is the Fc domain of human $IgG_1$.

4. The recombinant ROBO2 protein of claim 3, wherein said human $IgG_1$ Fc domain comprises L234A, L235A, and G237A substitutions (Eu numbering), and does not comprise K447 (Eu numbering).

5. The recombinant ROBO2 protein of claim 4, wherein said Fc domain comprises amino acid residues 210 to 440 according to the numbering of SEQ ID NO: 1.

6. The recombinant ROBO2 protein of claim 1, wherein said amino acid residues 1 to 203 according to the numbering of SEQ ID NO: 1 are contiguous with said immunoglobulin domain.

7. The recombinant ROBO2 protein of claim 1, wherein said amino acid residues 1 to 203 according to the numbering of SEQ ID NO: 1 are connected via a linker to said immunoglobulin domain.

8. The recombinant ROBO2 protein of claim 7, wherein said linker is a peptidyl linker comprising about 1 to 30 amino acid residues.

9. The recombinant ROBO2 protein of claim 8, wherein said peptidyl linker is selected from the group consisting of:
   a) a glycine rich peptide;
   b) a peptide comprising glycine and serine;
   c) a peptide having a sequence [Gly-Gly-Ser]$_n$, wherein n is 1, 2, 3, 4, 5, or 6 (SEQ ID NO: 22); and
   d) a peptide having a sequence [Gly-Gly-Gly-Gly-Ser]$_n$, wherein n is 1, 2, 3, 4, 5, or 6 (SEQ ID NO: 23).

10. The recombinant ROBO2 protein of claim 9, wherein said peptidyl linker is [Gly-Gly-Ser]$_2$ (SEQ ID NO: 15).

11. The recombinant ROBO2 protein of claim 1, wherein said protein binds full-length SLIT2 with a dissociation constant ($K_D$) of about 300 pM, or about 250 pM.

12. The recombinant ROBO2 protein of claim 11, wherein said $K_D$ is measured by surface plasmon resonance (SPR).

13. The recombinant ROBO2 protein of claim 11, wherein said $K_D$ is measured by bio-layer interferometry (BLI), optionally using an eight-channel BLI detection instrument.

14. The recombinant ROBO2 protein of claim 1, wherein said protein inhibits binding of SLIT and ROBO2 and/or inhibits ROBO2-dependent SLIT-N activity.

15. The recombinant ROBO2 protein of claim 1, wherein said protein has a half maximal inhibitory concentration ($IC_{50}$) of about 11 nM, about 9 nM, about 7 nM, about 6 nM, about 5 nM, about 4 nM, about 3 nM, about 2 nM, or about 1 nM, as measured by a homogenous time-resolved fluorescence (HTRF) assay for inhibition of binding of ROBO2 to SLIT2.

16. The recombinant ROBO2 protein of claim 1, wherein said protein has a half maximal inhibitory concentration ($IC_{50}$) of about 55 nM, as assessed by measuring SLIT2-N mediated inhibition of neuronal cell migration.

17. The recombinant ROBO2 protein of claim 1, wherein said protein binds a N-terminal cleavage product of human SLIT2 (SLIT2-N) with a dissociation constant ($K_D$) of about 300 pM, or about 250 pM.

18. The recombinant ROBO2 protein of claim 17, wherein said $K_D$ is measured by surface plasmon resonance (SPR).

19. The recombinant ROBO2 protein of claim 17, wherein said $K_D$ is measured by bio-layer interferometry (BLI), optionally using an eight-channel BLI detection instrument.

20. The recombinant ROBO2 protein of claim 1, wherein said protein binds a N-terminal cleavage product of rat SLIT2 (SLIT2-N) with a dissociation constant ($K_D$) of about 600 pM or about 500 pM.

21. The recombinant ROBO2 protein of claim 1, wherein said protein binds a cleavage product of SLIT2 that comprises the D2 leucine rich repeat domain (SLIT2-D2) with a dissociation constant ($K_D$) of about 300 pM, or about 250 pM.

22. The recombinant ROBO2 protein of claim 21, wherein said $K_D$ is measured by surface plasmon resonance (SPR).

23. The recombinant ROBO2 protein of claim 21, wherein said $K_D$ is measured by bio-layer interferometry (BLI), optionally using an eight-channel BLI detection instrument.

24. An isolated nucleic acid molecule, comprising a nucleotide sequence encoding the recombinant ROBO2 protein of claim 1.

25. The isolated nucleic acid molecule of claim 24, wherein said molecule comprises the nucleic acid sequence of SEQ ID NO: 21.

26. A vector comprising the nucleic acid molecule of claim 24.

27. A host cell comprising the nucleic acid molecule of claim 24.

28. A method of making a recombinant ROBO2 protein comprising culturing the host cell of claim 27 under conditions wherein the recombinant ROBO2 protein is expressed.

29. The method of claim 28, further comprising isolating the recombinant ROBO2 protein.

30. A pharmaceutical composition comprising the recombinant ROBO2 protein of claim 1, and a pharmaceutically acceptable carrier or excipient.

31. A method of treating renal disease, comprising administering to a subject in need thereof a therapeutically effective amount of the recombinant ROBO2 protein of claim 1.

32. The method of claim 31, wherein said renal disease is a glomerular disease, Focal Segmental Glomerular Sclerosis (FSGS), or nephropathy.

33. A recombinant Roundabout Receptor 2 (ROBO2)-Fc protein comprising the amino acid sequence of SEQ ID NO: 1.

34. The recombinant ROBO2 protein of claim 33, comprising the amino acid sequence encoded by the insert of the plasmid deposited at the ATCC and having ATCC Accession No. PTA-124008.

35. A method of treating renal disease, comprising administering to a subject in need thereof a therapeutically effective amount of the recombinant ROBO2 protein of claim 33.

36. The method of claim 35, wherein said renal disease is a glomerular disease, Focal Segmental Glomerular Sclerosis (FSGS), or nephropathy.

37. A method of treating Focal Segmental Glomerular Sclerosis (FSGS), comprising administering to a subject in need thereof a therapeutically effective amount of the recombinant ROBO2 protein of claim 33.

38. A recombinant Roundabout Receptor 2 (ROBO2)-Fc protein comprising an amino acid sequence at least 95% identical to the amino acid sequence of SEQ ID NO: 1.

39. A recombinant Roundabout Receptor 2 (ROBO2) protein consisting of the amino acid sequence of SEQ ID NO: 1.

40. A method of treating renal disease, comprising administering to a subject in need thereof a therapeutically effective amount of the recombinant ROBO2 protein of claim 39.

41. The method of claim 40, wherein said renal disease is a glomerular disease, Focal Segmental Glomerular Sclerosis (FSGS), or nephropathy.

42. A method of treating Focal Segmental Glomerular Sclerosis (FSGS), comprising administering to a subject in need thereof a therapeutically effective amount of the recombinant ROBO2 protein of claim 39.

43. A pharmaceutical composition comprising the recombinant ROBO2 protein of claim 39, and a pharmaceutically acceptable carrier or excipient.

44. An isolated nucleic acid molecule, comprising a nucleotide sequence encoding a recombinant ROBO2 protein, wherein said nucleic acid molecule comprises the nucleic acid sequence of SEQ ID NO: 21.

45. A vector comprising the nucleic acid molecule of claim 44.

46. A host cell comprising the nucleic acid molecule of claim 44.

47. A method of making a recombinant ROBO2 protein comprising culturing the host cell of claim 46 under conditions wherein the recombinant ROBO2 protein is expressed.

48. The method of claim 47, further comprising isolating the recombinant ROBO2 protein.

* * * * *

SEQUENCE LISTING

<160> NUMBER OF SEQ ID NOS: 25

<210> SEQ ID NO 1
<211> LENGTH: 440
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

```
Ser Arg Leu Arg Gln Glu Asp Phe Pro Pro Arg Ile Val Glu His Pro
1               5                   10                  15

Ser Asp Val Ile Val Ser Lys Gly Glu Pro Thr Thr Leu Asn Cys Lys
            20                  25                  30

Ala Glu Gly Arg Pro Thr Pro Thr Ile Glu Trp Tyr Lys Asp Gly Glu
        35                  40                  45

Arg Val Glu Thr Asp Lys Asp Asp Pro Arg Ser His Arg Met Leu Leu
    50                  55                  60

Pro Ser Gly Ser Leu Phe Phe Leu Arg Ile Val His Gly Arg Arg Ser
65                  70                  75                  80

Lys Pro Asp Glu Gly Ser Tyr Val Cys Val Ala Arg Asn Tyr Leu Gly
                85                  90                  95

Glu Ala Val Ser Arg Asn Ala Ser Leu Glu Val Ala Leu Leu Arg Asp
            100                 105                 110

Asp Phe Arg Gln Asn Pro Thr Asp Val Val Val Ala Ala Gly Glu Pro
        115                 120                 125

Ala Ile Leu Glu Cys Gln Pro Pro Arg Gly His Pro Glu Pro Thr Ile
    130                 135                 140

Tyr Trp Lys Lys Asp Lys Val Arg Ile Asp Asp Lys Glu Glu Arg Ile
145                 150                 155                 160

Ser Ile Arg Gly Gly Lys Leu Met Ile Ser Asn Thr Arg Lys Ser Asp
                165                 170                 175

Ala Gly Met Tyr Thr Cys Val Gly Thr Asn Met Val Gly Glu Arg Asp
            180                 185                 190

Ser Asp Pro Ala Glu Leu Thr Val Phe Glu Arg Gly Gly Ser Gly Gly
        195                 200                 205
```

```
Ser Glu Pro Lys Ser Ser Asp Lys Thr His Thr Cys Pro Pro Cys Pro
    210                 215                 220
Ala Pro Glu Ala Ala Gly Ala Pro Ser Val Phe Leu Phe Pro Pro Lys
225                 230                 235                 240
Pro Lys Asp Thr Leu Met Ile Ser Arg Thr Pro Glu Val Thr Cys Val
                245                 250                 255
Val Val Asp Val Ser His Glu Asp Pro Glu Val Lys Phe Asn Trp Tyr
            260                 265                 270
Val Asp Gly Val Glu Val His Asn Ala Lys Thr Lys Pro Arg Glu Glu
        275                 280                 285
Gln Tyr Asn Ser Thr Tyr Arg Val Val Ser Val Leu Thr Val Leu His
    290                 295                 300
Gln Asp Trp Leu Asn Gly Lys Glu Tyr Lys Cys Lys Val Ser Asn Lys
305                 310                 315                 320
Ala Leu Pro Ala Pro Ile Glu Lys Thr Ile Ser Lys Ala Lys Gly Gln
                325                 330                 335
Pro Arg Glu Pro Gln Val Tyr Thr Leu Pro Pro Ser Arg Glu Glu Met
            340                 345                 350
Thr Lys Asn Gln Val Ser Leu Thr Cys Leu Val Lys Gly Phe Tyr Pro
        355                 360                 365
Ser Asp Ile Ala Val Glu Trp Glu Ser Asn Gly Gln Pro Glu Asn Asn
    370                 375                 380
Tyr Lys Thr Thr Pro Pro Val Leu Asp Ser Asp Gly Ser Phe Phe Leu
385                 390                 395                 400
Tyr Ser Lys Leu Thr Val Asp Lys Ser Arg Trp Gln Gln Gly Asn Val
                405                 410                 415
Phe Ser Cys Ser Val Met His Glu Ala Leu His Asn His Tyr Thr Gln
            420                 425                 430
Lys Ser Leu Ser Leu Ser Pro Gly
        435                 440

<210> SEQ ID NO 2
<211> LENGTH: 432
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Pro Arg Ile Val Glu His Pro Ser Asp Val Ile Val Ser Lys Gly Glu
1               5                   10                  15
Pro Thr Thr Leu Asn Cys Lys Ala Glu Gly Arg Pro Thr Pro Thr Ile
                20                  25                  30
Glu Trp Tyr Lys Asp Gly Glu Arg Val Glu Thr Asp Lys Asp Asp Pro
            35                  40                  45
Arg Ser His Arg Met Leu Leu Pro Ser Gly Ser Leu Phe Phe Leu Arg
        50                  55                  60
Ile Val His Gly Arg Arg Ser Lys Pro Asp Glu Gly Ser Tyr Val Cys
65                  70                  75                  80
Val Ala Arg Asn Tyr Leu Gly Glu Ala Val Ser Arg Asn Ala Ser Leu
                85                  90                  95
Glu Val Ala Leu Leu Arg Asp Asp Phe Arg Gln Asn Pro Thr Asp Val
            100                 105                 110
Val Val Ala Ala Gly Glu Pro Ala Ile Leu Glu Cys Gln Pro Pro Arg
        115                 120                 125
```

Gly His Pro Glu Pro Thr Ile Tyr Trp Lys Lys Asp Lys Val Arg Ile
    130                 135                 140

Asp Asp Lys Glu Glu Arg Ile Ser Ile Arg Gly Lys Leu Met Ile
145                 150                 155                 160

Ser Asn Thr Arg Lys Ser Asp Ala Gly Met Tyr Thr Cys Val Gly Thr
                165                 170                 175

Asn Met Val Gly Glu Arg Asp Ser Asp Pro Ala Glu Leu Thr Val Phe
            180                 185                 190

Glu Arg Gly Gly Ser Gly Gly Ser Glu Pro Lys Ser Ser Asp Lys Thr
        195                 200                 205

His Thr Cys Pro Pro Cys Pro Ala Pro Glu Ala Ala Gly Ala Pro Ser
    210                 215                 220

Val Phe Leu Phe Pro Pro Lys Pro Lys Asp Thr Leu Met Ile Ser Arg
225                 230                 235                 240

Thr Pro Glu Val Thr Cys Val Val Val Asp Val Ser His Glu Asp Pro
                245                 250                 255

Glu Val Lys Phe Asn Trp Tyr Val Asp Gly Val Glu Val His Asn Ala
            260                 265                 270

Lys Thr Lys Pro Arg Glu Glu Gln Tyr Asn Ser Thr Tyr Arg Val Val
        275                 280                 285

Ser Val Leu Thr Val Leu His Gln Asp Trp Leu Asn Gly Lys Glu Tyr
    290                 295                 300

Lys Cys Lys Val Ser Asn Lys Ala Leu Pro Ala Pro Ile Glu Lys Thr
305                 310                 315                 320

Ile Ser Lys Ala Lys Gly Gln Pro Arg Glu Pro Gln Val Tyr Thr Leu
                325                 330                 335

Pro Pro Ser Arg Glu Glu Met Thr Lys Asn Gln Val Ser Leu Thr Cys
            340                 345                 350

Leu Val Lys Gly Phe Tyr Pro Ser Asp Ile Ala Val Glu Trp Glu Ser
        355                 360                 365

Asn Gly Gln Pro Glu Asn Asn Tyr Lys Thr Thr Pro Pro Val Leu Asp
    370                 375                 380

Ser Asp Gly Ser Phe Phe Leu Tyr Ser Lys Leu Thr Val Asp Lys Ser
385                 390                 395                 400

Arg Trp Gln Gln Gly Asn Val Phe Ser Cys Ser Val Met His Glu Ala
                405                 410                 415

Leu His Asn His Tyr Thr Gln Lys Ser Leu Ser Leu Ser Pro Gly Lys
            420                 425                 430

<210> SEQ ID NO 3
<211> LENGTH: 428
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Pro Arg Ile Val Glu His Pro Ser Asp Val Ile Val Ser Lys Gly Glu
1               5                   10                  15

Pro Thr Thr Leu Asn Cys Lys Ala Glu Gly Arg Pro Thr Pro Thr Ile
                20                  25                  30

Glu Trp Tyr Lys Asp Gly Glu Arg Val Glu Thr Asp Lys Asp Asp Pro
            35                  40                  45

Arg Ser His Arg Met Leu Leu Pro Ser Gly Ser Leu Phe Phe Leu Arg

```
                   50                  55                  60
Ile Val His Gly Arg Arg Ser Lys Pro Asp Glu Gly Ser Tyr Val Cys
 65                  70                  75                  80

Val Ala Arg Asn Tyr Leu Gly Glu Ala Val Ser Arg Asn Ala Ser Leu
                 85                  90                  95

Glu Val Ala Leu Leu Arg Asp Asp Phe Arg Gln Asn Pro Thr Asp Val
                100                 105                 110

Val Val Ala Ala Gly Glu Pro Ala Ile Leu Glu Cys Gln Pro Pro Arg
                115                 120                 125

Gly His Pro Glu Pro Thr Ile Tyr Trp Lys Lys Asp Lys Val Arg Ile
            130                 135                 140

Asp Asp Lys Glu Glu Arg Ile Ser Ile Arg Gly Gly Lys Leu Met Ile
145                 150                 155                 160

Ser Asn Thr Arg Lys Ser Asp Ala Gly Met Tyr Thr Cys Val Gly Thr
                165                 170                 175

Asn Met Val Gly Glu Arg Asp Ser Asp Pro Ala Glu Leu Thr Gly Gly
            180                 185                 190

Ser Gly Gly Ser Glu Pro Lys Ser Ser Asp Lys Thr His Thr Cys Pro
            195                 200                 205

Pro Cys Pro Ala Pro Glu Ala Ala Gly Ala Pro Ser Val Phe Leu Phe
            210                 215                 220

Pro Pro Lys Pro Lys Asp Thr Leu Met Ile Ser Arg Thr Pro Glu Val
225                 230                 235                 240

Thr Cys Val Val Val Asp Val Ser His Glu Asp Pro Glu Val Lys Phe
                245                 250                 255

Asn Trp Tyr Val Asp Gly Val Glu Val His Asn Ala Lys Thr Lys Pro
                260                 265                 270

Arg Glu Glu Gln Tyr Asn Ser Thr Tyr Arg Val Val Ser Val Leu Thr
            275                 280                 285

Val Leu His Gln Asp Trp Leu Asn Gly Lys Glu Tyr Lys Cys Lys Val
            290                 295                 300

Ser Asn Lys Ala Leu Pro Ala Pro Ile Glu Lys Thr Ile Ser Lys Ala
305                 310                 315                 320

Lys Gly Gln Pro Arg Glu Pro Gln Val Tyr Thr Leu Pro Pro Ser Arg
                325                 330                 335

Glu Glu Met Thr Lys Asn Gln Val Ser Leu Thr Cys Leu Val Lys Gly
            340                 345                 350

Phe Tyr Pro Ser Asp Ile Ala Val Glu Trp Glu Ser Asn Gly Gln Pro
            355                 360                 365

Glu Asn Asn Tyr Lys Thr Thr Pro Pro Val Leu Asp Ser Asp Gly Ser
370                 375                 380

Phe Phe Leu Tyr Ser Lys Leu Thr Val Asp Lys Ser Arg Trp Gln Gln
385                 390                 395                 400

Gly Asn Val Phe Ser Cys Ser Val Met His Glu Ala Leu His Asn His
                405                 410                 415

Tyr Thr Gln Lys Ser Leu Ser Leu Ser Pro Gly Lys
            420                 425

<210> SEQ ID NO 4
<211> LENGTH: 340
<212> TYPE: PRT
<213> ORGANISM: Artificial Sequence
<220> FEATURE:
<223> OTHER INFORMATION: Description of Artificial Sequence: Synthetic
      polypeptide
```

```
<400> SEQUENCE: 4

Pro Arg Ile Val Glu His Pro Ser Asp Val Ile Val Ser Lys Gly Glu
1               5                   10                  15

Pro Thr Thr Leu Asn Cys Lys Ala Glu Gly Arg Pro Thr Pro Thr Ile
            20                  25                  30

Glu Trp Tyr Lys Asp Gly Glu Arg Val Glu Thr Asp Lys Asp Asp Pro
        35                  40                  45

Arg Ser His Arg Met Leu Leu Pro Ser Gly Ser Leu Phe Phe Leu Arg
    50                  55                  60

Ile Val His Gly Arg Arg Ser Lys Pro Asp Glu Gly Ser Tyr Val Cys
65                  70                  75                  80

Val Ala Arg Asn Tyr Leu Gly Glu Ala Val Ser Arg Asn Ala Ser Leu
                85                  90                  95

Glu Val Ala Leu Leu Arg Gly Gly Ser Gly Ser Glu Pro Lys Ser
            100                 105                 110

Ser Asp Lys Thr His Thr Cys Pro Pro Cys Pro Ala Pro Glu Ala Ala
            115                 120                 125

Gly Ala Pro Ser Val Phe Leu Phe Pro Pro Lys Pro Lys Asp Thr Leu
130                 135                 140

Met Ile Ser Arg Thr Pro Glu Val Thr Cys Val Val Asp Val Ser
145                 150                 155                 160

His Glu Asp Pro Glu Val Lys Phe Asn Trp Tyr Val Asp Gly Val Glu
                165                 170                 175

Val His Asn Ala Lys Thr Lys Pro Arg Glu Glu Gln Tyr Asn Ser Thr
            180                 185                 190

Tyr Arg Val Val Ser Val Leu Thr Val Leu His Gln Asp Trp Leu Asn
        195                 200                 205

Gly Lys Glu Tyr Lys Cys Lys Val Ser Asn Lys Ala Leu Pro Ala Pro
    210                 215                 220

Ile Glu Lys Thr Ile Ser Lys Ala Lys Gly Gln Pro Arg Glu Pro Gln
225                 230                 235                 240

Val Tyr Thr Leu Pro Pro Ser Arg Glu Glu Met Thr Lys Asn Gln Val
                245                 250                 255

Ser Leu Thr Cys Leu Val Lys Gly Phe Tyr Pro Ser Asp Ile Ala Val
            260                 265                 270

Glu Trp Glu Ser Asn Gly Gln Pro Glu Asn Asn Tyr Lys Thr Thr Pro
        275                 280                 285

Pro Val Leu Asp Ser Asp Gly Ser Phe Phe Leu Tyr Ser Lys Leu Thr
    290                 295                 300

Val Asp Lys Ser Arg Trp Gln Gln Gly Asn Val Phe Ser Cys Ser Val
305                 310                 315                 320

Met His Glu Ala Leu His Asn His Tyr Thr Gln Lys Ser Leu Ser Leu
                325                 330                 335

Ser Pro Gly Lys
            340

<210> SEQ ID NO 5
<211> LENGTH: 335
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5
```

```
Pro Arg Ile Val Glu His Pro Ser Asp Val Ile Val Ser Lys Gly Glu
1               5                   10                  15

Pro Thr Thr Leu Asn Cys Lys Ala Glu Gly Arg Pro Thr Pro Thr Ile
            20                  25                  30

Glu Trp Tyr Lys Asp Gly Glu Arg Val Glu Thr Asp Lys Asp Asp Pro
        35                  40                  45

Arg Ser His Arg Met Leu Leu Pro Ser Gly Ser Leu Phe Phe Leu Arg
    50                  55                  60

Ile Val His Gly Arg Arg Ser Lys Pro Asp Glu Gly Ser Tyr Val Cys
65                  70                  75                  80

Val Ala Arg Asn Tyr Leu Gly Glu Ala Val Ser Arg Asn Ala Ser Leu
                85                  90                  95

Glu Gly Gly Ser Gly Gly Ser Glu Pro Lys Ser Ser Asp Lys Thr His
            100                 105                 110

Thr Cys Pro Pro Cys Pro Ala Pro Glu Ala Ala Gly Ala Pro Ser Val
        115                 120                 125

Phe Leu Phe Pro Pro Lys Pro Lys Asp Thr Leu Met Ile Ser Arg Thr
130                 135                 140

Pro Glu Val Thr Cys Val Val Asp Val Ser His Glu Asp Pro Glu
145                 150                 155                 160

Val Lys Phe Asn Trp Tyr Val Asp Gly Val Glu Val His Asn Ala Lys
                165                 170                 175

Thr Lys Pro Arg Glu Glu Gln Tyr Asn Ser Thr Tyr Arg Val Val Ser
            180                 185                 190

Val Leu Thr Val Leu His Gln Asp Trp Leu Asn Gly Lys Glu Tyr Lys
        195                 200                 205

Cys Lys Val Ser Asn Lys Ala Leu Pro Ala Pro Ile Glu Lys Thr Ile
210                 215                 220

Ser Lys Ala Lys Gly Gln Pro Arg Glu Pro Gln Val Tyr Thr Leu Pro
225                 230                 235                 240

Pro Ser Arg Glu Glu Met Thr Lys Asn Gln Val Ser Leu Thr Cys Leu
                245                 250                 255

Val Lys Gly Phe Tyr Pro Ser Asp Ile Ala Val Glu Trp Glu Ser Asn
            260                 265                 270

Gly Gln Pro Glu Asn Asn Tyr Lys Thr Thr Pro Pro Val Leu Asp Ser
        275                 280                 285

Asp Gly Ser Phe Phe Leu Tyr Ser Lys Leu Thr Val Asp Lys Ser Arg
290                 295                 300

Trp Gln Gln Gly Asn Val Phe Ser Cys Ser Val Met His Glu Ala Leu
305                 310                 315                 320

His Asn His Tyr Thr Gln Lys Ser Leu Ser Leu Ser Pro Gly Lys
                325                 330                 335

<210> SEQ ID NO 6
<211> LENGTH: 517
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Pro Arg Ile Val Glu His Pro Ser Asp Val Ile Val Ser Lys Gly Glu
1               5                   10                  15

Pro Thr Thr Leu Asn Cys Lys Ala Glu Gly Arg Pro Thr Pro Thr Ile
```

-continued

```
                20                  25                  30
Glu Trp Tyr Lys Asp Gly Glu Arg Val Glu Thr Asp Lys Asp Pro
            35                  40                  45
Arg Ser His Arg Met Leu Leu Pro Ser Gly Ser Leu Phe Leu Arg
        50                  55                  60
Ile Val His Gly Arg Arg Ser Lys Pro Asp Glu Gly Ser Tyr Val Cys
65                  70                  75                  80
Val Ala Arg Asn Tyr Leu Gly Glu Ala Val Ser Arg Asn Ala Ser Leu
                85                  90                  95
Glu Val Ala Leu Leu Arg Asp Asp Phe Arg Gln Asn Pro Thr Asp Val
            100                 105                 110
Val Val Ala Ala Gly Glu Pro Ala Ile Leu Glu Cys Gln Pro Pro Arg
        115                 120                 125
Gly His Pro Glu Pro Thr Ile Tyr Trp Lys Lys Asp Lys Val Arg Ile
        130                 135                 140
Asp Asp Lys Glu Glu Arg Ile Ser Ile Arg Gly Gly Lys Leu Met Ile
145                 150                 155                 160
Ser Asn Thr Arg Lys Ser Asp Ala Gly Met Tyr Thr Cys Val Gly Thr
                165                 170                 175
Asn Met Val Gly Glu Arg Asp Ser Asp Pro Ala Glu Leu Thr Val Phe
            180                 185                 190
Glu Arg Pro Thr Phe Leu Arg Arg Pro Ile Asn Gln Val Val Leu Glu
        195                 200                 205
Glu Glu Ala Val Glu Phe Arg Cys Gln Val Gln Gly Asp Pro Gln Pro
        210                 215                 220
Thr Val Arg Trp Lys Lys Asp Asp Ala Asp Leu Pro Arg Gly Arg Tyr
225                 230                 235                 240
Asp Ile Lys Asp Asp Tyr Thr Leu Arg Ile Lys Lys Thr Met Ser Thr
                245                 250                 255
Asp Glu Gly Thr Tyr Met Cys Ile Ala Glu Asn Arg Val Gly Lys Met
            260                 265                 270
Glu Ala Ser Ala Thr Leu Thr Gly Gly Ser Gly Gly Ser Glu Pro Lys
        275                 280                 285
Ser Ser Asp Lys Thr His Thr Cys Pro Pro Cys Pro Ala Pro Glu Ala
        290                 295                 300
Ala Gly Ala Pro Ser Val Phe Leu Phe Pro Pro Lys Pro Lys Asp Thr
305                 310                 315                 320
Leu Met Ile Ser Arg Thr Pro Glu Val Thr Cys Val Val Val Asp Val
                325                 330                 335
Ser His Glu Asp Pro Glu Val Lys Phe Asn Trp Tyr Val Asp Gly Val
            340                 345                 350
Glu Val His Asn Ala Lys Thr Lys Pro Arg Glu Glu Gln Tyr Asn Ser
        355                 360                 365
Thr Tyr Arg Val Val Ser Val Leu Thr Val Leu His Gln Asp Trp Leu
        370                 375                 380
Asn Gly Lys Glu Tyr Lys Cys Lys Val Ser Asn Lys Ala Leu Pro Ala
385                 390                 395                 400
Pro Ile Glu Lys Thr Ile Ser Lys Ala Lys Gly Gln Pro Arg Glu Pro
                405                 410                 415
Gln Val Tyr Thr Leu Pro Pro Ser Arg Glu Glu Met Thr Lys Asn Gln
            420                 425                 430
Val Ser Leu Thr Cys Leu Val Lys Gly Phe Tyr Pro Ser Asp Ile Ala
        435                 440                 445
```

Val Glu Trp Glu Ser Asn Gly Gln Pro Glu Asn Asn Tyr Lys Thr Thr
            450                 455                 460

Pro Pro Val Leu Asp Ser Asp Gly Ser Phe Phe Leu Tyr Ser Lys Leu
465                 470                 475                 480

Thr Val Asp Lys Ser Arg Trp Gln Gln Gly Asn Val Phe Ser Cys Ser
                485                 490                 495

Val Met His Glu Ala Leu His Asn His Tyr Thr Gln Lys Ser Leu Ser
            500                 505                 510

Leu Ser Pro Gly Lys
            515

<210> SEQ ID NO 7
<211> LENGTH: 617
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Pro Arg Ile Val Glu His Pro Ser Asp Val Ile Val Ser Lys Gly Glu
1               5                   10                  15

Pro Thr Thr Leu Asn Cys Lys Ala Glu Gly Arg Pro Thr Pro Thr Ile
            20                  25                  30

Glu Trp Tyr Lys Asp Gly Glu Val Glu Thr Asp Lys Asp Asp Pro
            35                  40                  45

Arg Ser His Arg Met Leu Leu Pro Ser Gly Ser Leu Phe Phe Leu Arg
50                  55                  60

Ile Val His Gly Arg Arg Ser Lys Pro Asp Glu Gly Ser Tyr Val Cys
65                  70                  75                  80

Val Ala Arg Asn Tyr Leu Gly Glu Ala Val Ser Arg Asn Ala Ser Leu
                85                  90                  95

Glu Val Ala Leu Leu Arg Asp Asp Phe Arg Gln Asn Pro Thr Asp Val
            100                 105                 110

Val Val Ala Ala Gly Glu Pro Ala Ile Leu Glu Cys Gln Pro Pro Arg
        115                 120                 125

Gly His Pro Glu Pro Thr Ile Tyr Trp Lys Lys Asp Lys Val Arg Ile
    130                 135                 140

Asp Asp Lys Glu Glu Arg Ile Ser Ile Arg Gly Gly Lys Leu Met Ile
145                 150                 155                 160

Ser Asn Thr Arg Lys Ser Asp Ala Gly Met Tyr Thr Cys Val Gly Thr
                165                 170                 175

Asn Met Val Gly Glu Arg Asp Ser Asp Pro Ala Glu Leu Thr Val Phe
            180                 185                 190

Glu Arg Pro Thr Phe Leu Arg Arg Pro Ile Asn Gln Val Val Leu Glu
        195                 200                 205

Glu Glu Ala Val Glu Phe Arg Cys Gln Val Gln Gly Asp Pro Gln Pro
    210                 215                 220

Thr Val Arg Trp Lys Lys Asp Asp Ala Asp Leu Pro Arg Gly Arg Tyr
225                 230                 235                 240

Asp Ile Lys Asp Asp Tyr Thr Leu Arg Ile Lys Lys Thr Met Ser Thr
                245                 250                 255

Asp Glu Gly Thr Tyr Met Cys Ile Ala Glu Asn Arg Val Gly Lys Met
            260                 265                 270

Glu Ala Ser Ala Thr Leu Thr Val Arg Ala Pro Pro Gln Phe Val Val

```
            275                 280                 285
Arg Pro Arg Asp Gln Ile Val Ala Gln Gly Arg Thr Val Thr Phe Pro
    290                 295                 300

Cys Glu Thr Lys Gly Asn Pro Gln Pro Ala Val Phe Trp Gln Lys Glu
305                 310                 315                 320

Gly Ser Gln Asn Leu Leu Phe Pro Asn Gln Pro Gln Pro Asn Ser
            325                 330                 335

Arg Cys Ser Val Ser Pro Thr Gly Asp Leu Thr Ile Thr Asn Ile Gln
                340                 345                 350

Arg Ser Asp Ala Gly Tyr Tyr Ile Cys Gln Ala Leu Thr Val Ala Gly
            355                 360                 365

Ser Ile Leu Ala Lys Ala Gln Leu Glu Val Thr Gly Gly Ser Gly Gly
            370                 375                 380

Ser Glu Pro Lys Ser Ser Asp Lys Thr His Thr Cys Pro Pro Cys Pro
385                 390                 395                 400

Ala Pro Glu Ala Ala Gly Ala Pro Ser Val Phe Leu Phe Pro Pro Lys
                405                 410                 415

Pro Lys Asp Thr Leu Met Ile Ser Arg Thr Pro Glu Val Thr Cys Val
            420                 425                 430

Val Val Asp Val Ser His Glu Asp Pro Glu Val Lys Phe Asn Trp Tyr
        435                 440                 445

Val Asp Gly Val Glu Val His Asn Ala Lys Thr Lys Pro Arg Glu Glu
    450                 455                 460

Gln Tyr Asn Ser Thr Tyr Arg Val Val Ser Val Leu Thr Val Leu His
465                 470                 475                 480

Gln Asp Trp Leu Asn Gly Lys Glu Tyr Lys Cys Lys Val Ser Asn Lys
                485                 490                 495

Ala Leu Pro Ala Pro Ile Glu Lys Thr Ile Ser Lys Ala Lys Gly Gln
            500                 505                 510

Pro Arg Glu Pro Gln Val Tyr Thr Leu Pro Pro Ser Arg Glu Glu Met
        515                 520                 525

Thr Lys Asn Gln Val Ser Leu Thr Cys Leu Val Lys Gly Phe Tyr Pro
    530                 535                 540

Ser Asp Ile Ala Val Glu Trp Glu Ser Asn Gly Gln Pro Glu Asn Asn
545                 550                 555                 560

Tyr Lys Thr Thr Pro Pro Val Leu Asp Ser Asp Gly Ser Phe Phe Leu
                565                 570                 575

Tyr Ser Lys Leu Thr Val Asp Lys Ser Arg Trp Gln Gln Gly Asn Val
            580                 585                 590

Phe Ser Cys Ser Val Met His Glu Ala Leu His Asn His Tyr Thr Gln
        595                 600                 605

Lys Ser Leu Ser Leu Ser Pro Gly Lys
    610                 615

<210> SEQ ID NO 8
<211> LENGTH: 9
<212> TYPE: PRT
<213> ORGANISM: Homo sapiens

<400> SEQUENCE: 8

Ser Arg Leu Arg Gln Glu Asp Phe Pro
1               5

<210> SEQ ID NO 9
<211> LENGTH: 97
```

```
<212> TYPE: PRT
<213> ORGANISM: Homo sapiens

<400> SEQUENCE: 9

Pro Arg Ile Val Glu His Pro Ser Asp Val Ile Val Ser Lys Gly Glu
1               5                   10                  15

Pro Thr Thr Leu Asn Cys Lys Ala Glu Gly Arg Pro Thr Pro Thr Ile
                20                  25                  30

Glu Trp Tyr Lys Asp Gly Glu Arg Val Glu Thr Asp Lys Asp Asp Pro
            35                  40                  45

Arg Ser His Arg Met Leu Leu Pro Ser Gly Ser Leu Phe Phe Leu Arg
        50                  55                  60

Ile Val His Gly Arg Arg Ser Lys Pro Asp Glu Gly Ser Tyr Val Cys
65                  70                  75                  80

Val Ala Arg Asn Tyr Leu Gly Glu Ala Val Ser Arg Asn Ala Ser Leu
                85                  90                  95

Glu

<210> SEQ ID NO 10
<211> LENGTH: 5
<212> TYPE: PRT
<213> ORGANISM: Homo sapiens

<400> SEQUENCE: 10

Val Ala Leu Leu Arg
1               5

<210> SEQ ID NO 11
<211> LENGTH: 88
<212> TYPE: PRT
<213> ORGANISM: Homo sapiens

<400> SEQUENCE: 11

Asp Asp Phe Arg Gln Asn Pro Thr Asp Val Val Ala Ala Gly Glu
1               5                   10                  15

Pro Ala Ile Leu Glu Cys Gln Pro Pro Arg Gly His Pro Glu Pro Thr
                20                  25                  30

Ile Tyr Trp Lys Lys Asp Lys Val Arg Ile Asp Asp Lys Glu Glu Arg
            35                  40                  45

Ile Ser Ile Arg Gly Gly Lys Leu Met Ile Ser Asn Thr Arg Lys Ser
        50                  55                  60

Asp Ala Gly Met Tyr Thr Cys Val Gly Thr Asn Met Val Gly Glu Arg
65                  70                  75                  80

Asp Ser Asp Pro Ala Glu Leu Thr
                85

<210> SEQ ID NO 12
<211> LENGTH: 4
<212> TYPE: PRT
<213> ORGANISM: Homo sapiens

<400> SEQUENCE: 12

Val Phe Glu Arg
1

<210> SEQ ID NO 13
<211> LENGTH: 85
<212> TYPE: PRT
<213> ORGANISM: Homo sapiens
```

-continued

<400> SEQUENCE: 13

Pro Thr Phe Leu Arg Arg Pro Ile Asn Gln Val Val Leu Glu Glu
1               5                   10                  15

Ala Val Glu Phe Arg Cys Gln Val Gln Gly Asp Pro Gln Pro Thr Val
                20                  25                  30

Arg Trp Lys Lys Asp Asp Ala Asp Leu Pro Arg Gly Arg Tyr Asp Ile
            35                  40                  45

Lys Asp Asp Tyr Thr Leu Arg Ile Lys Lys Thr Met Ser Thr Asp Glu
50                  55                  60

Gly Thr Tyr Met Cys Ile Ala Glu Asn Arg Val Gly Lys Met Glu Ala
65                  70                  75                  80

Ser Ala Thr Leu Thr
                85

<210> SEQ ID NO 14
<211> LENGTH: 100
<212> TYPE: PRT
<213> ORGANISM: Homo sapiens

<400> SEQUENCE: 14

Val Arg Ala Pro Pro Gln Phe Val Arg Pro Arg Asp Gln Ile Val
1               5                   10                  15

Ala Gln Gly Arg Thr Val Thr Phe Pro Cys Glu Thr Lys Gly Asn Pro
                20                  25                  30

Gln Pro Ala Val Phe Trp Gln Lys Glu Gly Ser Gln Asn Leu Leu Phe
            35                  40                  45

Pro Asn Gln Pro Gln Pro Asn Ser Arg Cys Ser Val Ser Pro Thr
50                  55                  60

Gly Asp Leu Thr Ile Thr Asn Ile Gln Arg Ser Asp Ala Gly Tyr Tyr
65                  70                  75                  80

Ile Cys Gln Ala Leu Thr Val Ala Gly Ser Ile Leu Ala Lys Ala Gln
                85                  90                  95

Leu Glu Val Thr
            100

<210> SEQ ID NO 15
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Gly Gly Ser Gly Gly Ser
1               5

<210> SEQ ID NO 16
<211> LENGTH: 232
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Glu Pro Lys Ser Ser Asp Lys Thr His Thr Cys Pro Pro Cys Pro Ala
1               5                   10                  15

Pro Glu Ala Ala Gly Ala Pro Ser Val Phe Leu Phe Pro Pro Lys Pro
                20                  25                  30

-continued

Lys Asp Thr Leu Met Ile Ser Arg Thr Pro Glu Val Thr Cys Val Val
         35                  40                  45

Val Asp Val Ser His Glu Asp Pro Glu Val Lys Phe Asn Trp Tyr Val
 50                  55                  60

Asp Gly Val Glu Val His Asn Ala Lys Thr Lys Pro Arg Glu Glu Gln
 65                  70                  75                  80

Tyr Asn Ser Thr Tyr Arg Val Val Ser Val Leu Thr Val Leu His Gln
             85                   90                  95

Asp Trp Leu Asn Gly Lys Glu Tyr Lys Cys Lys Val Ser Asn Lys Ala
             100                 105                 110

Leu Pro Ala Pro Ile Glu Lys Thr Ile Ser Lys Ala Lys Gly Gln Pro
             115                 120                 125

Arg Glu Pro Gln Val Tyr Thr Leu Pro Pro Ser Arg Glu Glu Met Thr
             130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
             165                 170                 175

Lys Thr Thr Pro Pro Val Leu Asp Ser Asp Gly Ser Phe Phe Leu Tyr
             180                 185                 190

Ser Lys Leu Thr Val Asp Lys Ser Arg Trp Gln Gln Gly Asn Val Phe
             195                 200                 205

Ser Cys Ser Val Met His Glu Ala Leu His Asn His Tyr Thr Gln Lys
             210                 215                 220

Ser Leu Ser Leu Ser Pro Gly Lys
225                 230

<210> SEQ ID NO 17
<211> LENGTH: 21
<212> TYPE: PRT
<213> ORGANISM: Homo sapiens

<400> SEQUENCE: 17

Met Ser Leu Leu Met Phe Thr Gln Leu Leu Cys Gly Phe Leu Tyr
1               5                   10                  15

Val Arg Val Asp Gly
             20

<210> SEQ ID NO 18
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Met Gly Trp Ser Cys Ile Ile Phe Leu Val Ala Thr Ala Gly Ala His
1               5                   10                  15

Ser

<210> SEQ ID NO 19
<211> LENGTH: 441
<212> TYPE: PRT
<213> ORGANISM: Artificial Sequence
<220> FEATURE:
<223> OTHER INFORMATION: Description of Artificial Sequence: Synthetic
      polypeptide

```
<400> SEQUENCE: 19

Ser Arg Leu Arg Gln Glu Asp Phe Pro Pro Arg Ile Val Glu His Pro
1               5                   10                  15

Thr Asp Val Ile Val Ser Lys Gly Glu Pro Thr Thr Leu Asn Cys Lys
            20                  25                  30

Ala Glu Gly Arg Pro Thr Pro Thr Ile Glu Trp Tyr Lys Asp Gly Glu
        35                  40                  45

Arg Val Glu Thr Asp Lys Asp Asp Pro Arg Ser His Arg Met Leu Leu
    50                  55                  60

Pro Ser Gly Ser Leu Phe Phe Leu Tyr Ile Val His Gly Arg Arg Ser
65                  70                  75                  80

Lys Pro Asp Glu Gly Ser Tyr Val Cys Val Ala Arg Asn Tyr Leu Gly
                85                  90                  95

Glu Ala Val Ser Arg Asn Ala Ser Leu Glu Val Ala Leu Leu Arg Asp
            100                 105                 110

Asp Phe Arg Gln Asn Pro Thr Asp Val Val Ala Ala Gly Glu Pro
        115                 120                 125

Ala Ile Leu Glu Cys Gln Pro Pro Arg Gly His Pro Glu Pro Thr Ile
    130                 135                 140

Tyr Trp Lys Lys Asp Lys Val Arg Ile Asp Asp Lys Glu Glu Arg Ile
145                 150                 155                 160

Ser Ile Arg Gly Gly Lys Leu Met Ile Ser Asn Thr Arg Lys Ser Asp
                165                 170                 175

Ala Gly Met Tyr Thr Cys Val Gly Thr Asn Met Val Gly Glu Arg Asp
            180                 185                 190

Ser Asp Pro Ala Glu Leu Thr Val Phe Glu Arg Gly Gly Ser Gly Gly
        195                 200                 205

Ser Glu Pro Lys Ser Ser Asp Lys Thr His Thr Cys Pro Pro Cys Pro
    210                 215                 220

Ala Pro Glu Ala Ala Gly Ala Pro Ser Val Phe Leu Phe Pro Pro Lys
225                 230                 235                 240

Pro Lys Asp Thr Leu Met Ile Ser Arg Thr Pro Glu Val Thr Cys Val
                245                 250                 255

Val Val Asp Val Ser His Glu Asp Pro Glu Val Lys Phe Asn Trp Tyr
            260                 265                 270

Val Asp Gly Val Glu Val His Asn Ala Lys Thr Lys Pro Arg Glu Glu
        275                 280                 285

Gln Tyr Asn Ser Thr Tyr Arg Val Val Ser Val Leu Thr Val Leu His
    290                 295                 300

Gln Asp Trp Leu Asn Gly Lys Glu Tyr Lys Cys Lys Val Ser Asn Lys
305                 310                 315                 320

Ala Leu Pro Ala Pro Ile Glu Lys Thr Ile Ser Lys Ala Lys Gly Gln
                325                 330                 335

Pro Arg Glu Pro Gln Val Tyr Thr Leu Pro Pro Ser Arg Glu Glu Met
            340                 345                 350

Thr Lys Asn Gln Val Ser Leu Thr Cys Leu Val Lys Gly Phe Tyr Pro
        355                 360                 365

Ser Asp Ile Ala Val Glu Trp Glu Ser Asn Gly Gln Pro Glu Asn Asn
    370                 375                 380

Tyr Lys Thr Thr Pro Pro Val Leu Asp Ser Asp Gly Ser Phe Phe Leu
385                 390                 395                 400

Tyr Ser Lys Leu Thr Val Asp Lys Ser Arg Trp Gln Gln Gly Asn Val
                405                 410                 415
```

Phe Ser Cys Ser Val Met His Glu Ala Leu His Asn His Tyr Thr Gln
              420                 425                 430

Lys Ser Leu Ser Leu Ser Pro Gly Lys
        435                 440

<210> SEQ ID NO 20
<211> LENGTH: 97
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Pro Arg Ile Val Glu His Pro Thr Asp Val Ile Val Ser Lys Gly Glu
1               5                   10                  15

Pro Thr Thr Leu Asn Cys Lys Ala Glu Gly Arg Pro Thr Pro Thr Ile
            20                  25                  30

Glu Trp Tyr Lys Asp Gly Glu Arg Val Glu Thr Asp Lys Asp Asp Pro
        35                  40                  45

Arg Ser His Arg Met Leu Leu Pro Ser Gly Ser Leu Phe Phe Leu Tyr
    50                  55                  60

Ile Val His Gly Arg Arg Ser Lys Pro Asp Glu Gly Ser Tyr Val Cys
65                  70                  75                  80

Val Ala Arg Asn Tyr Leu Gly Glu Ala Val Ser Arg Asn Ala Ser Leu
                85                  90                  95

Glu

<210> SEQ ID NO 21
<211> LENGTH: 1320
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 21
tcgcgtcttc gccaggagga ctttcccccg cggattgtgg agcatccttc cgatgtcatc      60
gtctctaagg gcgagcccac gactctgaac tgcaaggcgg agggccggcc aacgcccacc     120
attgagtggt acaaagatgg ggagcgagtg gagactgaca aggacgatcc ccggtcccac     180
aggatgcttc tgcccagcgg atccttattc ttcttgcgca tcgtgcacgg cgcaggagt      240 aaacctgatg aaggaagcta cgtttgtgtt gcgaggaact atcttggtga agcagtgagt     300
cgaaatgcgt ctctggaagt ggcattgtta cgagatgact ccgacaaaa ccccacagat     360 gttgtagtgg cagctggaga gcctgcaatc ctggagtgcc agcctccccg ggacacccca    420
gaacccacca tctactggaa aaaagacaaa gttcgaattg atgacaagga agaaagaata    480
agtatccgtg gtggaaaact gatgatctcc aataccagga aaagtgatgc agggatgtat    540
acttgtgttg gtaccaatat ggtgggagaa agggacagtg acccagcaga gctgactgtc    600
tttgaacgag gcggcagcgg cggcagcgag cccaaatctt ctgacaaaac tcacacatgc    660
ccaccgtgcc cagcacctga gctgcaggg gcaccgtcag tcttcctctt ccccccaaaa    720
cccaaggaca ccctcatgat ctcccggacc cctgaggtca catgcgtggt ggtggacgtg    780
agccacgaag accctgaggt caagttcaac tggtacgtgg acggcgtgga ggtgcataat    840
gccaagacaa agccgcggga ggagcagtac aacagcacgt accgtgtggt cagcgtcctc    900

```
accgtcctgc accaggactg gctgaatggc aaggagtaca agtgcaaggt ctccaacaaa    960
gccctcccag ccccccatcga gaaaaccatc tccaaagcca aagggcagcc ccgagaacca   1020
caggtgtaca ccctgccccc atcccgggag gagatgacca agaaccaggt cagcctgacc   1080
tgcctggtca aaggcttcta tcccagcgac atcgccgtgg agtgggagag caatgggcag   1140
ccggagaaca actacaagac cacgcctccc gtgctggact ccgacggctc cttcttcctc   1200
tatagcaagc tcaccgtgga caagagcagg tggcagcagg ggaacgtctt ctcatgctcc   1260
gtgatgcatg aggctctgca caaccactac acgcagaaga gcctctccct gtccccggga   1320
```

```
<210> SEQ ID NO 22
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(18)
<223> OTHER INFORMATION: This sequence may encompass 1-6 "Gly Gly Ser"
      repeating units

<400> SEQUENCE: 22

Gly Gly Ser Gly Gly Ser Gly Gly Ser Gly Gly Ser Gly Gly Ser Gly
1               5                   10                  15

Gly Ser

<210> SEQ ID NO 23
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(30)
<223> OTHER INFORMATION: This sequence may encompass 1-6 "Gly Gly Gly
      Gly Ser" repeating units

<400> SEQUENCE: 23

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser
            20                  25                  30

<210> SEQ ID NO 24
<211> LENGTH: 1378
<212> TYPE: PRT
<213> ORGANISM: Homo sapiens

<400> SEQUENCE: 24

Met Ser Leu Leu Met Phe Thr Gln Leu Leu Leu Cys Gly Phe Leu Tyr
1               5                   10                  15

Val Arg Val Asp Gly Ser Arg Leu Arg Gln Glu Asp Phe Pro Pro Arg
            20                  25                  30

Ile Val Glu His Pro Ser Asp Val Ile Val Ser Lys Gly Glu Pro Thr
        35                  40                  45

Thr Leu Asn Cys Lys Ala Glu Gly Arg Pro Thr Pro Thr Ile Glu Trp
    50                  55                  60

Tyr Lys Asp Gly Glu Arg Val Glu Thr Asp Lys Asp Asp Pro Arg Ser
65                  70                  75                  80
```

His Arg Met Leu Leu Pro Ser Gly Ser Leu Phe Phe Leu Arg Ile Val
                85                  90                  95

His Gly Arg Arg Ser Lys Pro Asp Glu Gly Ser Tyr Val Cys Val Ala
            100                 105                 110

Arg Asn Tyr Leu Gly Glu Ala Val Ser Arg Asn Ala Ser Leu Glu Val
        115                 120                 125

Ala Leu Leu Arg Asp Asp Phe Arg Gln Asn Pro Thr Asp Val Val Val
    130                 135                 140

Ala Ala Gly Glu Pro Ala Ile Leu Glu Cys Gln Pro Pro Arg Gly His
145                 150                 155                 160

Pro Glu Pro Thr Ile Tyr Trp Lys Lys Asp Lys Val Arg Ile Asp Asp
                165                 170                 175

Lys Glu Glu Arg Ile Ser Ile Arg Gly Gly Lys Leu Met Ile Ser Asn
            180                 185                 190

Thr Arg Lys Ser Asp Ala Gly Met Tyr Thr Cys Val Gly Thr Asn Met
        195                 200                 205

Val Gly Glu Arg Asp Ser Asp Pro Ala Glu Leu Thr Val Phe Glu Arg
    210                 215                 220

Pro Thr Phe Leu Arg Arg Pro Ile Asn Gln Val Val Leu Glu Glu Glu
225                 230                 235                 240

Ala Val Glu Phe Arg Cys Gln Val Gln Gly Asp Pro Gln Pro Thr Val
                245                 250                 255

Arg Trp Lys Lys Asp Asp Ala Asp Leu Pro Arg Gly Arg Tyr Asp Ile
            260                 265                 270

Lys Asp Asp Tyr Thr Leu Arg Ile Lys Lys Thr Met Ser Thr Asp Glu
        275                 280                 285

Gly Thr Tyr Met Cys Ile Ala Glu Asn Arg Val Gly Lys Met Glu Ala
    290                 295                 300

Ser Ala Thr Leu Thr Val Arg Ala Pro Pro Gln Phe Val Val Arg Pro
305                 310                 315                 320

Arg Asp Gln Ile Val Ala Gln Gly Arg Thr Val Thr Phe Pro Cys Glu
                325                 330                 335

Thr Lys Gly Asn Pro Gln Pro Ala Val Phe Trp Gln Lys Glu Gly Ser
            340                 345                 350

Gln Asn Leu Leu Phe Pro Asn Gln Pro Gln Gln Pro Asn Ser Arg Cys
        355                 360                 365

Ser Val Ser Pro Thr Gly Asp Leu Thr Ile Thr Asn Ile Gln Arg Ser
    370                 375                 380

Asp Ala Gly Tyr Tyr Ile Cys Gln Ala Leu Thr Val Ala Gly Ser Ile
385                 390                 395                 400

Leu Ala Lys Ala Gln Leu Glu Val Thr Asp Val Leu Thr Asp Arg Pro
                405                 410                 415

Pro Pro Ile Ile Leu Gln Gly Pro Ala Asn Gln Thr Leu Ala Val Asp
            420                 425                 430

Gly Thr Ala Leu Leu Lys Cys Lys Ala Thr Gly Asp Pro Leu Pro Val
        435                 440                 445

Ile Ser Trp Leu Lys Glu Gly Phe Thr Phe Pro Gly Arg Asp Pro Arg
    450                 455                 460

Ala Thr Ile Gln Glu Gln Gly Thr Leu Gln Ile Lys Asn Leu Arg Ile
465                 470                 475                 480

Ser Asp Thr Gly Thr Tyr Thr Cys Val Ala Thr Ser Ser Ser Gly Glu
                485                 490                 495

```
Thr Ser Trp Ser Ala Val Leu Asp Val Thr Glu Ser Gly Ala Thr Ile
            500                 505                 510
Ser Lys Asn Tyr Asp Leu Ser Asp Leu Pro Gly Pro Ser Lys Pro
        515                 520                 525
Gln Val Thr Asp Val Thr Lys Asn Ser Val Thr Leu Ser Trp Gln Pro
        530                 535                 540
Gly Thr Pro Gly Thr Leu Pro Ala Ser Ala Tyr Ile Ile Glu Ala Phe
545                 550                 555                 560
Ser Gln Ser Val Ser Asn Ser Trp Gln Thr Val Ala Asn His Val Lys
                565                 570                 575
Thr Thr Leu Tyr Thr Val Arg Gly Leu Arg Pro Asn Thr Ile Tyr Leu
            580                 585                 590
Phe Met Val Arg Ala Ile Asn Pro Gln Gly Leu Ser Asp Pro Ser Pro
            595                 600                 605
Met Ser Asp Pro Val Arg Thr Gln Asp Ile Ser Pro Pro Ala Gln Gly
            610                 615                 620
Val Asp His Arg Gln Val Gln Lys Glu Leu Gly Asp Val Leu Val Arg
625                 630                 635                 640
Leu His Asn Pro Val Val Leu Thr Pro Thr Thr Val Gln Val Thr Trp
                645                 650                 655
Thr Val Asp Arg Gln Pro Gln Phe Ile Gln Gly Tyr Arg Val Met Tyr
            660                 665                 670
Arg Gln Thr Ser Gly Leu Gln Ala Thr Ser Ser Trp Gln Asn Leu Asp
            675                 680                 685
Ala Lys Val Pro Thr Glu Arg Ser Ala Val Leu Val Asn Leu Lys Lys
        690                 695                 700
Gly Val Thr Tyr Glu Ile Lys Val Arg Pro Tyr Phe Asn Glu Phe Gln
705                 710                 715                 720
Gly Met Asp Ser Glu Ser Lys Thr Val Arg Thr Thr Glu Glu Ala Pro
                725                 730                 735
Ser Ala Pro Pro Gln Ser Val Thr Val Leu Thr Val Gly Ser Tyr Asn
            740                 745                 750
Ser Thr Ser Ile Ser Val Ser Trp Asp Pro Pro Pro Pro Asp His Gln
        755                 760                 765
Asn Gly Ile Ile Gln Glu Tyr Lys Ile Trp Cys Leu Gly Asn Glu Thr
        770                 775                 780
Arg Phe His Ile Asn Lys Thr Val Asp Ala Ala Ile Arg Ser Val Ile
785                 790                 795                 800
Ile Gly Gly Leu Phe Pro Gly Ile Gln Tyr Arg Val Glu Val Ala Ala
                805                 810                 815
Ser Thr Ser Ala Gly Val Gly Val Lys Ser Glu Pro Gln Pro Ile Ile
            820                 825                 830
Ile Gly Arg Arg Asn Glu Val Val Ile Thr Glu Asn Asn Ser Ile
        835                 840                 845
Thr Glu Gln Ile Thr Asp Val Val Lys Gln Pro Ala Phe Ile Ala Gly
        850                 855                 860
Ile Gly Gly Ala Cys Trp Val Ile Leu Met Gly Phe Ser Ile Trp Leu
865                 870                 875                 880
Tyr Trp Arg Arg Lys Lys Arg Lys Gly Leu Ser Asn Tyr Ala Val Thr
                885                 890                 895
Phe Gln Arg Gly Asp Gly Gly Leu Met Ser Asn Gly Ser Arg Pro Gly
            900                 905                 910
Leu Leu Asn Ala Gly Asp Pro Ser Tyr Pro Trp Leu Ala Asp Ser Trp
```

-continued

```
            915                 920                 925
Pro Ala Thr Ser Leu Pro Val Asn Asn Ser Asn Ser Gly Pro Asn Glu
    930                 935                 940

Ile Gly Asn Phe Gly Arg Gly Asp Val Leu Pro Pro Val Pro Gly Gln
945                 950                 955                 960

Gly Asp Lys Thr Ala Thr Met Leu Ser Asp Gly Ala Ile Tyr Ser Ser
                965                 970                 975

Ile Asp Phe Thr Thr Lys Thr Ser Tyr Asn Ser Ser Ser Gln Ile Thr
            980                 985                 990

Gln Ala Thr Pro Tyr Ala Thr Thr Gln Ile Leu His Ser Asn Ser Ile
            995                 1000                1005

His Glu Leu Ala Val Asp Leu Pro Asp Pro Gln Trp Lys Ser Ser
    1010                1015                1020

Ile Gln Gln Lys Thr Asp Leu Met Gly Phe Gly Tyr Ser Leu Pro
    1025                1030                1035

Asp Gln Asn Lys Gly Asn Asn Gly Gly Lys Gly Lys Lys Lys
    1040                1045                1050

Lys Asn Lys Asn Ser Ser Lys Pro Gln Lys Asn Asn Gly Ser Thr
    1055                1060                1065

Trp Ala Asn Val Pro Leu Pro Pro Val Gln Pro Leu Pro
    1070                1075                1080

Gly Thr Glu Leu Glu His Tyr Ala Val Glu Gln Glu Asn Gly
    1085                1090                1095

Tyr Asp Ser Asp Ser Trp Cys Pro Pro Leu Pro Val Gln Thr Tyr
    1100                1105                1110

Leu His Gln Gly Leu Glu Asp Glu Leu Glu Glu Asp Asp Arg
    1115                1120                1125

Val Pro Thr Pro Pro Val Arg Gly Val Ala Ser Ser Pro Ala Ile
    1130                1135                1140

Ser Phe Gly Gln Gln Ser Thr Ala Thr Leu Thr Pro Ser Pro Arg
    1145                1150                1155

Glu Glu Met Gln Pro Met Leu Gln Ala His Leu Asp Glu Leu Thr
    1160                1165                1170

Arg Ala Tyr Gln Phe Asp Ile Ala Lys Gln Thr Trp His Ile Gln
    1175                1180                1185

Ser Asn Asn Gln Pro Pro Gln Pro Pro Val Pro Pro Leu Gly Tyr
    1190                1195                1200

Val Ser Gly Ala Leu Ile Ser Asp Leu Glu Thr Asp Val Ala Asp
    1205                1210                1215

Asp Asp Ala Asp Asp Glu Glu Glu Ala Leu Glu Ile Pro Arg Pro
    1220                1225                1230

Leu Arg Ala Leu Asp Gln Thr Pro Gly Ser Ser Met Asp Asn Leu
    1235                1240                1245

Asp Ser Ser Val Thr Gly Lys Ala Phe Thr Ser Ser Gln Arg Pro
    1250                1255                1260

Arg Pro Thr Ser Pro Phe Ser Thr Asp Ser Asn Thr Ser Ala Ala
    1265                1270                1275

Leu Ser Gln Ser Gln Arg Pro Arg Pro Thr Lys Lys His Lys Gly
    1280                1285                1290

Gly Arg Met Asp Gln Gln Pro Ala Leu Pro His Arg Arg Glu Gly
    1295                1300                1305

Met Thr Asp Glu Glu Ala Leu Val Pro Tyr Ser Lys Pro Ser Phe
    1310                1315                1320
```

```
Pro Ser Pro Gly Gly His Ser Ser Ser Gly Thr Ala Ser Ser Lys
    1325            1330                1335

Gly Ser Thr Gly Pro Arg Lys Thr Glu Val Leu Arg Ala Gly His
    1340            1345                1350

Gln Arg Asn Ala Ser Asp Leu Leu Asp Ile Gly Tyr Met Gly Ser
    1355            1360                1365

Asn Ser Gln Gly Gln Phe Thr Gly Glu Leu
    1370            1375

<210> SEQ ID NO 25
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 25

His His His His His His
1               5
```